US011359184B2

(12) United States Patent
Ong et al.

(10) Patent No.: US 11,359,184 B2
(45) Date of Patent: *Jun. 14, 2022

(54) THERMOSTABLE VARIANTS OF T7 RNA POLYMERASE

(71) Applicant: New England Biolabs, Inc., Ipswich, MA (US)

(72) Inventors: Jennifer Ong, Salem, MA (US); Vladimir Potapov, Auburndale, MA (US); Kuo-Chan Hung, Ipswich, MA (US); Haruichi Asahara, Ipswich, MA (US); Shaorong Chong, Ipswich, MA (US); George Tzertzinis, Ipswich, MA (US)

(73) Assignee: New England Biolabs, Inc., Ipswich, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/680,014

(22) Filed: Nov. 11, 2019

(65) Prior Publication Data

US 2020/0123513 A1 Apr. 23, 2020

Related U.S. Application Data

(63) Continuation of application No. 15/594,090, filed on May 12, 2017, now Pat. No. 10,519,431, which is a continuation-in-part of application No. PCT/US2017/013179, filed on Jan. 12, 2017.

(60) Provisional application No. 62/416,770, filed on Nov. 3, 2016, provisional application No. 62/278,161, filed on Jan. 13, 2016.

(51) Int. Cl.
*C12N 9/12* (2006.01)
*C12Q 1/6858* (2018.01)

(52) U.S. Cl.
CPC ......... *C12N 9/1247* (2013.01); *C12Q 1/6858* (2013.01); *C12Y 207/07006* (2013.01)

(58) Field of Classification Search
None
See application file for complete search history.

(56) References Cited

U.S. PATENT DOCUMENTS

| 5,773,258 A | 6/1998 | Birch et al. |
| 6,183,998 B1 | 2/2001 | Ivanov et al. |
| 9,062,292 B2 | 6/2015 | Coleman et al. |
| 2011/0256589 A1 | 10/2011 | Sobek et al. |
| 2015/0024435 A1 | 1/2015 | Boulain et al. |

FOREIGN PATENT DOCUMENTS

| EP | 2505641 | 3/2012 |
| EP | 2505641 A1 | 10/2012 |
| JP | 2009213499 | 9/2009 |
| WO | WO 01/66705 | 9/2001 |
| WO | WO 2012170436 | 12/2012 |

OTHER PUBLICATIONS

Guo et al., PNAS, vol. 101, No. 25, pp. 9205-9210, Jun. 2004.*
Ngo et al. in The Protein Folding Problem and Tertiary Structure Prediction, 1994, Merz et al. (ed.), Birkhauser, Boston, MA, pp. 433 and 492-495.*
Geer, et al. Genome Research 12:1619-1623 (2002).
Kellogg, et al., Biotechniques, 16(6):1134-7 (1994).
Dang, et al., Journal of Molecular Biology, 264(2), 268-278 (1996).
Fisher Scientific 2014/2016, catalog # F549L.
Dunn, et al., J Mol Biol. 166(4):477-535 (1983).
Ikeda, et al., J. Biol. Chem. 26, (16): 11322-11328 (1992).
Adhya, et al., PNAS 78(1), 147-151 (1981).
Martin, et al., Prog. Nucleic Acid Res. Mol. Biol., 80: 323-47 (2005).
Maslak, et al., Biochemistry, 33: 6918-6924 (1994).
Sousa, et al., Prog. Nucleic Acid Res. Mol. Biol., 73: 1-41 (2003).
Compton, Nature, 350 (6313):91-92 (1991).
Kievits, Journal of Virological Methods. 1991 35: 273-86 (1991).
Tyagi, Nat. Biotechnol. 14: 303-8 (1996).
Zhou, et al., Nucleic Acids Research, 40(16), 7932-7945 (2012).
International Search Report and Written Opinion of the International Searching Authority for International Application No. PCT/US2017/013179, dated May 24, 2017.
Biao, et al. Rapid Mutagenesis and Purification of Phage RNA Polymerases Protein Expression and Purification 1997 9, 142-151.
Cermakian, et al. On the Evolution of the Single-Subunit RNA Polymerases Mol. Evol 1997 45:671-681.
Cheetham, et al. Insights into transcription: structure and function of single-subunit DNA-dependent RNA polymerases. CurrOpin Struct Biol. 2000 10: 117-23.
Jeruzalmi, et al. Structure of T7 RNA polymerase complexed to the transcriptional inhibitor T7 lysozyme The EMBO J. 1998 17:14 4101-4113.
Jorgensen, et al. Specific Contacts between the Bacteriophage T3, T7, and SP6 RNA Polymerases and Their Promoters J. Biol. Chem 1991 266: 645-651.
Kochetkov, et al., Recent studies of T7 RNA polymerase mechanism FEBS Letters 440, 1998, 264-267.
McAllister, et al. Structure and function of the bacteriophage T7 RNA polymerase (or, the virtues of simplicity). Cell. Mol. Biol. Res. 1993 39:385-91.
Sastry, et al. Identification of the template-binding cleft of T7 RNA polymerase as the site for promoter binding by photochemical cross-linking with psoralen. Biochemistry 1996 35:13519-30.
Siegmund, et al. Screening mutant libraries of T7 RNA polymerase for candidates with increased acceptance of 2'-modified nucleotides Chem Commun 2012 48:9870-2.

(Continued)

*Primary Examiner* — Richard G Hutson
(74) *Attorney, Agent, or Firm* — New England Biolabs, Inc

(57) ABSTRACT

A bacteriophage RNA polymerase variant is provided. In some embodiments, the variant may have increased thermostability relative to the corresponding wild type bacteriophage RNA polymerase and/or wild type T7 RNA polymerase. Compositions, kits and methods that employ the variant are also provided.

20 Claims, 8 Drawing Sheets

Specification includes a Sequence Listing.

(56) References Cited

OTHER PUBLICATIONS

Sousa, et al. Crystal structure of bacteriophage T7 RNA polymerase at 3.3 A resolution. Nature. 1993 364:593-9.
Sousa, et al. T7 RNA Polymerase, Progress in Nucleic Acid Research and Molecular Biology, 2003, 73: 1-41.
Sousa, et al. Single crystals of a chimeric T7/T3 RNA polymerase with T3 promoter specificity and a nonprocessive T7 RNAP mutant. J Biol Chem. 1990 265: 21430-2.
Tunitskaya, et al. Structural-functional analysis of bacteriophage T7 RNA polymerase. Biochemistry 2002 67:1124-35.

* cited by examiner

THERMOSTABLE VARIANTS OF T7 RNA POLYMERASE

CROSS-REFERENCING

This application is a continuation of U.S. application Ser. No. 15/594,090, filed on May 12, 2017 which is a continuation-in-part of application serial no. PCT/US2017/13179, filed on Jan. 12, 2017, which claims the benefit of U.S. provisional application Ser. No. 62/416,770, filed Nov. 3, 2016, and U.S. provisional application Ser. No. 62/278,161, filed on Jan. 13, 2016, all of which applications are incorporated by reference herein.

BACKGROUND

Thermostable and thermoactive enzymes have great utility in academic research and industrial applications. The high stability of enzymes from thermophilic organisms enables technologies in molecular biology and diagnostics (the Polymerase Chain Reaction, for example). However, equivalent enzymes from thermophilic organisms are not always available. In these cases, directed evolution or computational methods can serve as a powerful tool to identify variants of mesophilic enzymes that confer thermostability. For example, current in vitro transcription methods are limited to reaction temperatures below 45° C. The typical viral RNA polymerases that carry out these reactions are not active at elevated temperatures, and there is a need to identify thermoactive and stable variants in order to carry out in vitro transcription reactions at elevated temperatures.

SUMMARY

A bacteriophage RNA polymerase variant is provided. In some embodiments, the variant may have increased thermostability and/or activity at elevated reaction temperatures relative to a corresponding wild type RNA polymerase. Compositions, kits and methods that employ the variant are also provided.

In some embodiments, the variant: (i) comprises an amino acid sequence that has at least 80% (e.g., at least 90%, or at least 95%) sequence identity to SEQ ID NO:1; and (ii) comprises an amino acid substitution at one or more positions corresponding to positions 109, 205, 388, 534, 567 and 618 of SEQ ID NO:1. In some embodiments, the variant may comprise an amino acid substitution at least two positions corresponding to positions 109, 205, 388, 534, 567 and 618 of SEQ ID NO:1. In some embodiments, the variant may comprise an amino acid substitution at least three positions corresponding to positions 109, 205, 388, 534, 567 and 618 of SEQ ID NO:1. In some embodiments, the variant may comprise an amino acid substitution at positions corresponding to positions 109, 205, 388, 534, 567 and 618 of SEQ ID NO:1. For example, in some embodiments, the variant may comprise one or more of the following amino acids substitutions: I109L, H205S, D388E, L534V, V567P and G618Q wherein the amino acid substitutions are at positions that correspond to positions in SEQ ID NO:1.

In one example, variant further includes an amino acid substitution at one or more positions corresponding to positions: 75, 83, 108, 206, 227, 281, 297, 312, 323, 327, 333, 340, 354, 362, 375, 428, 446, 454, 461, 495, 510, 584, 591, 642, 711, 724, 740, 788, 832, 834, 835, 843, 847, 849, 856, 863, 866 and 877 of SEQ ID NO:1.

In another example, the variant may further comprise an amino acid substitution of at least 10 positions corresponding to positions: 75, 83, 108, 206, 227, 281, 297, 312, 323, 327, 333, 340, 354, 362, 375, 428, 446, 454, 461, 495, 510, 584, 591, 642, 711, 724, 740, 788, 832, 834, 835, 843, 847, 849, 856, 863, 866 and 877 of SEQ ID NO:1.

In another example, the variant may further comprise one or more of the following amino acids substitutions: T75Q, A83K, E108L, K206P, V227I, I281P, V297I, Y312D, A323I, A327P, K333P, V340E, A354Q, M362P, T375K, T375N, A428P, L446F, K454P, K461R, S495N, C510Q, A584K, D591E, K642R, K711R, A724P, K740R, G788A, M832F, D834E, T835L, A843Q, D847E, F849V, S856T, A863P, A866K and E877R, wherein the amino acid substitutions are at positions that correspond to positions in SEQ ID NO:1.

In another example, the isolated bacteriophage RNA polymerase variant, wherein the variant includes at least 10 of the following amino acids substitutions: T75Q, A83K, E108L, K206P, V227I, I281P, V297I, Y312D, A323I, A327P, K333P, V340E, A354Q, M362P, T375K, T375N, A428P, L446F, K454P, K461R, S495N, C510Q, A584K, D591E, K642R, K711R, A724P, K740R, G788A, M832F, D834E, T835L, A843Q, D847E, F849V, S856T, A863P, A866K, and E877R, wherein the amino acid substitutions are at positions that correspond to positions in SEQ ID NO:1.

In some embodiments, any isolated bacteriophage RNA polymerase variant described above may include a fusion to an exogenous DNA binding domain. Examples are provided in Table 1. In another embodiment, the variant has increased stability at temperatures of at least 45° C. (e.g., at or above 50° C., or at or above 55° C.) relative the T7 RNA polymerase of SEQ ID NO:1 as a result of the one or more amino acid substitutions.

Also provided is a composition that includes i. an isolated bacteriophage RNA polymerase variant described above; and ii. a buffering agent. The composition may further include ribonucleoside triphosphates and/or modified nucleotides. The composition may further include a template DNA molecule comprising: a bacteriophage promoter (e.g., a T7 or T3 RNA polymerase promoter) operably linked to a target nucleotide sequence to be transcribed.

Also provided is a kit is provided that includes i. an isolated bacteriophage RNA polymerase variant of any of those described above; and ii. a reaction buffer. The kit may further comprise one or more ribonucleoside triphosphates and/or modified nucleotides.

Also provided is a method is provided for synthesizing an RNA molecule that includes (a) combining an isolated bacteriophage RNA polymerase variant described above with ribonucleoside triphosphates and/or modified nucleotides and a template DNA molecule comprising a bacteriophage RNA promoter that is operably linked to a target nucleotide sequence to be transcribed, to produce a reaction mix; and (b) incubating the reaction mix to transcribe the template DNA molecule into RNA.

In one embodiment, a method is provided for synthesizing an RNA molecule that includes (a) incubating the reaction mix described above comprising an isolated bacteriophage RNA polymerase variant described above with ribonucleoside triphosphates and/or modified nucleotides and a template DNA molecule comprising a bacteriophage RNA promoter that is operably linked to a target nucleotide sequence to be transcribed, thereby transcribing the template DNA molecule into RNA.

In one aspect, the incubating is done at a temperature of at least 45° C. or at above 50° C. or at above 55° C. (for example 45° C. to 60° C., 45° C. to 50° C., 50° C. to 55° C. or 55° C. or 60° C.).

One example of a bacteriophage RNA polymerase is T7 RNA polymerase.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The skilled artisan will understand that the drawings, described below, are for illustration purposes only. The drawings are not intended to limit the scope of the present teachings in any way.

FIG. 1A-1C show data for selected variants that have individual mutations. These reactions were done at 45° C. for 10 hours (FIG. 1A and FIG. 1B) and at 37° C. for 2 hours followed by 45° C. for 8 hours (FIG. 1C). FIG. 1D shows the additive effect of individual mutations identified by Tth PURE assay. The reaction was carried out at 45° C. for 10 hours. The thermostability of variants was estimated using the formula, (M−WT)/WT, in which M and WT stand for the maximum value of fluorescent signal from synthesized GFP in 10-hour reactions with mRNA of T7 RNA polymerase variant and wild-type, respectively. In this assay, if a variant polymerase has an activity of "0" then it has the equivalent activity as the wild type T7 RNA polymerase. If a variant polymerase has an activity of "0.5" then it has a 50% increase in activity relative to the wild type T7 RNA polymerase.

FIGS. 1A-1C show results for 45 single amino acid variants of T7 RNA polymerase.

FIG. 1D shows the additive effect of combining amino acid substitutions. In FIG. 1D, the additive effect of 1, 2, 3, 4, 5 and 6 amino acids substitutions is shown.

FIG. 3A shows the transcription activity (RNA synthesis yield) at increased temperature for the wild type T7 RNA polymerase, as well as two variants, commercial T7 RNA polymerase from Toyobo "Toyobo" and M20 where M20 is a mutant of T7 RNA polymerase with 20 amino acid substitutions. As shown, the M20 variant is highly active at temperatures at above 55° C.

FIG. 3B is a graph showing the transcription activity of wild type T7 polymerase compared to the activity of a variant M18 and a variant M13 and a fusion protein containing the M18 variant and the DNA binding domain of a lacI-like protein from *Thermotoga* (007) after a 20 minute incubation. As shown the M13 and M18 variants and also the M18 fusion protein is highly active at temperatures at above 55° C. with the fusion protein maintaining its activity (Fluorescence units on the Y axis corresponds to amount of RNA).

FIG. 3C shows a comparison between wild type, mutant and fusion between mutant and DNA binding domain of a thermostable protein (see Table 1) in which not only is the activity of the fusion variant higher at increasing temperature than the variant alone but also there is slower reduction of activity at temperatures about 56° C. compared to the wild type.

FIG. 7A shows the results of a quantitative NASBA reaction using the M20 variant of T7 RNA polymerase. These reactions do not include DMSO.

FIG. 7B shows the results of a quantitative NASBA reaction using the M20 variant of T7 RNA polymerase. These reactions include 5% DMSO.

DEFINITIONS

Figure 1C:
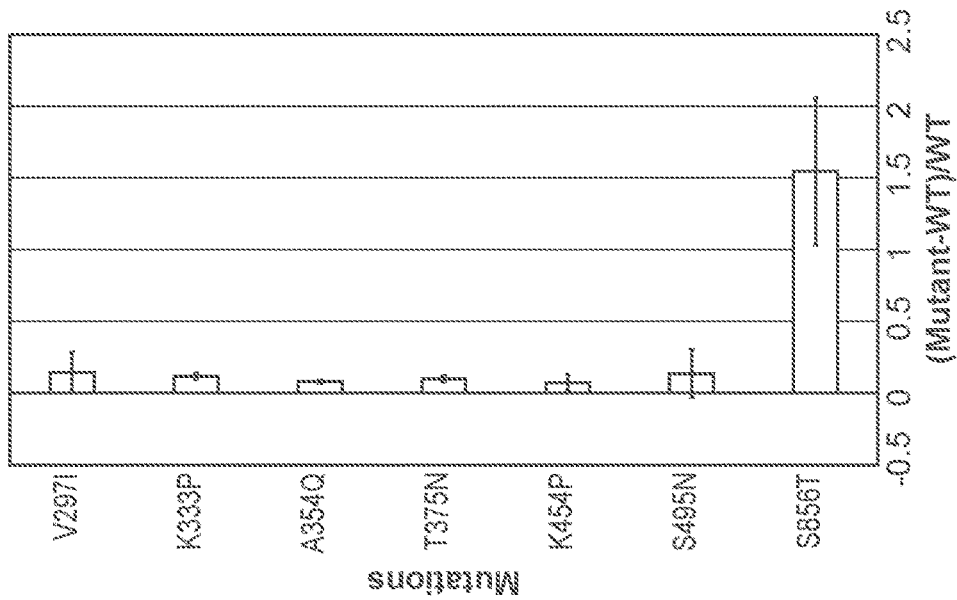
FIGS. 1A-1D are graphs showing the effect of various amino acid substitutions on the activity of T7 RNA polymerase (SEQ ID NO: 1).

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "non-naturally occurring" refers to a composition that does not exist in nature.

In the context of a protein, the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence but that is at least 80%, at least 85%, at least 90%, at least 95%, at least 97%, at least 98% or at least 99% identical to a naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell.

In the context of a nucleic acid, the term "non-naturally occurring" refers to a nucleic acid that contains: a) a sequence of nucleotides that is different to a nucleic acid in its natural state, b) one or more non-naturally occurring nucleotide monomers (which may result in a non-natural backbone or sugar that is not G, A, T or C) and/or C) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; e) a combination that is in a form that not found in nature, e.g., dried, freeze dried, crystalline, aqueous; and/or d) a combination that contains a component that is not found in nature. For example, a preparation may contain a buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

As used herein, the term "buffering agent", refers to an agent that allows a solution to resist changes in pH when acid or alkali is added to the solution. Examples of suitable non-naturally occurring buffering agents that may be used in the compositions, kits, and methods of the invention include, for example, Tris, HEPES, TAPS, MOPS, tricine, or MES.

The term "corresponding to" in the context of corresponding positions, refers to positions that lie across from one another when sequences are aligned, e.g., by the BLAST algorithm.

The term "variant T7 RNA polymerase" may encompass other types of bacteriophage RNA polymerase with sequences of at least 80% identity to wild type T7 RNA polymerase (SEQ ID NO:1). Enzymes having a similar architecture can be identified using the Conserved Domain Architecture Retrieval Tool (CDART) program of the National Center for Biotechnology Information (Geer, et al. Genome Research 12:1619-1623 (2002)) or by other predictive programs, based on searches employing the sequence of T7 RNA polymerase. Examples of enzymes identified in this manner include: T odd bacteriophages or related viruses including Enterobacteria bacteriophage T7, *Yersinia pestis* bacteriophage phiA1122; *Pseudomonas* bacteriophage gh-1; bacteriophage of *Pseudomonas putida*; Bacteriophage T3; Roseophage SIO1; and Bacteriophage phiYeO3-12. In addition, other related bacteriophages such as SP6, bacteriophage phiKMV, Enterobacteria bacteriophage K1-5, Vibriophage VpV262, BA14, BA127 and BA156 may encode similar enzymes.

The term "fusion protein" refers to a DNA binding domain linked to a wild type or variant polymerase. Examples include *Pyrococcus furiosus* (109-T7) and the DNA binding domain of a lacI-like protein from *Thermotoga* (007-T7). Other examples are listed in Table 1.

TABLE 1

| DNA binding proteins | | | |
|---|---|---|---|
| DNA-binding protein Tfx | BD-51 | gi\|499321160 | SEQ ID NO:10 |
| AbrB/MazE/MraZ-like | BD-52 | gi\|499321199 | SEQ ID NO:11 |
| "Winged helix" DNA-binding domain | BD-54 | gi\|499322061 | SEQ ID NO:12 |
| Ribbon-helix-helix protein, copG family | BD-62 | gi\|499321149 | SEQ ID NO:13 |
| lambda repressor-like DNA-binding domains | BD-63 | gi\|499322443 | SEQ ID NO:14 |
| Resolvase-like | BD-67 | gi\|499322676 | SEQ ID NO:15 |
| "Winged helix" DNA-binding domain | BD-71 | gi\|499322676 | SEQ ID NO:16 |
| "Winged helix" DNA-binding domain | BD-74 | gi\|499322255 | SEQ ID NO:17 |
| "Winged helix" DNA-binding domain | BD-75 | gi\|499322388 | SEQ ID NO:18 |
| "Winged helix" DNA-binding domain | BD-81 | gi\|499322131 | SEQ ID NO:19 |
| "Winged helix" DNA-binding domain | BD-82 | gi\|499321342 | SEQ ID NO:20 |
| "Winged helix" DNA-binding domain | BD-85 | gi\|499321130 | SEQ ID NO:21 |
| "Winged helix" DNA-binding domain | BD-86 | gi\|499322705 | SEQ ID NO:22 |
| "Winged helix" DNA-binding domain | BD-88 | gi\|499320855 | SEQ ID NO:23 |
| "Winged helix" DNA-binding domain | BD-89 | gi\|499322250 | SEQ ID NO:24 |
| "Winged helix" DNA-binding domain | BD-91 | gi\|499321633 | SEQ ID NO:25 |
| "Winged helix" DNA-binding domain | BD-92 | gi\|490170077 | SEQ ID NO:26 |
| "Winged helix" DNA-binding domain | BD-93 | gi\|499321272 | SEQ ID NO:27 |
| "Winged helix" DNA-binding domain | BD-94 | gi\|499320919 | SEQ ID NO:28 |
| "Winged helix" DNA-binding domain | BD-97 | gi\|499320853 | SEQ ID NO:29 |
| "Winged helix" DNA-binding domain | BD-98 | gi\|499321734 | SEQ ID NO:30 |
| "Winged helix" DNA-binding domain | BD-100 | gi\|499322439 | SEQ ID NO:31 |

TABLE 1-continued

| DNA binding proteins | | | |
|---|---|---|---|
| "Winged helix" DNA-binding domain | BD-102 | gi|499322707 | SEQ ID NO:32 |
| "Winged helix" DNA-binding domain | BD-109 | gi|499321112 | SEQ ID NO:33 |
| HCP-like | BD-02 | gi|351675391 | SEQ ID NO:34 |
| Helix-turn-helix domain, rpiR family | BD-03 | gi|500479591 | SEQ ID NO:35 |
| Helix-turn-helix domain, rpiR family | BD-04 | gi|15643984 | SEQ ID NO:36 |
| Bacterial regulatory proteins, lacI family | BD-07 | gi|15643711 | SEQ ID NO:37 |
| Bacterial regulatory proteins, lacI family | BD-08 | gi|15643974 | SEQ ID NO:38 |
| Bacterial regulatory proteins, lacI family | BD-09 | gi|15643956 | SEQ ID NO:39 |
| Bacterial regulatory proteins, lacI family | BD-11 | gi|500480095 | SEQ ID NO:40 |
| lambda repressor-like DNA-binding domains | BD-12 | gi|15643421 | SEQ ID NO:41 |
| "Winged helix" DNA-binding domain | BD-14 | gi|15644350 | SEQ ID NO:42 |
| "Winged helix" DNA-binding domain | BD-16 | gi|24159093 | SEQ ID NO:43 |
| "Winged helix" DNA-binding domain | BD-18 | gi|15643139 | SEQ ID NO:44 |
| "Winged helix" DNA-binding domain | BD-23 | gi|15642807 | SEQ ID NO:45 |
| "Winged helix" DNA-binding domain | BD-24 | gi|15643159 | SEQ ID NO:46 |
| "Winged helix" DNA-binding domain | BD-30 | gi|15643333 | SEQ ID NO:47 |
| "Winged helix" DNA-binding domain | BD-32 | gi|15643055 | SEQ ID NO:48 |
| "Winged helix" DNA-binding domain | BD-37 | gi|15643827 | SEQ ID NO:49 |
| "Winged helix" DNA-binding domain | BD-43 | gi|15643699 | SEQ ID NO:50 |
| Homeodomain-like | BD-45 | gi|15643788 | SEQ ID NO:51 |

The term "temperature-sensitive inhibitor" includes antibody-based hot start RNA polymerase inhibitors where examples of hot start inhibitors for polymerases is provided in Kellogg, et al., Biotechniques, 16(6):1134-7 (1994); aptamer based hot start RNA polymerases where examples for polymerases are provided by New England Biolabs, Ipswich, Mass. (catalog #M0495) and also described by Dang, et al., Journal of Molecular Biology, 264(2), 268-278 (1996); Affibody-based hot start inhibitors where Affibody is a protein-based ligand that inhibits DNA polymerase and exonuclease activity at low temperatures but not at higher temperatures (also described by (Thermo Fisher Scientific, Waltham, Mass. catalog #F549L); and chemical modification resulted in hot start RNA polymerase (see for example U.S. Pat. Nos. 5,773,258; and 6,183,998).

The term "promoter sequence" includes the sequence 5'-TAATACGACTCACTATAG-3' (SEQ ID NO:74) and any sequence that is at least 90% identical to the canonical sequences for T7. See also Dunn, et al., J Mol Biol. 166(4):477-535 (1983) and Ikeda, et al., J. Biol. Chem. 26, (16): 11322-11328 (1992). This definition also includes the T3 promoter 5' AATTAACCCTCACTAAAG 3' (SEQ ID NO:75) (see New England Biolabs, Ipswich, Mass.) or TATTTACCCTCACTAAAG (SEQ ID NO:76) (Adhya, et al., PNAS 78(1), 147-151 (1981). SP6 promoter has a sequence ATTTAGGTGACACTATAGAAGNG (SEQ ID NO:77) (Thermo Fisher Scientific, Waltham, Mass.). Other promoter sequences are known.

As used herein, the term "incubating", refers to maintaining a reaction a suitable temperature and time to achieve the desired results, i.e., transcription. Reaction conditions suitable for the enzymes and reagents used in the present method are known (e.g. as described in the Examples herein) and, as such, suitable reaction conditions for the present method can be readily determined. These reactions conditions may change depending on the enzymes used (e.g., depending on their optimum temperatures, etc.).

As used herein, the term "composition" refers to a combination of reagents that may contain other reagents, e.g., glycerol, salt, dNTPs, etc., in addition to those listed. A composition may be in any form, e.g., aqueous or lyophilized, and may be at any state (e.g., frozen or in liquid form).

DETAILED DESCRIPTION

Before various embodiments are described in greater detail, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to a half of the unit of the lower limit unless the context clearly dictates otherwise, between the upper and lower limit of that range and any other stated or intervening value in that stated range is encompassed within the present disclosure.

Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Variants and Compositions Containing the Same

Provided herein, in various embodiments, are isolated bacteriophage RNA polymerases belonging to the closely related family of bacteriophage RNA polymerases having at least 80% amino acid sequence identity with T7 RNA polymerase that may be engineered to contain one or more amino acid substitutions corresponding to those identified for T7 RNA polymerase described herein. The isolated bacteriophage RNA polymerase variants may be organized by their improved activity at temperatures of 42° C. and above compared to the corresponding wild type enzyme or wild type T7 RNA polymerase. In some embodiments, the variant: (i) may have an amino acid sequence is at least 80% sequence identity (e.g., at least 90%, at least 90%, at least 95%, at least 97%, at least 98% or at least 99% identity) to SEQ ID NO:1; and (ii) may comprise one or more (e.g., at least two, at least three, at least five, or at least ten) amino acid substitutions at one or more positions corresponding to positions 75, 83, 108, 109, 205, 206, 227, 281, 297, 312, 323, 327, 333, 340, 354, 362, 375, 388, 428, 446, 454, 461, 495, 510, 534, 567, 584, 591, 618, 642, 711, 724, 740, 788, 832, 834, 835, 843, 847, 849, 856, 863, 866, and 877 of SEQ ID NO:1 (wild-type T7 RNA polymerase), shown below:

```
SEQ ID NO: 1:
MNTINIAKNDFSDIELAAIPFNTLADHYGERLAREQLALEHESYEMGEAR

FRKMFERQLKAGEVADNAAAKPLITTLLPKMIARINDWFEEVKAKRGKRP

TAFQFLQEIKPEAVAYITIKTTLACLTSADNTTVQAVASAIGRAIEDEAR

FGRIRDLEAKHFKKNVEEQLNKRVGHVYKKAFMQVVEADMLSKGLLGGEA

WSSWHKEDSIHVGVRCIEMLIESTGMVSLHRQNAGVVGQDSETIELAPEY

AEAIATRAGALAGISPMFQPCVVPPKPWTGITGGGYWANGRRPLALVRTH

SKKALMRYEDVYMPEVYKAINIAQNTAWKINKKVLAVANVITKWKHCPVE

DIPAIEREELPMKPEDIDMNPEALTAWKRAAAAVYRKDKARKSRRISLEF

MLEQANKFANHKAIWFPYNMDWRGRVYAVSMFNPQGNDMTKGLLTLAKGK

PIGKEGYYWLKIHGANCAGVDKVPFPERIKFIEENHENIMACAKSPLENT

WWAEQDSPFCFLAFCFEYAGVQHHGLSYNCSLPLAFDGSCSGIQHFSAML

RDEVGGRAVNLLPSETVQDIYGIVAKKVNEILQADAINGTDNEVVTVTDE

NTGEISEKVKLGTKALAGQWLAYGVTRSVTKRSVMTLAYGSKEFGFRQQV

LEDTIQPAIDSGKGLMFTQPNQAAGYMAKLIWESVSVTVVAAVEAMNWLK

SAAKLLAAEVKDKKTGEILRKRCAVHWVTPDGFPVWQEYKKPIQTRLNLM

FLGQFRLQPTINTNKDSEIDAHKQESGIAPNFVHSQDGSHLRKTVVWAHE

KYGIESFALIHDSFGTIPADAANLFKAVRETMVDTYESCDVLADFYDQFA

DQLHESQLDKMPALPAKGNLNLRDILESDFAFA
```

For example, in some embodiments, the variant may comprise substitutions at one or more (e.g., one, two, three, four, five or all six) positions corresponding to positions 109, 205, 388, 534, 567 and 618 of SEQ ID NO:1, as well as well as optionally one or more (e.g., at least two, at least three, at least five, or at least ten) other substitutions at other substitutions listed above (see for example FIG. 1A-1D, FIG. 2, FIG. 3A-3C, FIG. 4 and FIG. 5).

In some embodiments, the isolated T7 RNA polymerase variant: (i) has an amino acid sequence is at least 80% sequence identity (e.g., at least 90%, at least 95%, at least 97%, at least 98% or at least 99% identity) to SEQ ID NO:1; and (ii) comprises one or more (e.g., at least two, at least three, at least five, or at least ten) of the following amino acid substitutions: T75Q, A83K, E108L, K206P, V227I, I281P, V297I, Y312D, A323I, A327P, K333P, V340E, A354Q, M362P, T375K, T375N, A428P, L446F, K454P, K461R, S495N, C510Q, A584K, D591E, K642R, K711R, A724P, K740R, G788A, M832F, D834E, T835L, A843Q, D847E, F849V, S856T, A863P, A866K, and E877R, wherein the amino acid substitutions are at positions that correspond to positions in SEQ ID NO:1 (see for example FIG. 1A-1D, FIG. 2, FIG. 3A-3C, FIG. 4 and FIG. 5).

In some embodiments, the variant comprises one or more (e.g., one, two, three, four, five or all six) of the following amino acid substitutions: I109L, H205S, D388E, L534V, V567P and G618Q, wherein the amino acid substitutions are at positions that correspond to positions in SEQ ID NO:1, as well as well as optionally one or more (e.g., at least two, at least three, at least five, or at least ten) of the following amino acid substitutions: T75Q, A83K, E108L, K206P, V227I, I281P, V297I, Y312D, A323I, A327P, K333P, V340E, A354Q, M362P, T375K, T375N, A428P, L446F, K454P, K461R, S495N, C510Q, A584K, D591E, K642R, K711R, A724P, K740R, G788A, M832F, D834E, T835L, A843Q, D847E, F849V, S856T, A863P, A866K, and E877R, wherein the amino acid substitutions are at positions that correspond to positions in SEQ ID NO:1 (see for example FIG. 1A-1D, FIG. 2, FIG. 3A-3C, FIG. 4 and FIG. 5).

As would be apparent, RNA polymerase variants described herein have RNA polymerase activity and, as such, can catalyze the formation of RNA in the 5'→3' direction using a DNA template. T7 RNA polymerase is a promoter-specific polymerase that transcribes downstream of a suitable promoter (e.g., TAATACGACTCACTATAG; SEQ ID NO:2). In certain embodiments, the non-natural bacteriophage RNA polymerase may activate transcription from a promoter that has at least 90% sequence identity with SEQ ID NO:2; AATTAACCCTCACTAAAG (SEQ ID NO:3); TATTTACCCTCACTAAAG (SEQ ID NO:4) or ATTTAGGTGACACTATAGAAGNG (SEQ ID NO:5). Transcription typically beginnings at the 3' G nucleotide. The polymerase variants also preferably utilize $Mg^{2+}$ ion as cofactor for the synthesis of RNA.

T7 RNA polymerase which is generally described in Maslak et al, Biochemistry 1994, 33: 6918-6924; Martin et al Prog. Nucleic Acid Res. Mol. Biol. 2005 80: 323-47; and Sousa et al Prog. Nucleic Acid Res. Mol. Biol. 2003 73: 1-41, is structurally related to other bacteriophage polymerases such as T3 polymerase (NP_523301.1) and SP6 polymerase (YP_004306655.1) as well as the RNA polymerases from *Yersinia* bacteriophage phiYeO3-12, *Erwinia* bacteriophage FE44, *Kluyvera* bacteriophage Kvp1, Enterobacteria bacteriophage K1F, *Vibrio* bacteriophage ICP3_2009_A and *Pseudomonas* bacteriophage PPPL-1. It is expected that the amino add substitutions described herein may be transferred to other, related RNA polymerases and their variants with the same effect. As such, in certain embodiments, this disclosure provides a non-naturally occurring variant of a naturally occurring bacteriophage RNA polymerase, wherein the variant has an amino acid that is at least 80% identical to (e.g., at least 90%, at least 95% or at least 98% identical to) the naturally occurring bacteriophage RNA polymerase and comprises one or more amino acid substitutions relative the naturally occurring to bacteriophage RNA polymerase, wherein the one or more amino acid substitutions are at one or more position listed above.

In some embodiments, an isolated bacteriophage RNA polymerase variant with one or more amino acid substitutions has increased stability at 45° C. or greater relative to the wild type RNA polymerase. This is here exemplified by a T7 RNA polymerase variant, having one or more amino acid substitutions, and by a fusion between the bacteriophage RNA polymerase and a DNA binding protein such as described in Table 1 and in Example 3. In some embodiments, an isolated bacteriophage RNA polymerase variant exemplified by a T7 RNA polymerase variant may be used in an in vitro transcription reaction that is incubated at an elevated temperature (e.g., a temperature in the range of for example, 45° C. to 60° C., 45° C. to 50° C., 50° C. to 55° C. or 55° C. or 60° C.) to produce at least 10% more product, at least 20% more product, at least 50% more product, at least 100% more product, or at least 500% more product than an otherwise identical reaction containing the wild type RNA polymerase (e.g. SEQ ID NO:1 for T7 RNA polymerase) incubated under the same conditions.

Also provided is a composition, e.g., an aqueous composition comprising: i. an isolated bacteriophage RNA polymerase variant (e.g., a T7 RNA polymerase described herein) and ii. a buffering agent (e.g., Tris). In some embodiments, the composition may be a composition in which the polymerase can be stored. In these embodiments, the composition may optionally contain glycerol, salt (e.g., NaCl), EDTA, detergent (e.g., Triton X-100). In other embodiments, the composition may be a reaction mix. In these embodiments, the composition may further comprise ribonucleoside triphosphates (e.g., one, two, three or all four of ATP, UTP, GTP, CTP) and/or one or more modified nucleotides. In some embodiments, the composition may further comprise a template DNA molecule comprising: a bacteriophage promoter operably linked to a target nucleotide sequence to be transcribed. In some embodiments, the composition may comprise a population of such template DNA molecules, where each of the template molecules comprises a bacteriophage promoter upstream from a target nucleotide sequence to be transcribed. The bacteriophage promoter can be any of those described herein such as a T7 promoter, a T3 promoter or an SP6 promoter. A reaction mix composition may additionally contain 4-10 mM $MgCl_2$, e.g., 6 mM, $MgCl_2$.

Figure 4:
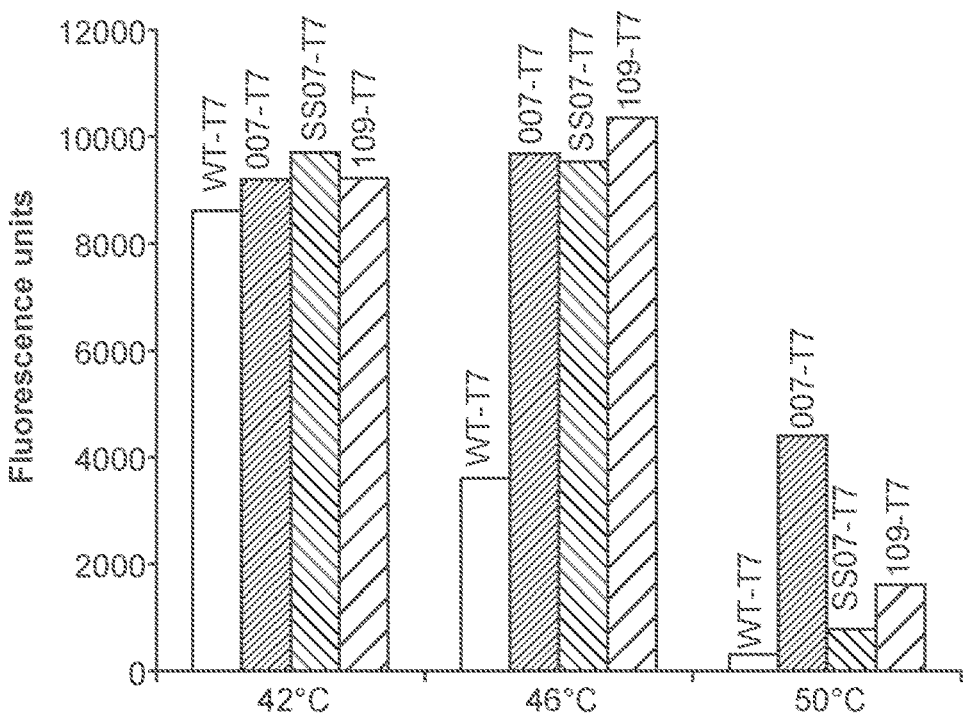
FIG. 4 is a graph showing the transcription activity of wild type T7 RNA polymerase at different temperatures, compared to the transcription activity of the same T7 RNA polymerase fused to the SS07 DNA binding domain (SS07-T7), the DNA binding domain from a helix-turn-helix (HTH) from *Pyrococcus furiosus* (109-T7) and the DNA binding domain of a lacI-like protein from *Thermotoga* (007-T7). The fusion proteins containing T7 RNA polymerase and each of the three DNA binding domain are more active at high temperatures than wild type T7 RNA polymerase.
Figure 5:
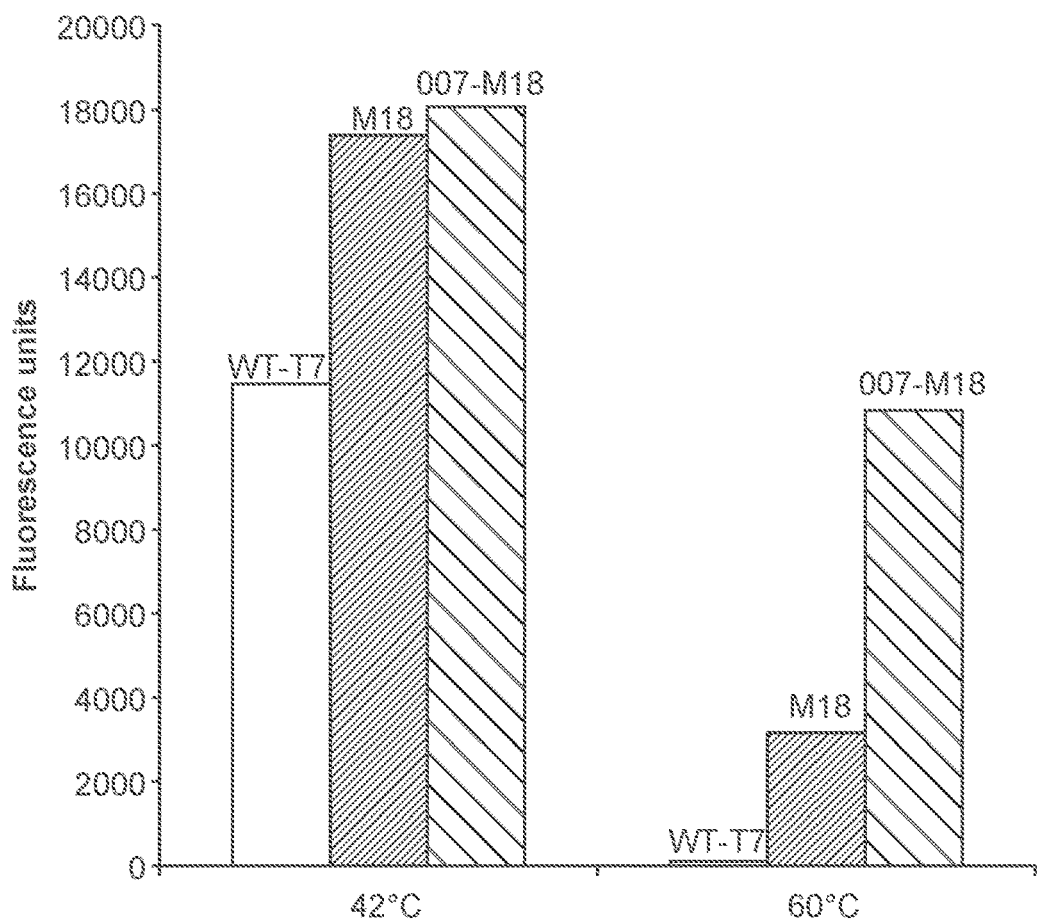
FIG. 5 is a graph showing the transcription activity of wild type T7 polymerase compared to the activity of variant M18 which contains 18 amino acid substitutions and a fusion protein containing the M18 variant and the DNA binding domain of a lacI-like protein from *Thermotoga* (007). Fusion proteins containing thermostable T7 RNA polymerase variants and a DNA binding domain are more active at high temperatures than the thermostable T7 RNA polymerase variants.
Figure 6:
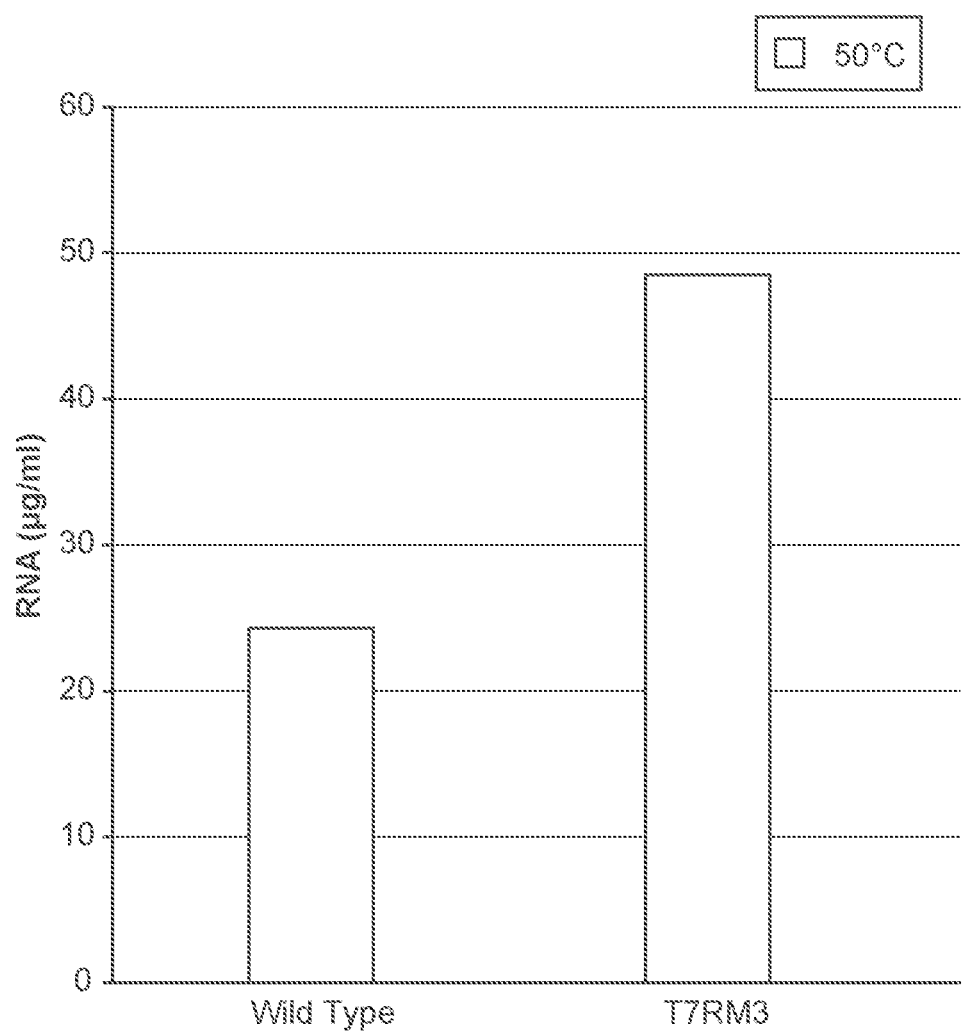
FIG. 6 shows improved thermostability for the T7 RNA polymerase variant identified in SEQ ID NO:70 at 50° C. compared with T7 RNA polymerase wild type under the same reaction conditions.

In some embodiments, a variant may be fused to a DNA binding domain, the activity of the RNA polymerase may be enhanced at elevated temperatures by 50% or 100% or 150% or 200% or more (see for example, FIG. 4 or FIG. 5).

Kits

Also provided is a kit comprising: i. an isolated bacteriophage RNA polymerase variant as described herein; and ii. a reaction buffer. In some embodiments, the kit may further comprise one or more ribonucleoside triphosphates (e.g., one, two, three or all four of ATP, UTP, GTP, CTP). The components of the kit may be combined in one container, or each component may be in its own container. For example, the components of the kit may be combined in a single reaction tube or in one or more different reaction tubes. Further details of the components of this kit are described above. The kit may also contain other reagents described above and below that may be employed in the method depending on how the method is going to be implemented. In some embodiments, the kit may comprise of a variant as described above and a buffer in which the variant is active, or a concentrated form thereof.

In addition to above-mentioned components, the subject kit may further include instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Methods

Also provided is a method for synthesizing an RNA molecule. In some embodiments, this method may comprise (a) combining an isolated bacteriophage RNA polymerase variant described herein with ribonucleoside triphosphates and/or modified nucleotides and a template DNA molecule comprising a promoter operably linked to a target nucleotide sequence to be transcribed, to produce a reaction mix; and (b) incubating the reaction mix to transcribe the template DNA molecule into RNA. In some embodiments, the incubating may be done at a temperature of at least 45° C. (e.g., in the range of 45° C. to 60° C., 45° C. to 50° C., 50° C. to 55° C. or 55° C. or 60° C.) to transcribe the DNA into RNA. The DNA can be single- or double-stranded and should have a promoter recognized by the polymerase. In one embodiment, the method includes a T7 RNA polymerase variant and a T7 promoter or T3 promoter or variants thereof.

In some embodiments, the present RNA polymerase may be used to amplify RNA by NASBA (Nucleic Acid Sequence Based Amplification). NASBA was initially described by Compton (Nature, 350 (6313):91-92 (1991)) and has been used as a rapid diagnostic tests for several pathogenic viruses with RNA genomes, e.g. influenza A, foot-and-mouth disease virus, severe acute respiratory syndrome (SARS)-associated coronavirus, human bocavirus (HBoV) and also parasites like *Trypanosoma brucei* as well as other viruses such as HIV-1 (see, e.g., Kievits Journal of Virological Methods. 1991 35: 273-86). NASBA can be used for medical diagnostics, where it has been shown to give quicker results than PCR, and it can also be more sensitive. NASBA's is an isothermal reaction that is typically run at a constant temperature of at least 41° C. When a present variant is used, the incubation temperature can be increased to above at least 45° C. (e.g., in the range of 45° C. to 60° C., 45° C. to 50° C., 50° C. to 55° C. or 55° C. or 60° C.). In some implementations, when the RNA template is added the reaction mixture, a primer containing a promoter sequence hybridizes to a complementary site at the 3' end of the template, and reverse transcriptase synthesizes the opposite, complementary DNA strand. RNAse H destroys the RNA template from the DNA-RNA hybrid, and a second primer hybridizes to the 5' end of the cDNA strand. The second primer is extended using the cDNA as a template, resulting in double stranded DNA. A T7 RNA polymerase variant can continuously produce complementary RNA strands of this template, which results in amplification. The amplicons, however, are antisense to the original RNA template. A higher incubation temperature results in less non-specific binding of DNA primers to the RNA. In some embodiments, the reaction may contain temperature-sensitive inhibitor of the polymerase, thereby allowing the polymerase to remain inactive until the temperature is raised. In other embodiments, the present RNA polymerase may also be used to amplify RNA by TMA (Transcription-Mediated Amplification). TMA is an isothermal, single-tube nucleic acid amplification system utilizing two enzymes, RNA polymerase and reverse transcriptase, to rapidly amplify the target RNA/DNA, enabling the simultaneous detection of multiple pathogenic organisms in a single tube. TMA technology allows a clinical laboratory to perform nucleic acid test (NAT) assays for blood screening with fewer steps, less processing time, and faster results. It is used in molecular biology, forensics, and medicine for the rapid identification and diagnosis of pathogenic organisms. In contrast to similar techniques such as polymerase chain reaction and ligase chain reaction, this method involves RNA transcription (via RNA polymerase) and DNA synthesis (via reverse transcriptase) to produce an RNA amplicon (the source or product of amplification) from a target nucleic acid. This technique can be used for both target RNA and DNA. NASBA and TMA reactions that are performed at a higher temperature (e.g., in the range of 45° C. to 60° C.) produce less non-specific amplification products relative to the same reactions that are done at a lower temperature (e.g., 41° C.). Moreover, DMSO or other compounds that lower the melting temperature of the primers and substrate DNA or RNA do not need to be added to the amplification reaction at a higher temperature using a thermostable RNA polymerase. As such, in some embodiments, amplification reactions (e.g., a NASBA or TMA reactions) that are done using a thermostable RNA polymerase may be done using a reaction mix that does not contain DMSO or a functional equivalent thereof (e.g, betaine, ethylene glycol and 1,2-propanediol, etc.)

In some embodiments, the RNA product (the product of an amplification reaction may be detected after it is amplified. This may be done, e.g., using a molecular beacon (see, e.g., Tyagi Nat. Biotechnol. 1996 14: 303-8, among others). Detection may be done quantitatively in some cases.

Examples of closely related bacteriophage RNA polymerases are provided below. Mutations identified for T7 RNA polymerase that improve thermostability and/or activity are expected to have a corresponding effect when positioned in closely related bacteriophage RNA polymerases in corresponding positions.

*Enterobacteria bacteriophage* 13a (SEQ ID NO: 52)

MNTINIAKNDFSDIELAAIPFNTLADHYGERLAREQLALEHESYEMGEARFRKMFERQLKAGEVADNAAAKPLITTLLPKMIARIN

DWFEEVKAKRGKRPTAFQFLQEIKPEAVAYITIKTTLACLTSVDNTTVQAVASAIGRAIEDEARFGRIRDLEAKHFKKNVEEQLNKR

VGHVYKKAFMQVVEADMLSKGLLGGEAWSSWHKEDSIHVGVRCIEMLIESTGMVSLHRQNAGVVGQDSETIELAPEYAEAIAT

RAGALAGISPMFQPCVVPPKPWTGITGGGYWANGRRPLALVRTHSKKALMRYEDVYMPEVYKAINIAQNTAWKINKKVLAVA

NVITKWKHCPVEDIPAIEREELPMKPEDIDTNPDALTAWKRAAAAVYRKDKARKSRRISLEFMLEQANKFANHKAIWFPYNMD

WRGRVYAVSMFNPQGNDMTKGLLTLAKGKPIGKEGYYWLKIHGANCAGVDKVPFPERIKFIEDNHENIMACAKSPLENTWWA

EQDSPFCFLAFCFEYAGVQHHGLSYNCSLPLAFDGSCSGIQHFSAMLLDEIGGRAVNLLPSETVQDIYGIVAKKVNVILQADVINGT

DNEVVTVTDENTGEISEKVKLGTKALAGQWLAYGVTRSVTKRSVMTLAYGSKEFGFRQQVLEDTIQPAIDSGKGLMFTQPNQAA

GYMAKLIWEAVSVTVVAAVEAMNWLKSAAKLLAAEVKDKKTGEILRKRCAVHWVTPDGFPVWQEYKKPIQTRLNLMFLGQFR

LQPTINTNKDSEIDAHKQESGIAPNFVHSQDGSHLRKTVVWAHEKYGIESFALIHDSFGTIPADAANLFKAVRETMVDTYESCDVL

ADFYDQFADQLHESQLDKMPALPAKGNLNLQDILKSDFAFA

*Yersinia bacteriophage* YpP-R (SEQ ID NO: 53)

MNTINIAKNDFSDIELAAIPFNTLADHYGERLAREQLALEHESYEMGEARFRKMFERQLKAGEVADNAAAKPLITTLLPKMIARIN

DWFEEVKAKRGKRPTAFQFLQEIKPEAVAYITIKTTLACLTSADNTTVQAVASAIGRAIEDEARFGRIRDLEAKHFKKNVEEQLNKR

VGHVYKKAFMQVVEADMLSKGLLGGEAWSSWHKEDSIHVGVRCIEMLIESTGMVNLHRQNAGVVGQDSETIELTPEYAEAIAT

RAGALAGISPMFQPCVVPPKPWTGITGGGYWANGRRPLALVRTHSKKALMRYEDVYMPEVYKAINIAQNTAWKINKKVLAVA

NVITKWKHCPVEDIPAIEREELPMKPEDIDTNPEALTAWKRAAAAVYRKDKARKSRRISLEFMLEQANKFANHKAIWFPYNMDW

RGRVYAVSMFNPQGNDMTKGLLTLAKGKPIGKEGYYWLKIHGANCAGVDKVPFPERIKFIEDNHENIMACAKSPLENTWWAE

QDSPFCFLAFCFEYAGVQHHGLSYNCSLPLAFDGSCSGIQHFSAMLLDEVGGLAVNLLPSATVQDIYGIVAKKVNVILQADVINGT

DNEVVTVTDENTGEISEKVKLGTKALAGQWLAYGVTRSVTKRSVMTLAYGSKEFGFRQQVLEDTIQPAIDSGKGLMFTQPNQAA

GYMAKLIWEAVSVTVVAAVEAMNWLKSAAKLLAAEVKDKKTGEILRKRCAVHWVTPDGFPVWQEYKKPIQTRLNLMFLGQFR

LQPTINTNKDSEIDAHKQESGIAPNFVHSQDGSHLRKTVVWAHEKYGIESFALIHDSFGTIPADAANLFKAVRETMVDTYESCDVL

ADFYDQFADQLHESQLDKMPALPAKGNLNLQDILKSDFAFA

-continued

*Yersinia* bacteriophage R (SEQ ID NO: 54)
MNTINIAKNDFSDIELAAIPFNTLADHYGERLAREQLALEHESYEMGEARFRKMFERQLKAGEVADNAAAKPLITTLLPKMIARIN
DWFEEVKAKRGKRPTAFQFLQEIKPEAVAYITIKTTLACLTSADNTTVQAVASAIGRAIEDEARFGRIRDLEAKHFKKNVEEQLNKR
VGHVYKKAFMQVVEADMLSKGLLGGEAWSSWHKEDSIHVGVRCIEMLIESTGMVNLHRQNAGVVGQDSETIELTPEYAEAIAT
RAGALAGISPMFQPCVVPPKPWTGITGGGYWANGRRPLALVRTHSKKALMRYEDVYMPEVYKAINIAQNTAWKINKKVLAVA
NVITKWKHCPVEDIPAIEREELPMKPEDIDTNPEALTAWKRAAAAVYRKDKARKSRRISLEFMLEQANKFANHKAIWFPYNMDW
RGRVYAVSMFNPQGNDMTKGLLTLAKGKPIGKEGYYWLKIHGANCAGVDKVPFPERIKFIEDNHENIMACAKSPLENTWWAE
QDSPFCFLAFCFEYAGVQHHGLSYNCSLPLAFDGSCSGIQHFSAMLLDEVGGLAVNLLPSATVQDIYGIVAKKVNVILQADVINGT
DNEVVTVTDENTGEIPEKVKLGTKALAGQWLAYGVTRSVTKRSVMTLAYGSKEFGFRQQVLEDTIQPAIDSGKGLMFTQPNQAA
GYMAKLIWEAVSVTVVAAVEAMNWLKSAAKLLAAEVKDKKTGEILRKRCAVHWVTPDGFPVWQEYKKPIQTRLNLMFLGQFR
LQPTINTNKDSEIDAHKQESGIAPNFVHSQDGSHLRKTVVWAHEKYGIESFALIHDSFGTIPADAANLFKAVRETMVDTYESCDVL
ADFYDQFADQLHESQLDKMPALPAKGNLNLQDILKSDFAFA

*Yersinia* bacteriophage phiA1122

(SEQ ID NO: 55)
MNTINIAKNDFSDIELAAIPFNTLADHYGERLAREQLALEHESYEMGEARFRKMFERQLKAGEVADNAAAKPLITTLLPKMIARIN
DWFEEVKAKRGKRPTAFQFLQEIKPEAVAYITIKTTLACLTSADNTTVQAVASAIGRAIEDEARFGRIRDLEAKHFKKNVEEQLNKR
VGHVYKKAFMQVVEADMLSKGLLGGEAWSSWHKEDSIHVGVRCIEMLIESTGMVNLHRQNAGVVGQDSETIELTPEYAEAIAT
RAGALAGISPMFQPCVVPPKPWTGITGGGYWANGRRPLALVRTHSKKALMRYEDVYMPEVYKAINIAQNTAWKINKKVLAVA
NVITKWKHCPVEDIPAIEREELPMKPEDIDTNPEALTAWKRAAAAVYRKDKARKSRRISLEFMLEQANKFANHKAIWFPYNMDW
RGRVYAVSMFNPQGNDMTKGLLTLAKGKPIGKEGYYWLKIHGANCAGVDKVPFPERIKFIEDNHENIMACAKSPLENTWWAE
QDSPFCFLAFCFEYAGVQHHGLSYNCSLPLAFDGSCSGIQHFSAMLLDEVGGLAVNLLPSATVQDIYGIVAKKVNVILQADVINGT
DNEVVTVTDENTGEIPEKVKLGTKALAGQWLAYGVTRSVTKRSVMTLAYGSKEFGFRQQVLEDTIQPAIDSGKGLMFTQPNQAA
GYMAKLIWEAVSVTVVAAVEAMNWLKSAAKLLAAEVKDKKTGEILRKRCAVHWVTPDGFPVWQEYKKPIQTRLNLMFLGQFR
LQPTINTNKDSEIDAHKQESGIAPNFVHSQDGSHLRKTVVWAHEKYGIESFALIHDSFGTIPADAANLFKAVRETMVDTYESCDVL
ADFYDQFADQLHESQLDKMPALPAKGNLNLQDILKSDFAFA

*Escherichia* bacteriophage CICC 80001

(SEQ ID NO: 56)
MNTINIAKNDFSDIELAAIPFNTLADHYGERLAREQLALEHESYEMGEARFRKMFERQLKAGEVADNAAAKPLITTLLPKMIARIN
DWFEVVKAKRGKRPTAFQFLQEIKPEAVAYITIKTTLACLTSADNTTVQAVASAIGRAIEDESRFGRIRDLEAKHFKKNVEEQLNKR
VGHVYRKAFMQVVEADMLSKGLMGGEAWSSWHKEDSIHVGVRCIEMLIESTGMVSLHRQNAGVVGQDSETIELAPEYAEAIA
TRAGALAGISPMFQPCVVPPKPWTGITGGGYWANGRRPLALVRTHSKKALMRYEDVYMPEVYKAINIAQNTAWKINKKVLAVA
NVITKWKHCPVEDIPAIEREELPMKPEDIDTNPEALTAWKRAAAAVYRKDKARKSRRISLEFMLEQANKFANHKSIWFPYNMDW
RGRVYAVSMFNPQGNDMTKGLLTLAKGKPIGKEGYYWLKIHGANCAGVDKVPFPERIKFIEDNHENIMACAKSPLENTWWAE
QDSPFCFLAFCFEYAGVQHHGLSYNCSLPLAFDGSCSGIQHFSAMLRDEVGGLAVNLLPSETVQDIYGIVAKKVNVILQEDVINGT
DNEVVTVTDENTGEISEKVKLGTKALAGQWLAYGVTRSVTKRSVMTLAYGSKEFGFRQQVLEDTIQPAIDSGKGLMFTQPNQAA
GYMAKLIWEAVSVTVVAAVEAMNWLKSAAKLLAAEVKDKKTGEILRKRCAVHWVTPDGFPVWQEYKKPIQTRLNLIFLGQFRL
QPTINTNKDSEIDAHKQESGIAPNFVHSQDGSHLRKTVVWAHEKYGIESFALIHDSFGTIPADAANLFKAVRETMVDTYESCDVLA
DFYDQFADQLHESQLDKMPALPAKGNLNLQDILKSDFAFA

*Yersinia* bacteriophage YpsP-G (SEQ ID NO: 57)
MTERTDGLKKGYMPNGTLYAANRRLVRTWRENNLELAAIPFNTLADHYGERLAREQLALEHESYEMGEARFRKMFERQLKAGE
VADNAAAKPLITTLLPKMIARINDWFEEVKAKRGKRPTAFQFLQEIKPEAVAYITIKTTLACLTSADNTTVQAVASAIGRAIEDEARF
GRIRDLEAKHFKKNVEEQLNKRVGHVYKKAFMQVVEADMLSKGLLGGEAWSSWHKEDSIHVGVRCIEMLIESTGMVNLHRQN -continued AGVVGQDSETIELTPEYAEAIATRAGALAGISPMFQPCVVPPKPWTGITGGGYWANGRRPLALVRTHSKKALMRYEDVYMPEVY KAINIAQNTAWKINKKVLAVANVITKWKHCPVEDIPAIEREELPMKPEDIDTNPEALTAWKRAAAAVYRKDKARKSRRISLEFMLE QANKFANHKAIWFPYNMDWRGRVYAVSMFNPQGNDMTKGLLTLAKGKPIGKEGYYWLKIHGANCAGVDKVPFPERIKFIEDN HENIMACAKSPLENTWWAEQDSPFCFLAFCFEYAGVQHHGLSYNCSLPLAFDGSCSGIQHFSAMLLDEVGGLAVNLLPSATVQD IYGIVAKKVNVILQADVINGTDNEVVTVTDENTGEISEKVKLGTKALAGQWLAYGVTRSVTKRSVMTLAYGSKEFGFRQQVLEDTI QPVIDSGKGLMFTQPNQAAGYMAKLIWEAVSVTVVAAVEAMNWLKSAAKLLAAEVKDKKTGE1LRKRCAVHWVTPDGFPVW QEYKKPIQTRLNLMFLGQFRLQPTINTNKDSEIDAHKQESGIAPNFVHSQDGSHLRKTVVWAHEKYGIESFALIHDSFGTIPADAA

NLFKAVRETMVDTYESCDVLADFYDQFADQLHESQLDKMPALPAKGNLNLQDILKSDFAFA

Salmonella bacteriophage Vi06

(SEQ ID NO: 58)

MNTISITKNDFSDIELAAIPFNTLADHYGERLAREQLALEHESYEMGEVRFRKMFERQLKAGEIADNDATKPLITTLLPKMIARINS

WPKEVQAKCGKRPTAFQFLQGIKPEAIAYITIKTTLARLTSMDNTTVQAVASAIGRAIEDEARFGRIRDLEAKHFKKNVEEQLNKRV

GHVYKKAFMQVIEADMLSKGLLGGESWSSWHKEDSIHVGVRCIEMLIESTGMVSLHRQNAGVVGQDSETIELAPEYAEAIATRA

GALAGISPMFQPCVVPPKPWTSISGGGYWANGRRPLALVRTHSKKALMRYADVYMPEVYKAVNIAQNTAWRINKKVLAVANV

VTKWKHCPVDYIPTIEREELPMKPEDIDTNPEALASWKRAAAAVYRKDKARKSRRMSLEFMLEQANKFANHRAIWFPYNMDW

RGRVYAVSMFNPQGNDMTKGLLTLAKGKPIGKEGFYWLKIHGANCAGVDKVPFPERIKFIEDNHENILACAKSPLENTWWSEQ

DSPFCFLAFCFEYAGGQHHGLSYNCSLPLAFDGSCFGIQHFSVMLRDEVGGRAVNLLPSETVQDIYGIVAKKVNEILQVDMINGT

DNEVVTVTDDKTGEIYEKIKLGTKELAGQWLAYGVTRSVTKRSVMTLAYGSKEFGFRQQVLEDTIQPAIDSGKGLMFTHPNQAA

GYMAKLIWEAVSVTVVAAVEAMNWLKSAAKLLAVEVKDRKTGE1LRKRCAVHWTTPDGFPVWQEYKKPVQTRLNLIFLGQFRL

QPTINTNRDSEIDAYKQESGIAPNFVHSQDGSHLRKTVVWAHEKYGIDSFALIHDSFGTIPADAANLFKAVRETMVATYESCDVLA

DFYAQFADQLHKSQLDKMPVLPSKGNLNLQDILKSDFAFA

Stenotrophomonas bacteriophage IME15

(SEQ ID NO: 59)

MTVIAIEKNDFSDVELAVIPFNTLADHYGEKLAREQLALEHEAYEMGEARFRKIFERQLKAGEVADNAAAKPLVATLLPKMIERIHA

WFEEVSAKRGKRPTAFKFLQEVKPEAIAYITIKTVLGTLTSAEQTTVQAAASAVGRAIEDEARFGRIRDLEAKHFKKNVEEQLNKRV

GHVYKKAFLQVVEADMLSKGLMGGEAWSSWHKEDSIHVGVRCIEMLIEATGLVVLERQNAGVVGADAETLSLASEYADAIATR

AGALAGISPMYQPCVVPPKPWTTVTGGGWVANGRRPLALVRTHGKKALMRYEDVYMPEVYKAVNLAQSTAWKINKKVLAVA

NEITKWKHCPVEDIPAIEREELPVKPDDIDENPEALTNWKRAAAAVYRKDKARKSRRLSLEFMLEQANKFANHKAIWFPYNMDW

RGRVYAVSMFNPQGNDMTKGLLTLAKGKAIGKEGFYWLKIHGANCAGVDKVPFPERIKFIEDNHEHIMASAKNPLEYTWWAE

QDSPFCFLAFCFEYAGVMHHGLSYNCSLPLAFDGSCSGIQHFSAMLRDEVGGRAVNLLPSETVQDIYGIVAKKVNEIMQRDVISG

TDDELVTETDKTTGEITEKAVLGTRTLAGQWLAYGANRSVTKRSVMTLAYGSKEFGFRQQVLEDTIRPAIDSGKGLMFTIPNQAA

GYMAKLIWDSVSVTVVAAVEAMKWLQSAAKLLAAEVKDKKTGEVLRNRCAVHWVTPDGFPVWQEYRKPLQTRLNLMFLGQF

RLQPTINTNKDSGIDAHKQESGIAPNFVHSQDGSHLRKTVVWAHEKYGIESFALIHDSFGTIPADAGNLFKAVRETMVDTYENCD

VLADFYEQFADQLHESQLDKMPALPKKGNLNLRDILESDFAFA

Citrobacter bacteriophage SH2

(SEQ ID NO: 60)

MNIIENIEKNDFSEIELAAIPFNTLADHYGSALAREQLALEHESYELGERRFLKMLERQAKAGEIADNAAAKPLLATLLPKLTARIVE

WLEEYASKKGRKPVAYAPLQLLKPEASAFITLKVILASLTSTNMTTIQAAAGMLGKAIEDEARFGRIRDLEAKHFKKHVEEQLNKRH

GQVYKKAFMQVVEADMIGRGLLGGEAWSSWDKETTMHVGIRLIEMLIESTGLVELQRHNAGNAGSDHEALQLAQEYVDVLAK

RAGALAGISPMFQPCVVPPKPWVSITGGGYWANGRRPLALVRTHSKKGLMRYEDVYMPEVYKAVNIAQNTAWKINKKVLAVV

NEIVNWKNCPVADIPSLERQELPPKPDDIDTNEAALKEWKKAAAGVYRLDKARVSRRISLEFMLEQANKFANKKAIWFPYNMD

WRGRVYAVPMFNPQGNDMTKGLLTLAKGKPIGEEGFYWLKIHGANCAGVDKVPFPERIAFIEKHVDDILACAKDPINNTWWAE

QDSPFCFLAFCFEYAGVAHHGLSYNCSLPLAFDGSCSGIQHFSAMLRDEVGGRAVNLLPSETVQDIYGIVAQKVNEILKQDAINGT

PNEMITVTDKDTGEISEKLKLGTSTLAQQWLAYGVTRSVTKRSVMTLAYGSKEFGFRQQVLDDTIQPAIDSGKGLMFTQPNQAA

GYMAKLIWDAVSVTVVAAVEAMNWLKSAAKLLAAEVKDKKTKEILRHRCAVHWTTPDGFPVWQEYRKPLQKRLDMIFLGQFR

LQPTINTLKDSGIDAHKQESGIAPNFVHSQDGSHLRMTVVYAHEKYGIESFALIHDSFGTIPADAGKLFKAVRETMVITYENNDVL

ADFYDQFADQLHETQLDKMPPLPKKGNLNLQDILKSDFAFA

Enterobacter bacteriophage E-4

(SEQ ID NO: 61)

MNIIENIEKNDFSEIELAAIPFNTLADHYGSALAREQLALEHESYELGERRFLKMLERQAKAGEIADNAAAKPLLATLLPKLTARIVE

WLEEYASKKGRKPSAYAPLQLLKPEASAFITLKVILASLTSTNMTTIQAAAGMLGKAIEDEARFGRIRDLEAKHFKKHVEEQLNKRH

GQVYKKAFMQVVEADMIGRGLLGGEAWSSWDKETTMHVGIRLIEMLIESTGLVELQRHNAGNAGSDHEALQLAQEYVDVLAK

RAGALAGISPMFQPCVVPPKPWVSITGGGYWANGRRPLALVRTHSKKGLMRYEDVYMPEVYKAVNIAQNTAWKINKKVLAVV

NEIVNWKNCPVADIPSLERQELPPKPDDIDTNEAALKEWKKAAAGIYRLDKARVSRRISLEFMLEQANKFANKKAIWFPYNMDW

RGRVYAVPMFNPQGNDMTKGLLTLAKGKPIGEEGFYWLKIHGANCAGVDKVPFPERIAFIEKHVDDILACAKDPINNTWWAEQ

DSPFCFLAFCFEYAGVAHHGLSYNCSLPLAFDGSCSGIQHFSAMLRDEVGGRAVNLLPSETVQDIYGIVAQKVNEILKQDAINGTP

NEMITVTDKDTGEISEKLKLGTSTLAQQWLAYGVTRSVTKRSVMTLAYGSKEFGFRQQVLDDTIQPAIDSGKGLMFTQPNQAAG

YMAKLIWDAVSVTVVAAVEAMNWLKSAAKLLAAEVKDKKTKEILRHRCAVHWTTPDGFPVWQEYRKPLQKRLDMIFLGQFRL

QPTINTLKDSGIDAHKQESGIAPNFVHSQDGSHLRMTVVYAHEKYGIESFALIHDSFGTIPADAGKLFKAVRETMVLTYENNDVLA

DFYDQFADQLHETQLDKMPPLPKKGNLNLQDILKSDFAFA

Yersinia bacteriophage phiYe-F10

(SEQ ID NO: 62)

MNIIENIEKNDFSEIELAAIPFNTLADHYGSALAREQLALEHESYELGERRFLKMLERQAKAGEIADNAAAKPLLATLLPKLTARIVE

WLEEYASKKGRKPVAYAPLQSLKPEASAFITLKVILASLTSTNMTTIQAAAGMLGKAIEDEARFGRIRDLEAKHFKKHVEEQLNKRH

GQVYKKAFMQVVEADMIGRGLLGGEAWSSWDKETTMHVGIRLIEMLIESTGLVELQRHNAGNAGSDHEALQLAQEYVDVLAK

RAGALAGISPMFQPCVVPPKPWVSITGGGYWANGRRPLALIRTHSKKGLMRYEDVYMPEVYKAVNIAQNTAWKINKKVLAVV

NEIVNWKNCPVADIPSLERQELPPKPDDIDTNEAALKEWKKAAAGVYRLDKARVSRRISLEFMLEQANKFASKKAIWFPYNMDW

RGRVYAVPMFNPQGNDMTKGLLTLAKGKPIGEEGFYWLKIHGANCAGVDKVPFPERIAFIEKHVDDILACAKDPINNTWWAEQ

DSPFCFLAFCFEYAGVAHHGLSYNCSLPLAFDGSCSGIQHFSAMLRDEVGGRAVNLLPSETVQDIYGIVAQKVNEILKQDAINGTP

NEMITVTDKDTGEISEKLKLGTSTLAQQWLAYGVTRSVTKRSVMTLAYGSKEFGFRQQVLDDTIQPAIDSGKGLMFTQPNQAAG

YMAKLIWDAVSVTVVAAVEAMNWLKSAAKLLAAEVKDKKTKEILRHRCAVHWTTPDGFPVWQEYRKPLQKRLDMIFLGQFRL

QPTINTLKDSGIDAHKQESGIAPNFVHSQDGSHLRMTVVYAHEKYGIESFALIHDSFGTIPADAGKLFKAVRETMVITYENNDVLA

DFYDQFADQLHETQLDKMPPLPKKGNLNLQDILKSDFAFA

Citrobacter bacteriophage phiCFP-1

(SEQ ID NO: 63)

MNIIENIEKNDFSEIELAAIPFNTLADHYGSALAREQLALEHESYELGERRFLKMLERQAKAGEIADNAAAKPLLATLLPKLTARIVE

WLEEYDSKKGRKPVAYAPLQLLKPEASAFITLKVILASLTSTNMTTIQAAAGMLGKAIEDEARFGRIRDLEAKHFKKHVEEQLNKRH

GQVYKKAFMQVVEADMIGRGLLGGEAWSSWDKETTMHVGIRLIEMLIESTGLVELQRHNAGNAGSDHEALQLAQEYVDVLAK

RAGALAGISPMFQPCVVPPKPWVAITGGGYWANGRRPLALVRTHSKKGLMRYEDVYMPEVYKAVNIAQNTAWKINKKVLAVV

NEIVNWKNCPVADIPSLERQELPPKPDDIDTNEAALKEWKKAAAGIYRLDKARVSRRISLEFMLEQANKFASKKAIWFPYNMDW

RGRVYAVPMFNPQGNDMTKGLLTLAKGKPIGEEGFYWLKIHGANCAGVDKVPFPERIAFIEKHVDDILACAKDPINNTWWAEQ

DSPFCFLAFCFEYAGVAHHGLSYNCSLPLAFDGSCSGIQHFSAMLRDEVGGRAVNLLPSETVQDIYGIVAQKVNEILKQDAINGTP

NEMITVTDKDTGEISEKLKLGTSTLAQQWLAYGVTRSVTKRSVMTLAYGSKEFGFRQQVLDDTIQPAIDSGKGLMFTQPNQAAG

YMAKLIWDAVSVTVVAAVEAMNWLKSAAKLLAAEVKDKKTKEILRHRCAVHWTTPDGFPVWQEYRKPLQKRLDMIFLGQFRL

QPTINTLKDSGIDAHKQESGIAPNFVHSQDGSHLRMTVVYAHEKYGIESFALIHDSFGTIPADAGKLFKAVRETMVITYENNDVLA

DFYDQFADQLHETQLDKMPPLPKKGNLNLQDILKSDFAFA

-continued

```
Citrobacter bacteriophage SH1
                                                           (SEQ ID NO: 64)
MNIIENIEKNDFSEIELAAIPFNTLADHYGSALAREQLALEHESYELGERRFLKMLERQAKAGEIADNAAAKPLLATLLPKLTARIVE WLEEYASKKGRKPVAYAPLQLLKPEASAFITLKVILASLTSTNMTTIQAAAGMLGKAIEDEARFGRIRDLEAKHFKKHVEEQLNKRH GQVYKKAFMQVVEADMIGRGLLGGEAWSSWDKETTMHVGIRLIEMLIESTGLVELQRHNAGNAGSDHEALQLAQEYVDVLAK RAGALAGISPMFQPCVVPPKPWVSITGGGYWANGRRPLALVRTHSKKGLMRYEDVYMPEVYKAVNIAQNTAWKINKKVLAVV NEIVNWKNCPVADIPSLERQELPPKPDDIDTNEAALKEWKKAAAGIYRLDKARVSRRISLEFMLEQANKFASKKAIWFPYNMDW RGRVYAVPMFNPQGNDMTKGLLTLAKGKPIGEEGFYWLKIHGANCAGVDKVPFPERIAFIEKHVDDILACAKDPINNTWWAEQ DSPFCFLAFCFEYAGVAHHGLSYNCSLPLAFDGSCSGIQHFSAMLRDEVGGRAVNLLPSETVQDIYGIVAQKVNEILKQDAINGTP NEMITVTDKDTGEISEKLKLGTSTLAQQWLAYGVTRSVTKRSVMTLAYGSKEFGFRQQVLDDTIQPAIDSGKGLMFTQPNQAAG YMAKLIWDAVSVTVVAAVEAMNWLKSAAKLLADEVKDKKTKEILRHRCAVHWTTPDGFPVWQEYRKPLQKRLDMlFLGQFRL QPTINTLKDSGIDAHKQESGIAPNFVHSQDGSHLRMTVVYAHEKYGIESFALIHDSFGTIPADAGKLFKAVRETMVITYENNDVLA

DFYDQFADQLHETQLDKMPPLPKKGNLNLQDILKSDFAFA

Salmonella bacteriophage phiSG-JL2
                                                           (SEQ ID NO: 65)
MNIIENIEKNDFSEIELAAIPFNTLADHYGSALAREQLALEHESYELGERRFLKMLERQAKAGEIADNAAAKPLLATLLPKLTARIVE WLEEYASKKGRKPVAYAPLQLLKPEASAFITLKVILASLTSTNMTTIQAAAGMLGKAIEDEARFGRIRDLEAKHFKKHVEEQLNKRH GQVYKKAFMQVVEADMIGRGLLGGEAWSSWDKETTMHVGIRLIEMLIESTGLVELQRHNAGNAGSDHEALQLAQEYVDVLAK RAGALAGISPMFQPCVVPPKPWVAITGGGYWANGRRPLALVRTHSKKGLMRYEDVYMPEVYKAVNIAQNTAWKINKKVLAVV NEIVNWKNCPVADIPSLERQELPPKPDDIDTNEAALKEWKKAAAGVYRLDKARVSRRISLEFMLEQANKFASKKAIWFPYNMDW RGRVYAVPMFNPQGNDMTKGLLTLAKGKPIGEEGFYWLKIHGANCAGVDKVPFPERIAFIEKHVDDILACAKDPINNTWWAEQ DSPFCFLAFCFEYAGVAHHGLSYNCSLPLAFDGSCSGIQHFSAMLRDEVGGRAVNLLPSETVQDIYGIVAQKVNEILKQDAINGTP NEMITVTDKDTGEISEKLKLGTSTLAQQWLAYGVTRSVTKRSVMTLAYGSKEFGFRQQVLDDTIQPAIDSGKGLMFTQPNQAAG YMAKLIWDAVSVTVVAAVEAMNWLKSAAKLLAAEVKDKKTKEILRHRCAVHWTTPDGFPVWQEYRKPLQKRLDMIFLGQFRL QPTINTLKDSGIDAHKQESGIAPNFVHSQDGSHLRMTVVYAHEKYGIESFALIHDSFGTIPADAGKLFKAVRETMVLTYENNDVLA

DFYDQFADQLHETQLDKMPPLPKKGKLNLQDILKSDFAFA

Yersinia bacteriophage phiYeO3-12
                                                           (SEQ ID NO: 66)
MNIIENIEKNDFSEIELAAIPFNTLADHYGSALAREQLALEHESYELGERRFLKMLERQAKAGEIADNAAAKPLLATLLPKLTTRIVE WLEEYATKKGRKPVAYAPLQSLKPEASAFITLKVILASLTSTNMTTIQAAAGMLGKAIEDEARFGRIRDLEAKHFKKHVEEQLNKRH GQVYKKAFMQVVEADMIGRGLLGGEAWSSWDKETTMHVGIRLIEMLIESTGLVELQRHNAGNAGSDHEALQLAQEYVDVLAK RAGALAGISPMFQPCVVPPKPWVAITGGGYWANGRRPLALVRTHSKKGLMRYEDVYMPEVYKAVNIAQNTAWKINKKVLAVV NEIVNWKNCPVADIPSLERQELPPKPDDIDTNEAALKEWKKAAAGIYRLDKARVSRRISLEFMLEQANKFASKKAIWFPYNMDW RGRVYAVPMFNPQGNDMTKGLLTLAKGKPIGEEGFYWLKIHGANCAGVDKVPFPERIAFIEKHVDDILACAKDPINNTWWAEQ DSPFCFLAFCFEYAGVAHHGLSYNCSLPLAFDGSCSGIQHFSAMLRDEVGGRAVNLLPSETVQDIYGIVAQKVNEILKQDAINGTP NEMITVTDKDTGEISEKLKLGTSTLAQQWLAYGVTRSVTKRSVMTLAYGSKEFGFRQQVLDDTIQPAIDSGKGLMFTQPNQAAG YMAKLIWDAVSVTVVAAVEAMNWLKSAAKLLAAEVKDKKTKEILRHRCAVHWTTPDGFPVWQEYRKPLQKRLDMIFLGQFRL QPTINTLKDSGIDAHKQESGIAPNFVHSQDGSHLRMTVVYAHENYGIESFALIHDSFGTIPADAGKLFKAVRETMVITYENNDVLA

DFYDQFADQLHETQLDKMPPLPKKGNLNLQDILKSDFAFA

Enterobacteria bacteriophage T7M
                                                           (SEQ ID NO: 67)
MNIIENIEKNDFSEIELAAIPFNTLADHYGSALAKEQLALEHESYELGERRFLKMLERQAKAGEIADNAAAKPLLATLLPKLTTRIVE WLEEYASKKGRKPSAYAPLQLLKPEASAFITLKVILASLTSTNMTTIQAAAGMLGKAIEDEARFGRIRDLEAKHFKKHVEEQLNKRH GQVYKKAFMQVVEADMIGRGLLGGEAWSSWDKETTMHVGIRLIEMLIESTGLVELQRHNAGNAGSDHEALQLAQEYVDVLAK
```

-continued

RAGALAGISPMFQPCVVPPKPWVAITGGGYWANGRRPLALVRTHSKKGLMRYEDVYMPEVYKAVNLAQNTAWKINKKVLAV

VNEIVNWKNCPVADIPSLERQELPPKPDDIDTNEAALKEWKKAAAGIYRLDKARVSRRISLEFMLEQANKFASKKAIWFPYNMD

WRGRVYAVPMFNPQGNDMTKGLLTLAKGKPIGEEGFYWLKIHGANCAGVDKVPFPERIAFIEKHVDDILACAKDPINNTWWAE

QDSPFCFLAFCFEYAGVTHHGLSYNCSLPLAFDGSCSGIQHFSAMLRDEVGGRAVNLLPSETVQDIYGIVAQKVNEILKQDAINGT

PNEMITVTDKDTGEISEKLKLGTSTLAQQWLAYGVTRSVTKRSVMTLAYGSKEFGFRQQVLDDTIQPAIDSGKGLMFTQPNQAA

GYMAKLIWDAVSVTVVAAVEAMNWLKSAAKLLAAEVKDKKTKEILRHRCAVHWTTPDGFPVWQEYRKPLQKRLDMIFLGQFR

LQPTINTLKDSGIDAHKQESGIAPNFVHSQDGSHLRMTVVYAHEKYGIESFALIHDSFGTIPADAGKLFKAVRETMVITYENNDVL

ADFYSQFADQLHETQLDKMPPLPKKGNLNLQDILKSDFAFA

Enterobacteria bacteriophage T3

(SEQ ID NO: 68)

MNIIENIEKNDFSEIELAAIPFNTLADHYGSALAKEQLALEHESYELGERRFLKMLERQAKAGEIADNAAAKPLLATLLPKLTTRIVE

WLEEYASKKGRKPSAYAPLQLLKPEASAFITLKVILASLTSTNMTTIQAAAGMLGKAIEDEARFGRIRDLEAKHFKKHVEEQLNKRH

GQVYKKAFMQVVEADMIGRGLLGGEAWSSWDKETTMHVGIRLIEMLIESTGLVELQRHNAGNAGSDHEALQLAQEYVDVLAK

RAGALAGISPMFQPCVVPPKPWVAITGGGYWANGRRPLALVRTHSKKGLMRYEDVYMPEVYKAVNLAQNTAWKINKKVLAV

VNEIVNWKNCPVADIPSLERQELPPKPDDIDTNEAALKEWKKAAAGIYRLDKARVSRRISLEFMLEQANKFASKKAIWFPYNMD

WRGRVYAVPMFNPQGNDMTKGLLTLAKGKPIGEEGFYWLKIHGANCAGVDKVPFPERIAFIEKHVDDILACAKDPINNTWWAE

QDSPFCFLAFCFEYAGVTHHGLSYNCSLPLAFDGSCSGIQHFSAMLRDEVGGRAVNLLPSETVQDIYGIVAQKVNEILKQDAINGT

PNEMITVTDKDTGEISEKLKLGTSTLAQQWLAYGVTRSVTKRSVMTLAYGSKEFGFRQQVLDDTIQPAIDSGKGLMFTQPNQAA

GYMAKLIWDAVSVTVVAAVEAMNWLKSAAKLLAAEVKDKKTKEILRHRCAVHWTTPDGFPVWQEYRKPLQKRLDMIFLGQFR

LQPTINTLKDSGIDAHKQESGIAPNFVHSQDGSHLRMTVVYAHEKYGIESFALIHDSFGTIPADAGKLFKAVRETMVITYENNDVL

ADFYSQFADQLHETQLDKMPPLPKKGNLNLQDILKSDFAFA

Phage RNA polymerase (SEQ ID NO: 69)

MNIINIAKNDFSDIELAAIPFNILADHYGAQLAREQLALEHEAYEEGEKRFLKMLERQIKAGEFADNAAAKPLLSTLLPKLIARINDW

FEEVAAKRGKKPVAYNPLQHVKPEAAAFITLKVTLACLTKAEFTTIQAVASAIGRAIEDEARFGRIRDLEAKHFKKHVEEQLNKRVG

HVYKKAFMQVVEADMLSKGLLGGEAWSSWTKEESIHVGVRMLELLIESTGLVELHRPNAGNVGKDVEMIQLAPEYVDLLAKRA

GALAGISPMYQPCVVPPKPWTSIVGGGYWANGRRPLALVRTHSKKALMRYEDVYMPEVYKAVNIAQNTPWKINKKVLAVVNEI

VNWKHCPVADVPAIEREELPPKPEDIDTNEAALKAWKKAAAAIYRKDKARVSRRLSMEFMLEQANKFANFKAIWFPYNMDWR

GRVYAVPMFNPQGNDMTKGLLTLAKGKPIGKDGFYWLKIHGANCAGVDKVPFPERIKFIEDNHENIMACAKDPLNNEWWAEQ

DSPFCFLAFCFEYAGVQHHGLSYNCSLPLAFDGSCSGIQHFSAMLRDEIGGRAVNLLPSETVQDIYGIVADKVNEILKQDAINGTD

NEVETVTDKDTGEITEKLKLGTKELAGQWLAYGVTRKVTKRSVMTLAYGSKEFGFRQQVLEDTIQPAIDSGKGLMFTQPNQAAG

YMAKLIWEAVSVTVVAAVEAMNWLKSAAKLLAAEVKDKKTKEVLRKRCAVHWVTPDGFPVWQEYRKPVQTRLNLMFLGQFRL

QPTINTNKDSEIDAHKQESGIAPNFVHSQDGSHLRMTVVAHEKYGIESFALIHDSFGTIPADAGNLFKAVRETMVNTYEDNDVL

ADFYDQFADQLHESQLDKMPALPAKGNLNLQDILKSDFAFA

Phage RNA polymerase (SEQ ID No: 70)

MNTINIAKNDFSDIELAAIPFNTLADHYGERLAREQLALEHESYEMGEKRFLKMLERQVKAGEIADNAAAKPLITTLLPKLTARIND

WFEEVAAKRGKRPVAYQPLQGIKPEAVAFITIKVVLASLTSADNTTIQAVASAIGRAIEDEARFGRIRDLEAKHFKKHVEEQLNKRV

GHVYKKAFMQVVEADMLSKGLLGGEAWSSWNKEESMHVGIRMIEMLIESTGLVELHRHNAGVVGQDSETIQLAPEYVEALAK

RAGALAGISPMFQPCVVPPKPWVSITGGGYWANGRRPLALVRTHSKKALMRYEDVYMPEVYKAVNIAQNTAWKINKKVLAVV

NEIVNWKHCPVEDIPAIEREELPPKPDDIDTNEEALKAWKKAAAAVYRKDKARKSRRISLEFMLEQANKFANHKAIWFPYNMDW

RGRVYAVPMFNPQGNDMTKGLLTLAKGKPIGKEGFYWLKIHGANCAGVDKVPFPERIKFIEDNHDNIMACAKDPLDNTWWAE

QDSPFCFLAFCFEYAGVQHHGLSYNCSLPLAFDGSCSGIQHFSAMLRDEVGGRAVNLLPSETVQDIYGIVADKVNEILKQDVINGT

DNEVVTVTDKDTGEISEKLKLGTKELAQQWLAYGVTRSVTKRSVMTLAYGSKEFGFRQQVLEDTIQPAIDSGKGLMFTQPNQAA

-continued

```
GYMAKLIWDAVSVTVVAAVEAMNWLKSAAKLLAAEVKDKKTKEILRKRCAVHWVTPDGFPVWQEYRKPIQTRLNLMFLGQFR

LQPTINTNKDSEIDAHKQESGIAPNFVHSQDGSHLRMTVVYAHEKYGIESFALIHDSFGTIPADAGNLFKAVRETMVNTYENNDV

LADFYDQFADQLHESQLDKMPALPAKGNLNLQDILKSDFAFA
```

EXAMPLES

Example 1: Initial Screening Assays

Structure-based calculations were carried out to predict effect of mutations on thermal stability of T7 RNA polymerase. Mutations were modeled and evaluated using BioLuminate™ software (Schrödinger, New York, N.Y.) starting with the crystal structure of the wild-type T7 RNA polymerase (PDB ID: 1MSW). The predicted change in protein thermal stability upon mutation ($\Delta\Delta G$) was used to choose the candidate mutations. Mutations predicted to be stabilizing were introduced into wild type T7 RNA polymerase using site-directed mutagenesis using the Q5® Site-Directed Mutagenesis Kit (New England Biolabs, Ipswich, Mass.) and manufacturer's recommended protocols.

Figure 1B:
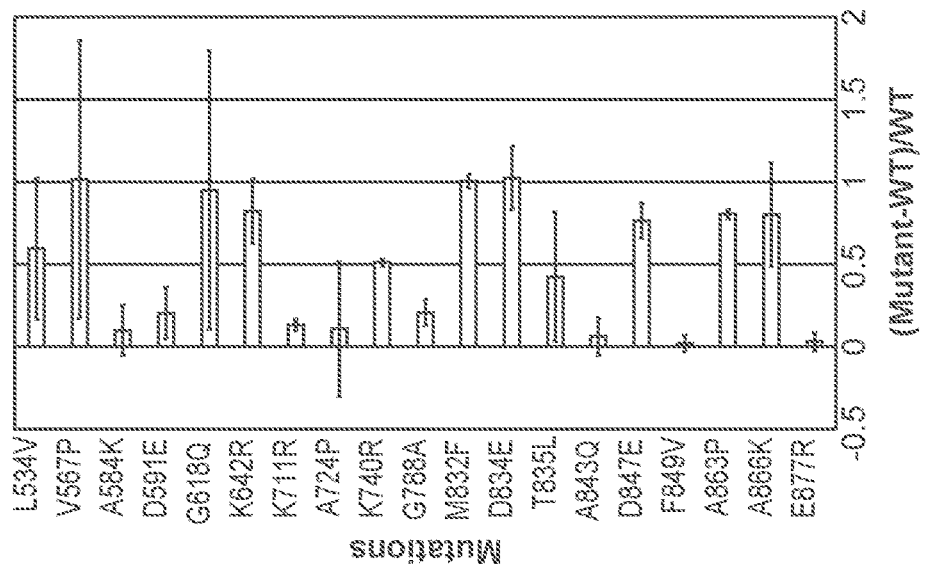
Figure 1A:
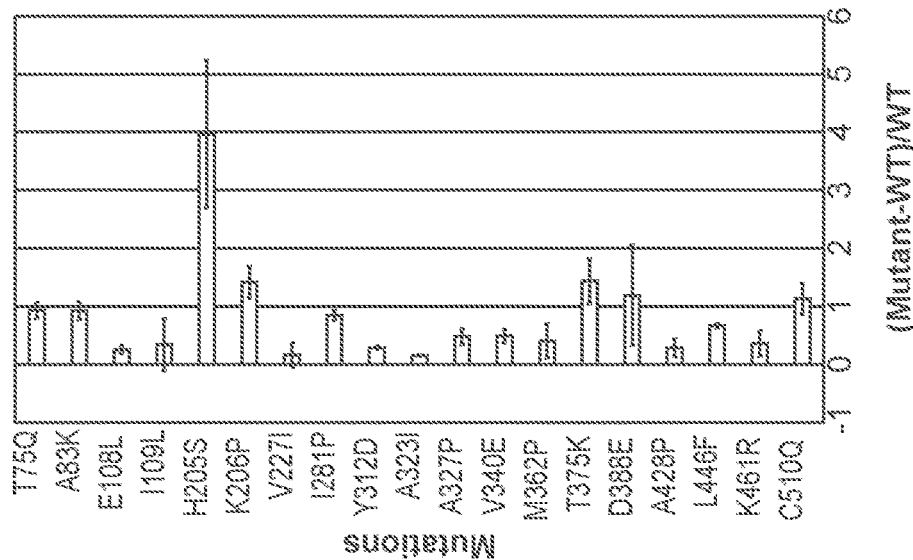
Figure 1D:
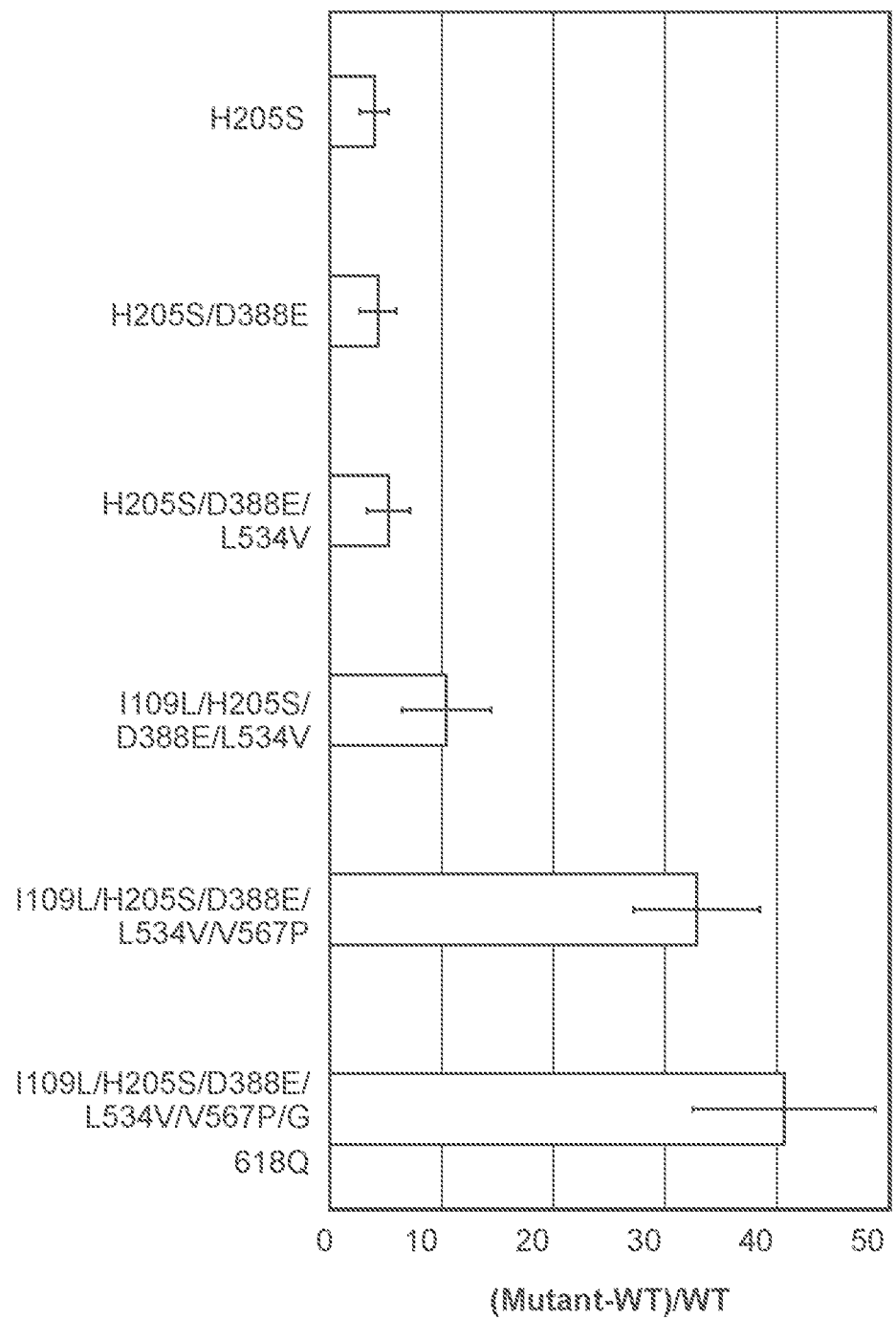

Individual mutations (see for example those in FIGS. 1A-1D) were screened in a novel cell-free assay based on the reconstituted translation system from *Thermus thermophilus* (Tth PURE system). Reconstitution of translation from *Thermus thermophilus* reveals a minimal set of components sufficient for protein synthesis at high temperatures and functional conservation of modern and ancient translation components (Zhou, et al., Nucleic Acids Research, 40(16), 7932-7945 (2012)). Genes encoding T7 RNAP variants were transcribed in vitro using SP6 RNA polymerase. 1 µl of in vitro transcription reaction was added to 10 µl of Tth PURE system with a fluorescent reporter gene (a GFP variant under the control of a T7 RNAP promoter). The activity of T7 RNA polymerase variants synthesized in Tth PURE system was coupled to the expression of a GFP gene under the control of a T7 promoter. All reactions were incubated at a range of temperatures for 10 hours. Transcription was monitored by production of a fluorescent signal in real time using a CFX96 Touch™ Real-Time PCR Detection System (Bio-Rad, Hercules, Calif.). FIG. 1A-1C show data for selected individual variants incubated at 45° C. for 10 hours (FIGS. 1A and 1B) and at 37° C. for 2 hours followed by 45° C. for 8 hours (FIG. 1C). FIG. 1D shows data for selected combinations of mutations. The reaction was carried out at 45° C. for 10 hours. All variants shown have a detectable increase in thermostability.

Example 2: Melting Temperature and Temperature Dependence Analysis

A. Selected T7 RNA polymerase variants (including those described in FIGS. 3A-3C, and FIGS. 4-6) contained an N-terminal hexahistidine tag and were expressed in *E. coli* and purified using nickel affinity chromatography using an ÄKTAFPLC® system (GE Life Sciences, Marlborough, Mass.). The hexahistidine-tagged polymerase variants were isolated and purified on nickel resin, eluted from the nickel resin with imidazole and dialyzed into a storage buffer (for example: 50 mM Tris-HCl pH 7.5, 100 mM NaCl, 10 mM DTT, 50% Glycerol, 0.1% Triton X-100).

Figure 2:
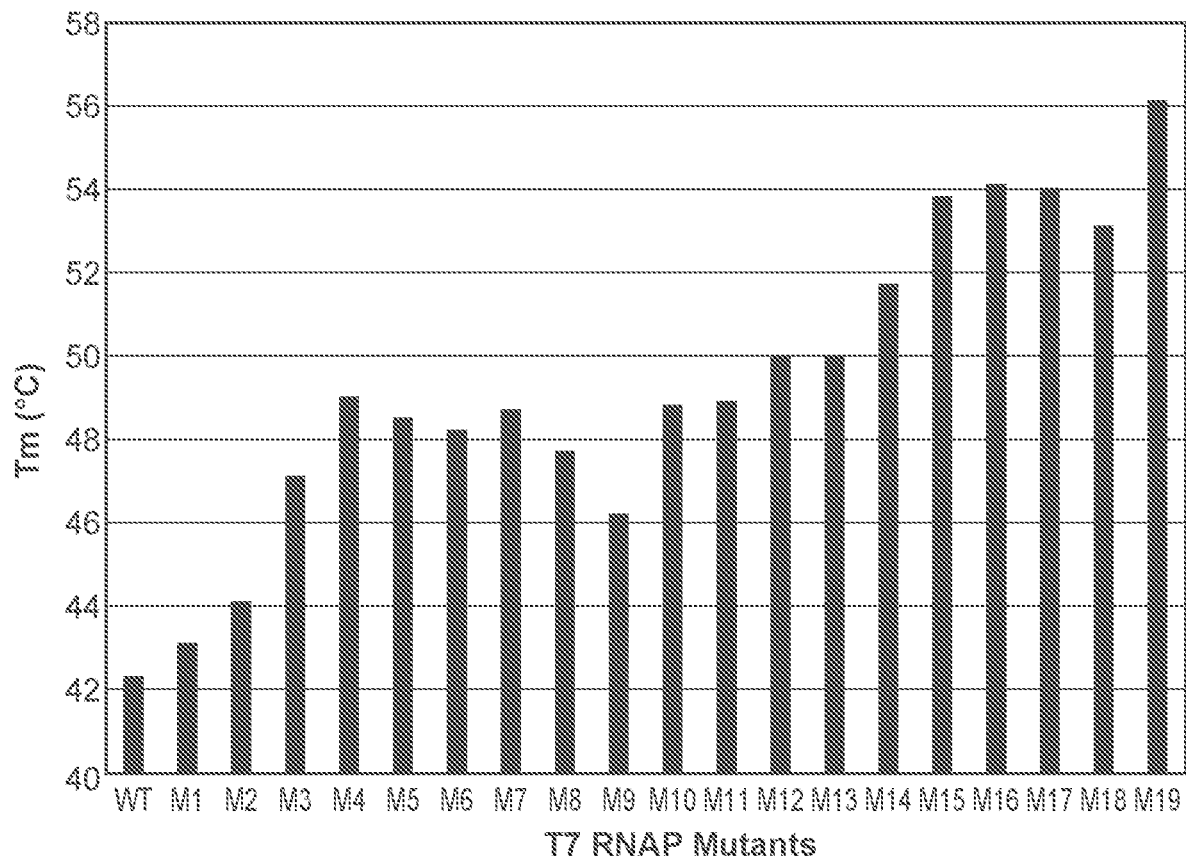
FIG. 2 shows the melting temperature of wild type T7 RNA polymerase (WT), as well various variants of the same (i.e., M1, M2, M3b, M4, M5, etc.). In this graph, the number after the M corresponds to the number of amino acid substitutions in the polymerase. For example, M5 has five amino acid substitutions relative to wild type T7 RNA polymerase, etc. This data shows that the effect of amino acid substitutions on melting temperature is largely additive.

B. To measure the melting temperature of the mutants (as shown in FIG. 2), 0.2 mg/ml T7 RNA polymerase variants were prepared in a buffer (50 mM Hepes-KOH, pH 8.0, 10 mM $Mg(OAc)_2$, 5 mM DTT, 2 mM spermidine). Melting temperatures were measured using Prometheus NT.48 (NanoTemper Technologies).

Figure 3A:
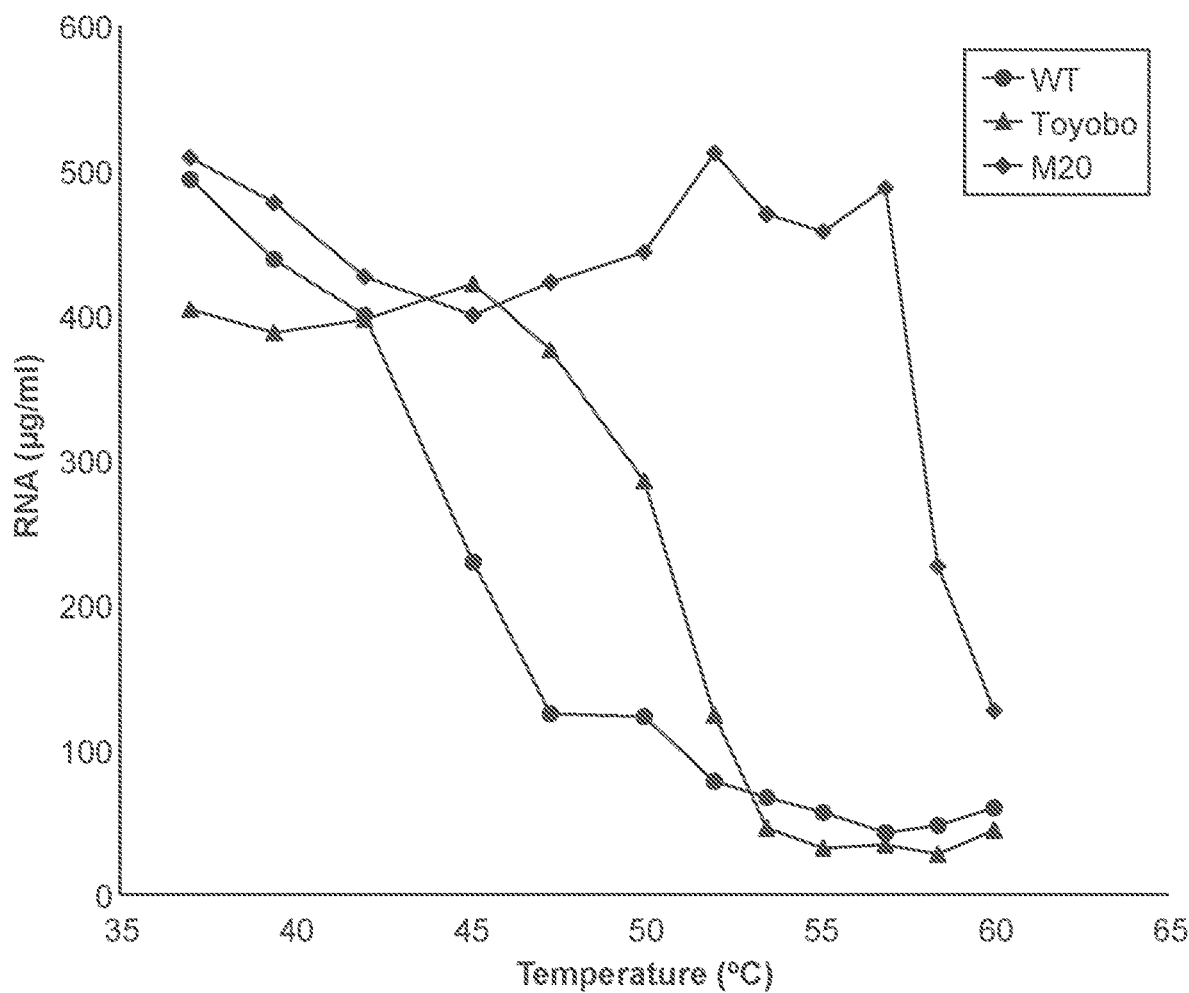
FIGS. 3A-3C show that (i) mutant RNA polymerases at temperatures above about 45° C. make more RNA compared to the corresponding wild type; (ii) mutant RNA polymerases at temperatures in the range of 50° C. to 55° C. can make at least 2 fold more RNA than the corresponding wild type RNA polymerase; and (iii) fusion proteins containing RNA polymerase and a DNA binding domain are more active at high temperatures than the corresponding wild type RNA polymerase; and (iv) fusion proteins containing RNA polymerase and a DNA binding domain show prolonged activity with a more gradual loss of activity at temperatures above 56° C. compared to the same RNA polymerase variant alone.
Figure 3B:
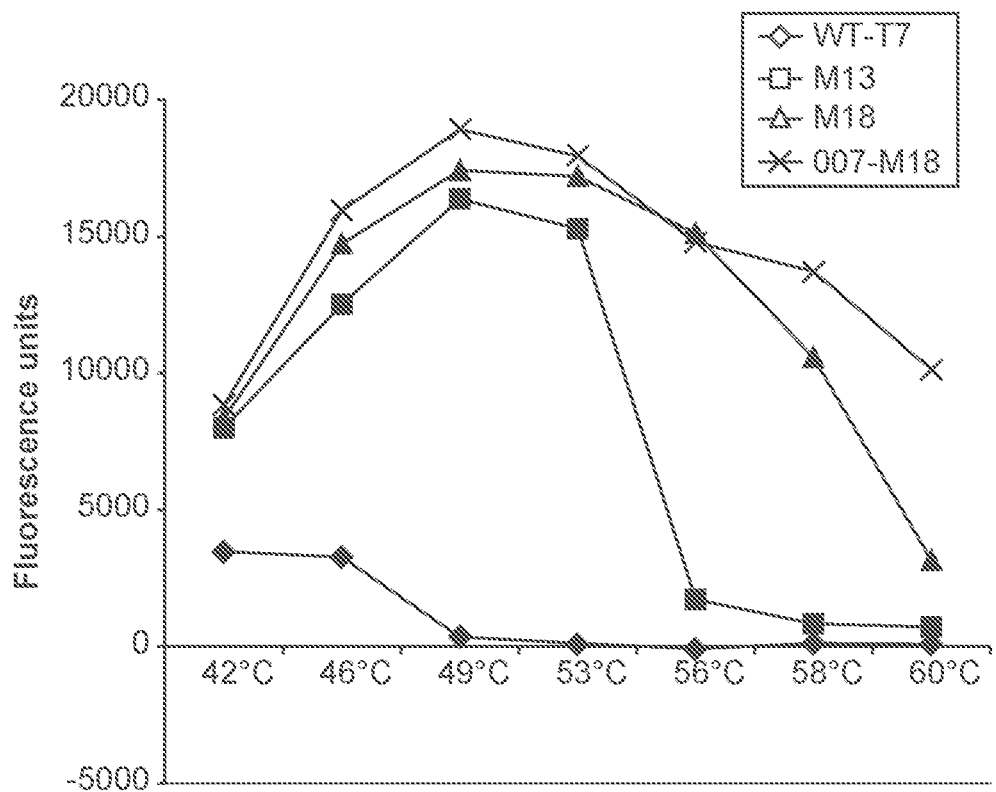
Figure 3C:
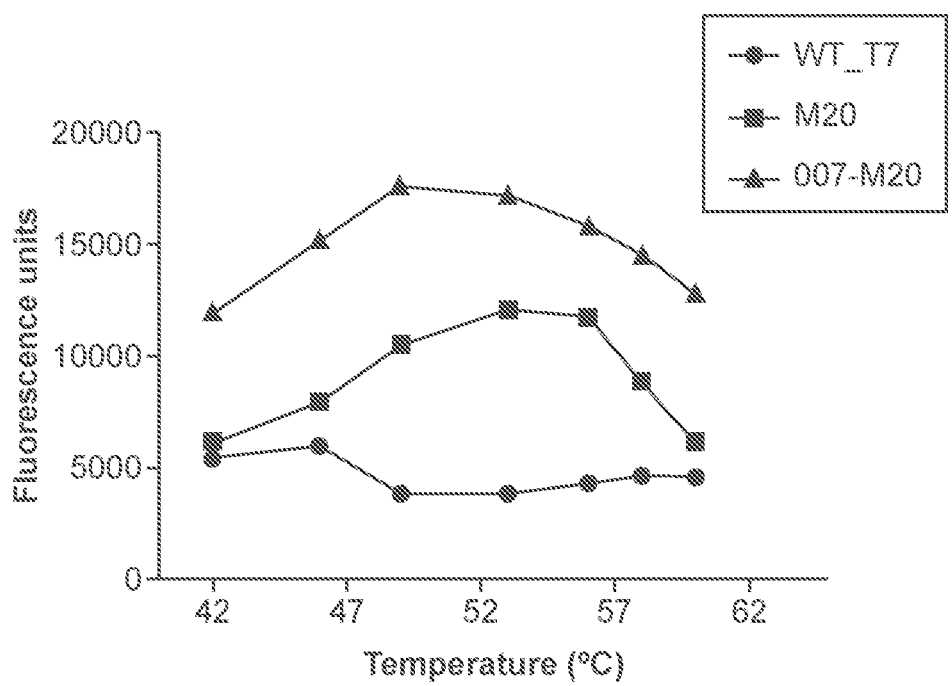

C. To determine the reaction temperature range (as shown in FIG. 3A), the yield of RNA synthesis was measured from 37° C. to 60° C. Each 25 µl reaction contains a final concentration of 50 mM Hepes-KOH, pH 7.5, 10 mM $Mg(OAc)_2$, 5 mM DTT, 2 mM spermidine, 1 mM NTP, 4 ng/µl linear DNA template of the Green Fluorescent protein reporter gene with T7 promoter, and 8 µg/ml T7 RNA polymerase variant. Reactions were run at various temperatures using Bio-Rad T100™ Thermal Cycler (Bio-Rad, Hercules, Calif.) for 2 hours. After the transcription reactions, 1 unit of DNase I (New England Biolabs, Ipswich, Mass.) was added and the reactions were incubated at 37° C. for 30 minutes.

Total synthesized RNA was measured using a Qubit® RNA BR Assay Kit (Thermo Fisher Scientific, Waltham, Mass.) to measure GFP mRNA.

Example 3: Beacon Assays

Wild type T7 RNA polymerase and two different variants were fused to the sso7d DNA binding domain (of sequence ATVKFKYKGEEKEVDISKIKKVWRVGKMISFTYDE-GGDKTGRGAVSEKDAPKELLQMLEKQKK; SEQ ID NO:6), the DNA binding domain from a helix-turn-helix (HTH) from *Pyrococcus furiosus* (of sequence GRKVRTQQNEILNLLNEKEKAVLRAILEHGGEIK-QEDLPELVGYSRPTISKVIQELENKGLIKREKSGK-TFVVKIERKIKLDKMGAPT; SEQ ID NO:7) or the DNA binding domain of a lacI-like protein from *Thermotoga* (of sequence KRRPTINDVAKLAGVSISTVSRYLKDP-SQVSEKLGERIREAIKKLGYKPNKIAQGLRTGD; SEQ ID NO:8). The fusion proteins were purified as described in Example 2A above. The fusion proteins were tested in a molecular beacon assay at various temperatures, as shown in FIGS. 3B-3C, FIG. 4 and FIG. 5 and their thermostability compared to variant RNA polymerases that were not fused. M13, M18 and M20 variants in FIGS. 3B-3C, FIG. 4 and FIG. 5 are examples of an amino acid sequence that is at least 80% sequence identity to SEQ ID NO:1; and include an amino acid substitution at positions corresponding to 109L, 205S, 388E, 534V, 567P and 618Q of SEQ ID NO:1.

The yields were compared using a molecular beacon assay that monitors in vitro transcription of a 6 Kb transcript. The in vitro transcription reactions were performed in 41 mM Tris-HCl pH 8.0, 50 mM NaCl, 19 mM $MgCl_2$, 5.5 mM DTT, 1 mM spermidine, 4 mM of each ribonucleotide, 4.15 units/mL yeast inorganic pyrophosphatase, 1000 units/mL murine ribonuclease inhibitor, 30 nM DNA template, 30 nM RNA polymerase, and 0.5 µM molecular beacon probe. A linearized plasmid DNA was used as template for the in vitro transcription reactions. The molecular beacon was designed to bind a 24 nucleotide target site upstream of the linearization site of the plasmid with a sequence of: 5'-CCT GC GATT GAA CAC GTG GGT CAG AGA GG GCAGG-3' (SEQ ID NO:9). The molecular beacons were labeled with the fluorescent dye TYE665 at the 5' end and the quencher IAbRQSp at the 3' end (or with the fluorescent dye 6-FAM at the 5' end and the quencher BHQ1 at the 3' end) (Integrated DNA Technologies, Coralville, Iowa). Reactions were run at various temperatures using a CFX96 Touch Real-Time PCT Detection System for one hour. The graph denotes end-point fluorescence units (representing the final yield from the in vitro transcription reaction) obtained for each polymerase plotted against the temperature at which the reactions were run.

Example 4: NASBA Assays

Figure 7A:
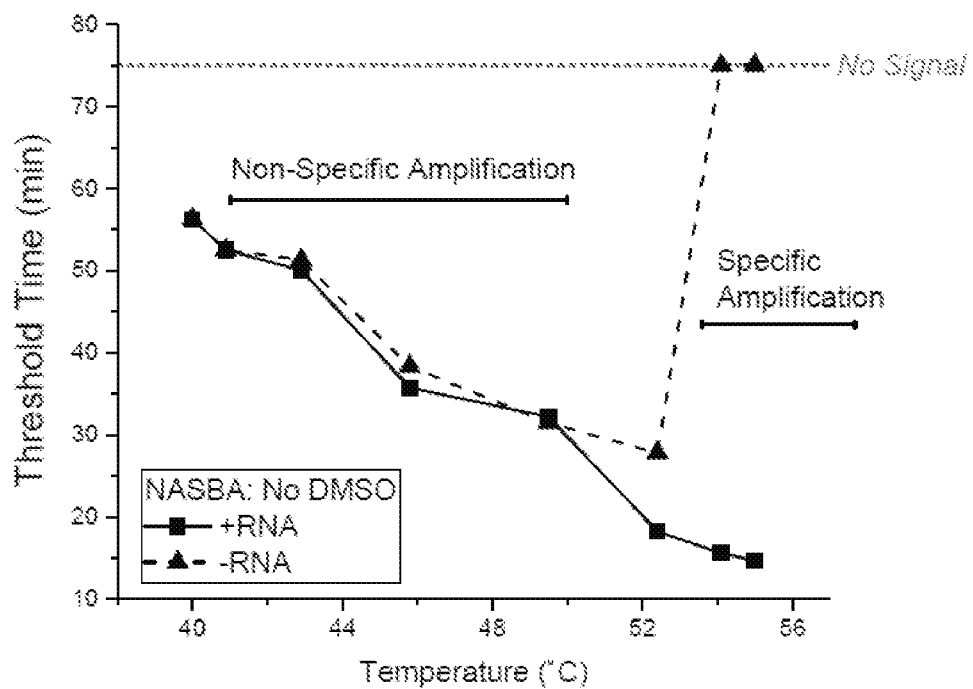
FIG. 7A-7B shows that NASBA reactions performed at a higher temperature (e.g., 50-56° C.) have faster amplification times and are more specific than reactions performed at a lower temperature, and that DMSO is not required for this effect. At temperatures below 50° C. all reactions, positive and negative, amplified with similar threshold times. Increasing temperature above 50° C. produced faster amplification times in positive reactions while suppressing amplification in the negative reactions. The no-detectable amplification results are plotted as maximum reaction time, 75 minutes, as indicated by horizontal dashed line. Temperatures of 54-56° C. provided the fastest amplification and maximum discrimination between positive and negative reactions.
Figure 7B:
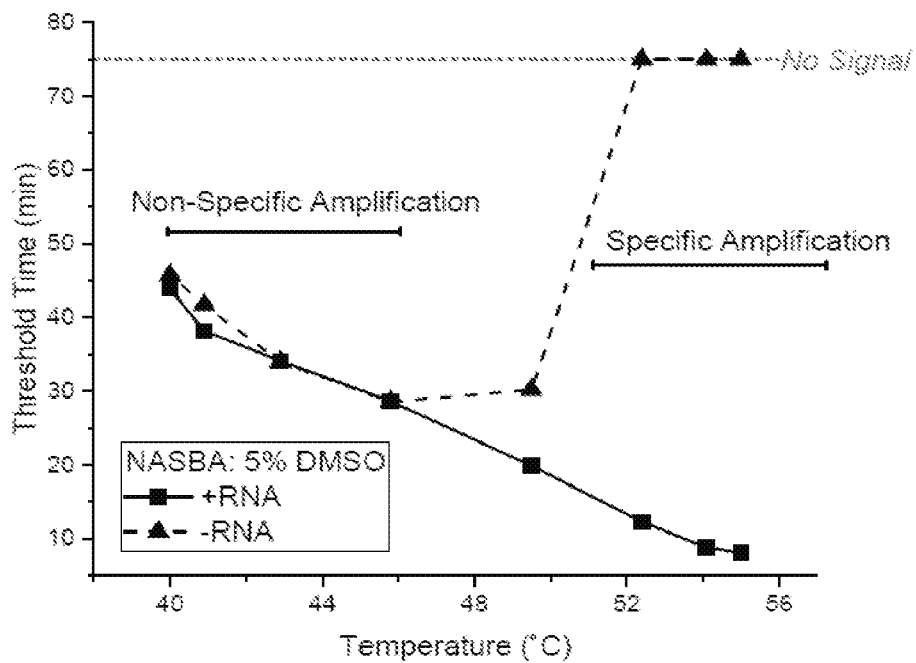

NASBA reactions were performed by first incubating RNA template (Jurkat total RNA), 250 nM forward primer (5'-AATTCTAATACGACTCACTATAGGGAGAGGCC-CGGCATGTGGTGCATAA-3'; SEQ ID NO:71), 250 nM reverse primer (5'-CAGTATGCCAAGACCGACTCAGA-3'; SEQ ID NO:72) and 100 nM molecular beacon (5'-FAM-CGTACGAGAAGAGGAAGCCCAAGAGC-CACGTACG-BHQ1-3', in which "FAM" refers to the dye 6-carboxyfluorescein and "BHQ" is Black Hole Quencher 1; SEQ ID NO:73) in 1×NASBA Buffer (40 mM Tris-HCl pH 8.5, 12 mM $MgCl_2$, 70 mM KCl, 10 mM DTT) with 1 mM each dATP, dCTP, dGTP and dTTP, 2 mM each ATP, CTP, GTP, and UTP, and 0-5% v/v DMSO as indicated. Water was added in place of RNA to the −RNA control reactions. RNA+primer mixture was heated to 65° C. for 2 minutes and temperature reduced to 40-56° C. as indicated. After 10-minute incubation at secondary temperature, NASBA enzymes were added at final concentrations of 2-10 ng/µL RNA polymerase variant (M20), 50-250 ng/µL Reverse Transcriptase variant, and 0.005-0.02 U/µL *Thermus thermophilus* RNase H. Incubation continued at the indicated gradient (40-56° C.) temperatures and data was collected by fluorescence measurement every 30 seconds using the FAM channel of a Bio-Rad CFX96 real time instrument. Instrument-defined threshold times are shown in FIGS. 7A and 7B, with positive (+RNA) reactions indicated by squares and solid line, negative (−RNA) reactions by triangles and dashed line. This data shows that NASBA reactions that are done at a higher temperature (e.g., in the range of 45° C. to 60° C.) produce less non-specific amplification products relative to the same reactions that are done at a lower temperature (e.g., 41° C.), and that the effect is not dependent upon DMSO.

What is claimed is:

1. An RNA polymerase, wherein the RNA polymerase: (a) is fused to an exogenous DNA binding domain, and (b) has (i) at least 90% sequence identity to SEQ ID NO: 1, and (ii) at least one amino acid substitution corresponding to a position selected from the group consisting of: 109, 205, 534, 567, and 618 of SEQ ID NO:1.

2. The RNA polymerase of claim 1, wherein the RNA polymerase comprises at least two substitutions at positions corresponding to positions selected from the group consisting of: 109, 205, 388, 534, 567, and 618 in SEQ ID NO:1.

3. The RNA polymerase of claim 1, wherein the RNA polymerase comprises substitutions at positions corresponding to positions 109, 205, 534, 567, and 618 in SEQ ID NO:1.

4. The RNA polymerase of claim 1, wherein the substitution corresponding to position 109 of SEQ ID NO:1 is I109L, the substitution corresponding to position 205 of SEQ ID NO:1 is H205S, the substitution corresponding to position 534 of SEQ ID NO:1 is L534V, the substitution corresponding to position 567 of SEQ ID NO:1 is V567P and the substitution corresponding to position 618 of SEQ ID NO:1 is G618Q.

5. The RNA polymerase of claim 1 further comprising at least one additional amino acid substitution at a position corresponding to a position selected from the group consisting of: 75, 83, 108, 206, 227, 281, 297, 312, 323, 327, 333, 340, 354, 362, 375, 388, 428, 446, 454, 461, 495, 510, 584, 591, 642, 711, 724, 740, 788, 832, 834, 835, 843, 847, 849, 856, 863, 866 and 877 of SEQ ID NO:1.

6. The RNA polymerase of claim 1 comprising at least 10 additional substitutions at positions corresponding to a position selected from the group consisting of: 75, 83, 108, 206, 227, 281, 297, 312, 323, 327, 333, 340, 354, 362, 375, 788, 428, 446, 454, 461, 495, 510, 584, 591, 642, 711, 724, 740, 788, 832, 834, 835, 843, 847, 849, 856, 863, 866 and 877 of SEQ ID NO:1.

7. The RNA polymerase of claim 1 comprising at least one additional amino acid substitution selected from the group consisting of: T75Q, A83K, E108L, K206P, V227I, I281P, V297I, Y312D, A323I, A327P, K333P, V340E, A354Q, M362P, T375K, T375N, D388E, A428P, L446F, K454P, K461R, S495N, C510Q, A584K, D591E, K642R, K711R, A724P, K740R, G788A, M832F, D834E, T835L, A843Q, D847E, F849V, S856T, A863P, A866K and E877R.

8. The RNA polymerase of claim 1 comprising at least ten additional substitutions selected from the group consisting of: T75Q, A83K, E108L, K206P, V227I, I281P, V297I, Y312D, A323I, A327P, K333P, V340E, A354Q, M362P, T375K, T375N, D388E, A428P, L446F, K454P, K461R, S495N, C510Q, A584K, D591E, K642R, K711R, A724P, K740R, G788A, M832F, D834E, T835L, A843Q, D847E, F849V, S856T, A863P, A866K and E877R.

9. The RNA polymerase of claim 1, wherein, as a result of the at least one amino acid substitution, the RNA polymerase has increased activity at temperatures above 42° C., 45° C., 50° C. or 55° C. relative to the T7 RNA polymerase of SEQ ID NO:1.

10. The RNA polymerase of claim 1, wherein the polymerase has at least 95% sequence identity to any of SEQ ID NOs:52-70.

11. A composition comprising:
the RNA polymerase of claim 1; and
a buffering agent.

12. The composition of claim 11, further comprising ribonucleoside triphosphates and/or a modified nucleotide.

13. The composition of claim 11, further comprising a template DNA molecule comprising: a bacteriophage RNA polymerase promoter, operably linked to a target nucleotide sequence to be transcribed.

14. A method for synthesizing an RNA molecule comprising:
incubating a reaction mix comprising the RNA polymerase of claim 1, ribonucleoside triphosphates optionally including one or more modified ribonucleotides, and a template DNA molecule comprising a bacteriophage RNA polymerase promoter that is operably linked to a target nucleotide sequence to be transcribed, thereby transcribing the template DNA molecule into RNA.

15. The method of claim 14, wherein the incubating is done at a temperature of at least 45° C.

16. The method of claim 14, wherein the bacteriophage RNA polymerase promoter is a T7 RNA polymerase promoter.

17. The method of claim 14, wherein the method is a nucleic acid sequence-based amplification (NASBA) method that comprises: reverse transcribing an RNA template to produce an RNA-cDNA hybrid, treating the RNA-cDNA hybrid to destroy the RNA template and leave the cDNA strand, hybridizing a primer to the cDNA strand, wherein the primer comprises the bacteriophage RNA polymerase promoter, extending the primer to produce a second strand, and transcribing the second strand using the RNA polymerase to produce an RNA product.

18. The method of claim 17, further comprising detecting the RNA product.

19. A protein comprising:
(a) an RNA polymerase having: (i) at least 90% sequence identity to SEQ ID NO:1, and (ii) at least two amino acid substitutions at positions corresponding to positions selected from the group consisting of: 109, 205, 388, 534, 567 and 618 of SEQ ID NO:1; and
(b) an exogenous DNA binding domain fused to the RNA polymerase.

20. The protein of claim 19, wherein the RNA polymerase comprises at least one further substitution, deletion or insertion at positions corresponding to positions of SEQ ID NO:1 selected from the group consisting of: 75, 83, 108, 206, 227, 281, 297, 312, 323, 327, 333, 340, 354, 362, 375, 428, 446, 454, 461, 495, 510, 584, 591, 642, 711, 724, 740, 788, 832, 834, 835, 843, 847, 849, 856, 863, 866 and 877.

* * * * *

SEQUENCE LISTING

```
<160> NUMBER OF SEQ ID NOS: 77

<210> SEQ ID NO 1
<211> LENGTH: 883
<212> TYPE: PRT
<213> ORGANISM: Artificial Sequence
<220> FEATURE:
<223> OTHER INFORMATION: Synthetic construct

<400> SEQUENCE: 1

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
```

```
            195                 200                 205
Ser Ile His Val Gly Val Arg Cys Ile Glu Met Leu Ile Glu Ser Thr
210                 215                 220
Gly Met Val Ser Leu His Arg Gln Asn Ala Gly Val Val Gly Gln Asp
225                 230                 235                 240
Ser Glu Thr Ile Glu Leu Ala Pro Glu Tyr Ala Glu Ala Ile Ala Thr
                245                 250                 255
Arg Ala Gly Ala Leu Ala Gly Ile Ser Pro Met Phe Gln Pro Cys Val
            260                 265                 270
Val Pro Pro Lys Pro Trp Thr Gly Ile Thr Gly Gly Tyr Trp Ala
            275                 280                 285
Asn Gly Arg Arg Pro Leu Ala Leu Val Arg Thr His Ser Lys Lys Ala
290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Glu Asp Ile
            340                 345                 350
Pro Ala Ile Glu Arg Glu Leu Pro Met Lys Pro Glu Asp Ile Asp
                355                 360                 365
Met Asn Pro Glu Ala Leu Thr Ala Trp Lys Arg Ala Ala Ala Val
370                 375                 380
Tyr Arg Lys Asp Lys Ala Arg Lys Ser Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
                500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
            530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
                580                 585                 590
Glu Val Val Thr Val Thr Asp Glu Asn Thr Gly Glu Ile Ser Glu Lys
            595                 600                 605
Val Lys Leu Gly Thr Lys Ala Leu Ala Gly Gln Trp Leu Ala Tyr Gly
            610                 615                 620
```

-continued

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 2
<211> LENGTH: 18
<212> TYPE: DNA
<213> ORGANISM: Artificial Sequence
<220> FEATURE:
<223> OTHER INFORMATION: Synthetic construct

<400> SEQUENCE: 2
taatacgact cactatag                                                18

<210> SEQ ID NO 3
<211> LENGTH: 18
<212> TYPE: DNA
<213> ORGANISM: Artificial Sequence
<220> FEATURE:
<223> OTHER INFORMATION: Synthetic construct

<400> SEQUENCE: 3
aattaaccct cactaaag                                                18

<210> SEQ ID NO 4
<211> LENGTH: 18
<212> TYPE: DNA

```
<213> ORGANISM: Artificial Sequence
<220> FEATURE:
<223> OTHER INFORMATION: Synthetic construct

<400> SEQUENCE: 4
tatttaccct cactaaag                                                    18

<210> SEQ ID NO 5
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(22)
<223> OTHER INFORMATION: n is a, c, g, or t

<400> SEQUENCE: 5
atttaggtga cactatagaa gng                                              23

<210> SEQ ID NO 6
<211> LENGTH: 63
<212> TYPE: PRT
<213> ORGANISM: Artificial Sequence
<220> FEATURE:
<223> OTHER INFORMATION: Synthetic construct

<400> SEQUENCE: 6

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Asp Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60

<210> SEQ ID NO 7
<211> LENGTH: 88
<212> TYPE: PRT
<213> ORGANISM: Pyrococcus furiosus

<400> SEQUENCE: 7

Gly Arg Lys Val Arg Thr Gln Gln Asn Glu Ile Leu Asn Leu Leu Asn
1               5                   10                  15

Glu Lys Glu Lys Ala Val Leu Arg Ala Ile Leu Glu His Gly Gly Glu
            20                  25                  30

Ile Lys Gln Glu Asp Leu Pro Glu Leu Val Gly Tyr Ser Arg Pro Thr
        35                  40                  45

Ile Ser Lys Val Ile Gln Glu Leu Glu Asn Lys Gly Leu Ile Lys Arg
    50                  55                  60

Glu Lys Ser Gly Lys Thr Phe Val Val Lys Ile Glu Arg Lys Ile Lys
65                  70                  75                  80

Leu Asp Lys Met Gly Ala Pro Thr
                85

<210> SEQ ID NO 8
<211> LENGTH: 60
<212> TYPE: PRT
<213> ORGANISM: Thermotoga maritima

<400> SEQUENCE: 8
```

```
Lys Arg Arg Pro Thr Ile Asn Asp Val Ala Lys Leu Ala Gly Val Ser
1               5                   10                  15

Ile Ser Thr Val Ser Arg Tyr Leu Lys Asp Pro Ser Gln Val Ser Glu
                20                  25                  30

Lys Leu Gly Glu Arg Ile Arg Glu Ala Ile Lys Lys Leu Gly Tyr Lys
            35                  40                  45

Pro Asn Lys Ile Ala Gln Gly Leu Arg Thr Gly Asp
    50                  55                  60

<210> SEQ ID NO 9
<211> LENGTH: 34
<212> TYPE: DNA
<213> ORGANISM: Artificial Sequence
<220> FEATURE:
<223> OTHER INFORMATION: Synthetic construct

<400> SEQUENCE: 9
cctgcgattg aacacgtggg tcagagaggg cagg                                  34

<210> SEQ ID NO 10
<211> LENGTH: 142
<212> TYPE: PRT
<213> ORGANISM: Pyrococcus furiosus

<400> SEQUENCE: 10

Met Lys Thr Phe Leu Thr Glu Gln Gln Ile Lys Val Leu Met Leu Arg
1               5                   10                  15

Ala Lys Gly Tyr Lys Gln Ser Glu Ile Ala Lys Ile Leu Gly Thr Ser
                20                  25                  30

Arg Ala Asn Val Ser Ile Leu Glu Lys Arg Ala Met Glu Lys Ile Glu
            35                  40                  45

Lys Ala Arg Asn Thr Leu Leu Leu Trp Glu Gln Ile Asn Ser Lys Val
    50                  55                  60

Ile Val Glu Ile Lys Ala Gly Glu Asp Ile Phe Ser Ile Pro Glu Lys
65                  70                  75                  80

Phe Phe Lys Lys Ala Asp Lys Val Gly Val Lys Val Pro Tyr Ser Thr
                85                  90                  95

Ala Glu Ile Ile Thr Phe Leu Val Glu His Ala Pro Val Glu Asp Arg
            100                 105                 110

Leu Ala Lys Arg Asp Phe Val Leu Phe Leu Asp Ser Lys Asn Lys Leu
    115                 120                 125

Arg Ile Gly Asp Cys Leu Val Ile Glu Glu Ile Lys Glu Asp
    130                 135                 140

<210> SEQ ID NO 11
<211> LENGTH: 75
<212> TYPE: PRT
<213> ORGANISM: Pyrococcus furiosus

<400> SEQUENCE: 11

Met Pro Ile Thr Lys Val Thr Arg Asn Tyr Gln Ile Thr Ile Pro Ala
1               5                   10                  15

Glu Ile Arg Lys Ala Leu Gly Ile Lys Glu Gly Glu Leu Leu Glu Val
                20                  25                  30

Arg Leu Glu Asn Gly Lys Ile Ile Glu Arg Leu Lys Lys Glu Arg
            35                  40                  45

Lys Thr Leu Lys Leu Gly Lys Lys Leu Thr Leu Glu Glu Ile Glu Lys
    50                  55                  60
```

```
Ala Ile Glu Glu Gly Met Lys Gln Cys Met Gln
 65                  70                  75

<210> SEQ ID NO 12
<211> LENGTH: 76
<212> TYPE: PRT
<213> ORGANISM: Pyrococcus furiosus

<400> SEQUENCE: 12

Thr Lys Ile Glu Ile Leu Arg Leu Leu Lys Glu Arg Glu Met Tyr Ala
  1               5                  10                  15

Tyr Glu Ile Trp Ser Leu Leu Gly Lys Pro Leu Lys Tyr Gln Ala Val
                 20                  25                  30

His Gln His Ile Lys Glu Leu Leu Glu Leu Gly Leu Val Glu Gln Ala
             35                  40                  45

Tyr Arg Lys Gly Lys Arg Val Tyr Tyr Lys Ile Thr Glu Lys Gly Leu
         50                  55                  60

Arg Ile Leu Gln Asn Phe Glu Asp Leu Glu Asn Ile
 65                  70                  75

<210> SEQ ID NO 13
<211> LENGTH: 72
<212> TYPE: PRT
<213> ORGANISM: Pyrococcus furiosus

<400> SEQUENCE: 13

Met Asn Thr Gly Ala Gln Gly Val Ser Glu Met Ser Arg Met Lys Ile
  1               5                  10                  15

Ile Ser Val Gln Leu Pro Gln Ser Leu Ile His Gly Leu Asp Ala Leu
                 20                  25                  30

Val Lys Arg Gly Ile Tyr Pro Asn Arg Ser Glu Ala Ile Arg Val Ala
             35                  40                  45

Ile Arg Glu Leu Leu Lys Lys Glu Leu Tyr Lys Glu Glu Ile Gln Glu
         50                  55                  60

Glu Ile Pro Glu Tyr Val Val Lys
 65                  70

<210> SEQ ID NO 14
<211> LENGTH: 67
<212> TYPE: PRT
<213> ORGANISM: Pyrococcus furiosus

<400> SEQUENCE: 14

Val Ile Ile Pro Arg Pro Ile Asp Pro Arg Asp Ile Arg Arg Ile Arg
  1               5                  10                  15

Lys Glu Leu Gly Ile Thr Gln Glu Glu Leu Ala Arg Lys Ala Gly Val
                 20                  25                  30

Thr Gln Ala Tyr Ile Ala Lys Leu Glu Ala Gly Lys Val Asp Pro Arg
             35                  40                  45

Leu Ser Thr Phe Asn Lys Ile Leu Arg Ala Leu Ile Glu Cys Gln Lys
         50                  55                  60

Ala Lys Ile
 65

<210> SEQ ID NO 15
<211> LENGTH: 65
<212> TYPE: PRT
<213> ORGANISM: Pyrococcus furiosus
```

<400> SEQUENCE: 15

Asn Asn Cys Glu Cys Met Val Val Lys Glu Lys Leu Tyr Thr Val Lys
1               5                   10                  15

Gln Ala Ser Glu Ile Leu Gly Val His Pro Lys Thr Ile Gln Lys Trp
            20                  25                  30

Asp Arg Glu Gly Lys Ile Lys Thr Val Arg Thr Pro Gly Gly Arg Arg
        35                  40                  45

Arg Ile Pro Glu Ser Glu Ile Lys Arg Leu Leu Gly Ile Ser Glu Glu
    50                  55                  60

Lys
65

<210> SEQ ID NO 16
<211> LENGTH: 71
<212> TYPE: PRT
<213> ORGANISM: Pyrococcus furiosus

<400> SEQUENCE: 16

Met Leu Lys Asp Ser Ala Pro Lys Arg Lys Ile Leu Glu Glu Leu Arg
1               5                   10                  15

Lys Gly Glu Thr Val Ser Gly Asp Tyr Leu Ala Ser Lys Leu Gly Val
            20                  25                  30

Ser Arg Val Ala Ile Trp Lys His Ile Arg Glu Leu Lys Glu Leu Gly
        35                  40                  45

Tyr Gly Ile Ile Ala Asp Lys Lys Gly Tyr Lys Leu Val Tyr Glu Pro
    50                  55                  60

Lys Lys Pro Tyr Pro Trp Glu
65                  70

<210> SEQ ID NO 17
<211> LENGTH: 86
<212> TYPE: PRT
<213> ORGANISM: Pyrococcus furiosus

<400> SEQUENCE: 17

Met Ile Asp Glu Arg Asp Lys Ile Ile Leu Glu Ile Leu Glu Lys Asp
1               5                   10                  15

Ala Arg Thr Pro Phe Thr Glu Ile Ala Lys Lys Leu Gly Ile Ser Glu
            20                  25                  30

Thr Ala Val Arg Lys Arg Val Lys Ala Leu Glu Glu Lys Gly Ile Ile
        35                  40                  45

Glu Gly Tyr Thr Ile Lys Ile Asn Pro Lys Lys Leu Gly Tyr Ser Leu
    50                  55                  60

Val Thr Ile Thr Gly Val Asp Thr Lys Pro Lys Leu Phe Glu Val
65                  70                  75                  80

Ala Glu Lys Leu Lys Glu
                85

<210> SEQ ID NO 18
<211> LENGTH: 77
<212> TYPE: PRT
<213> ORGANISM: Pyrococcus furiosus

<400> SEQUENCE: 18

Met Glu Ile Asp Asp Leu Asp Arg Lys Ile Leu Ser Leu Leu Ile Glu
1               5                   10                  15

Asp Ser Arg Leu Ser Tyr Arg Glu Ile Ala Lys Lys Leu Asn Val Ala
            20                  25                  30

Val Gly Thr Ile Tyr Asn Arg Ile Lys Lys Leu Glu Asp Met Gly Val
                35                  40                  45

Ile Gln Gly Phe Thr Val Lys Leu Asn Tyr Glu Lys Leu Gly Tyr Glu
 50                  55                  60

Leu Thr Ala Ile Ile Gly Ile Lys Ala Gln Gly Lys Lys
 65                  70                  75

<210> SEQ ID NO 19
<211> LENGTH: 94
<212> TYPE: PRT
<213> ORGANISM: Pyrococcus furiosus

<400> SEQUENCE: 19

Glu Met Leu Trp Met Tyr Ile Leu Lys Leu Leu Lys Asp Arg Pro Met
 1               5                   10                  15

Tyr Ala Tyr Glu Ile Arg Asn Glu Leu Lys Lys Arg Phe Gly Phe Glu
                20                  25                  30

Pro Ala Thr Val Ser Ser Tyr Val Val Leu Tyr Arg Leu Glu Glu Gly
                35                  40                  45

Gly Tyr Val Ser Ser Glu Trp His Glu Ser Glu Ala Gly Arg Pro Ser
 50                  55                  60

Arg Lys Tyr Tyr Arg Leu Thr Glu Lys Gly Lys Leu Leu Glu Lys
 65                  70                  75                  80

Gly Ile Glu Thr Ile Glu Asp Val Leu Asn Met Leu Lys Ser
                85                  90

<210> SEQ ID NO 20
<211> LENGTH: 68
<212> TYPE: PRT
<213> ORGANISM: Pyrococcus furiosus

<400> SEQUENCE: 20

Met Lys Val Ser Lys Ala Thr Ala Ser Lys Val Leu Arg Ser Leu Glu
 1               5                   10                  15

Asn Lys Gly Ile Val Glu Arg Glu Arg Arg Gly Lys Thr Tyr Leu Val
                20                  25                  30

Arg Leu Thr Asn Lys Gly Leu Glu Leu Leu Glu Glu Ile Ser Lys Ala
                35                  40                  45

Gly Lys Glu Leu Asp Glu Lys Ile Phe Ala Glu Met Ser Val Asp Glu
 50                  55                  60

Arg Ile Val Leu
 65

<210> SEQ ID NO 21
<211> LENGTH: 56
<212> TYPE: PRT
<213> ORGANISM: Pyrococcus furiosus

<400> SEQUENCE: 21

Ser Glu Asp Tyr Met Leu Gln Asn Arg Arg Lys Val Leu Ala Lys Val
 1               5                   10                  15

Leu Glu Leu Leu Asn Tyr Asn Pro Lys Ala Leu Asn Ile Ser Glu Leu
                20                  25                  30

Ala Arg Met Phe Gly Val Ser Arg Asp Thr Ile Tyr Asn Asp Ile Gln
                35                  40                  45

Gln Ile Ile Lys Asn Val Glu Val
 50                  55

<210> SEQ ID NO 22
<211> LENGTH: 94
<212> TYPE: PRT
<213> ORGANISM: Pyrococcus furiosus

<400> SEQUENCE: 22

Ser Lys Glu Ile Ser Arg Phe Leu Lys Val Ile Ser Asn Pro Ile Arg
1               5                   10                  15

Tyr Gly Ile Leu Lys Met Leu Asn Asp Arg Trp Met Cys Val Cys Leu
            20                  25                  30

Ile Ser Glu Ala Leu Glu Ile Asp Gln Thr Leu Val Ser His His Ile
        35                  40                  45

Arg Ile Leu Lys Glu Leu Asp Leu Leu Glu Glu Arg Lys Glu Gly Lys
    50                  55                  60

Leu Arg Phe Tyr Arg Thr Asn Lys Glu Lys Leu Arg Glu Tyr Leu Glu
65                  70                  75                  80

Lys Val Leu Glu Asp Phe Asn His Gly Thr Ser Lys Gly Ser
                85                  90

<210> SEQ ID NO 23
<211> LENGTH: 78
<212> TYPE: PRT
<213> ORGANISM: Pyrococcus furiosus

<400> SEQUENCE: 23

Met Cys Arg Lys Asp Val Met Ile Ile Ser Asp Pro Lys Gln Ile Lys
1               5                   10                  15

Ala Leu Ser Asp Pro Thr Arg Val Lys Ile Leu Glu Leu Leu Arg Tyr
            20                  25                  30

His Pro Met Thr Val Ser Glu Ile Ser Arg Val Ile Gly Lys Asp Lys
            35                  40                  45

Ser Thr Ile Tyr Arg His Ile Lys Ala Leu Glu Glu Ala Gly Leu Val
    50                  55                  60

Glu Glu Val Glu Lys Ile Gly Asn Glu Thr Val Tyr Gly Arg
65                  70                  75

<210> SEQ ID NO 24
<211> LENGTH: 122
<212> TYPE: PRT
<213> ORGANISM: Pyrococcus furiosus

<400> SEQUENCE: 24

Met Glu Pro Val Glu Phe Lys Leu Asn Gln Lys Gly Ile Lys Ser Ile
1               5                   10                  15

Leu Pro Thr Met Glu Ala Glu Ile Met Glu Tyr Met Trp Glu Ile Lys
            20                  25                  30

Glu Ala Thr Ala Gly Glu Val Tyr Glu Tyr Met Lys Thr Lys Tyr Pro
            35                  40                  45

Glu Ile Arg Arg Ser Thr Val Ser Ile Leu Met Asn Arg Leu Cys Glu
    50                  55                  60

Arg Gly Leu Leu Lys Arg Met Glu Lys Gly Lys Gly Ile Arg
65                  70                  75                  80

Tyr Val Tyr Ser Ile Thr Thr Thr Arg Glu Glu Phe Glu Arg Lys Val
                85                  90                  95

Val Glu Lys Ile Ile Glu Ser Leu Met Met Asn Phe Arg Glu Ala Thr
                100                 105                 110

Phe Ala Tyr Leu Ser Lys Ile Asn Lys Lys 115                 120

<210> SEQ ID NO 25
<211> LENGTH: 87
<212> TYPE: PRT
<213> ORGANISM: Pyrococcus furiosus

<400> SEQUENCE: 25

Met Lys Lys Ser Asn Leu Asp Leu Leu Ile Leu Leu Ala Lys Ala Gly
1               5                   10                  15

Gly Ile Glu Lys Glu Ile Leu Thr Thr Ser Arg Glu Leu Ser Lys Met
            20                  25                  30

Leu Asn Val Ser Pro Gln Thr Ile Val Arg Trp Leu Glu Asp Leu Glu
        35                  40                  45

Lys Asp Gly Leu Ile Lys Lys Ser Glu Ser Arg Lys Gly Thr Leu Val
    50                  55                  60

Thr Ile Thr Glu Glu Gly Val Lys Phe Leu Glu Lys Leu His Glu Glu
65                  70                  75                  80

Leu Ser Asp Ala Leu Tyr Arg
                85

<210> SEQ ID NO 26
<211> LENGTH: 104
<212> TYPE: PRT
<213> ORGANISM: Unknown
<220> FEATURE:
<223> OTHER INFORMATION: Thermococcaceae

<400> SEQUENCE: 26

Met Glu Ile Pro Pro Glu Ile Ser His Ala Leu Ser Glu Ile Gly Phe
1               5                   10                  15

Thr Lys Tyr Glu Ile Leu Thr Tyr Trp Thr Leu Leu Val Tyr Gly Pro
            20                  25                  30

Ser Thr Ala Lys Glu Ile Ser Thr Lys Ser Gly Ile Pro Tyr Asn Arg
        35                  40                  45

Val Tyr Asp Thr Ile Ser Ser Leu Lys Leu Arg Gly Phe Val Thr Glu
    50                  55                  60

Ile Glu Gly Thr Pro Lys Val Tyr Ala Ala Tyr Ser Pro Arg Ile Ala
65                  70                  75                  80

Phe Phe Arg Phe Lys Lys Glu Leu Glu Asp Ile Met Lys Lys Leu Glu
                85                  90                  95

Ile Glu Leu Asn Asn Val Lys Lys
            100

<210> SEQ ID NO 27
<211> LENGTH: 75
<212> TYPE: PRT
<213> ORGANISM: Pyrococcus furiosus

<400> SEQUENCE: 27

Ile Ile Asn Pro Gln Ala Arg Leu Thr Pro Leu Glu Leu Glu Ile Leu
1               5                   10                  15

Glu Ile Ile Lys Gln Lys Lys Ser Ile Thr Ile Thr Glu Ile Lys Glu
            20                  25                  30

Ile Leu Ser Glu Arg Arg Lys Ser Glu Tyr Pro Leu Ser Leu Val Ser
        35                  40                  45

Glu Tyr Ile Ser Arg Leu Glu Arg Lys Gly Tyr Val Lys Lys Ile Ala
    50                  55                  60

```
Lys Gly Arg Lys Lys Phe Val Glu Ala Leu Ile
 65                  70                  75
```

<210> SEQ ID NO 28
<211> LENGTH: 94
<212> TYPE: PRT
<213> ORGANISM: Pyrococcus furiosus

<400> SEQUENCE: 28

```
Gly Ile Asp Val Val Ile Pro Glu Ile Lys His Asp Pro Ile Ala Arg
 1               5                  10                  15

Asp Ile Val Lys Ile Leu Phe Asp Leu Arg Arg Ala Asn Val Ser Gln
             20                  25                  30

Ile Ala Arg Glu Leu Lys Gly Arg Gly Lys Ala Ser Arg Asn Thr
         35                  40                  45

Val Arg Lys Lys Leu Lys Glu Leu Glu Lys Leu Gly Val Val Lys Glu
 50                  55                  60

Val Pro Gly Glu Arg Gly Ser Val Tyr Thr Leu Ser Arg Glu Val Val
 65                  70                  75                  80

Lys Lys Trp Leu Asp Leu Ile Gly Ile Pro Ile Asn Leu Leu
                 85                  90
```

<210> SEQ ID NO 29
<211> LENGTH: 67
<212> TYPE: PRT
<213> ORGANISM: Pyrococcus furiosus

<400> SEQUENCE: 29

```
Met Thr Lys Arg Val Lys Val Ile Thr Asp Pro Glu Val Ile Lys Val
 1               5                  10                  15

Met Leu Glu Asp Thr Arg Arg Lys Ile Leu Gln Leu Leu Arg Asn Arg
             20                  25                  30

Glu Met Thr Ile Ser Gln Leu Ser Glu Ile Leu Gly Lys Met Pro Gln
         35                  40                  45

Thr Ile Tyr His His Ile Glu Lys Leu Lys Glu Ala Gly Leu Val Glu
     50                  55                  60

Val Lys Arg
 65
```

<210> SEQ ID NO 30
<211> LENGTH: 100
<212> TYPE: PRT
<213> ORGANISM: Pyrococcus furiosus

<400> SEQUENCE: 30

```
Met Glu Glu Ile Lys Glu Ile Met Lys Ser His Thr Leu Gly Asn Pro
 1               5                  10                  15

Val Arg Leu Gly Ile Met Ile Tyr Leu Phe Pro Arg Arg Ala Pro
             20                  25                  30

Phe Ser His Ile Gln Lys Ala Leu Asp Leu Thr Pro Gly Asn Leu Asp
         35                  40                  45

Ser His Ile Lys Val Leu Glu Lys His Gly Phe Val Arg Thr Tyr Lys
     50                  55                  60

Val Ile Ala Asp Arg Pro Arg Thr Met Val Glu Ile Thr Asp Tyr Gly
 65                  70                  75                  80

Met Glu Glu Thr Arg Lys Phe Leu Ser His Leu Lys Thr Val Ile Asp
                 85                  90                  95

Ala Ile His Phe
```

<210> SEQ ID NO 31
<211> LENGTH: 99
<212> TYPE: PRT
<213> ORGANISM: Pyrococcus furiosus

<400> SEQUENCE: 31

Met Gly Glu Glu Leu Asn Arg Leu Leu Asp Val Leu Gly Asn Glu Thr
1               5                   10                  15
Arg Arg Arg Ile Leu Phe Leu Leu Thr Lys Arg Pro Tyr Phe Val Ser
                20                  25                  30
Glu Leu Ser Arg Glu Leu Gly Val Gly Gln Lys Ala Val Leu Glu His
            35                  40                  45
Leu Arg Ile Leu Glu Glu Ala Gly Leu Ile Glu Ser Arg Val Glu Lys
        50                  55                  60
Ile Pro Arg Gly Arg Pro Arg Lys Tyr Tyr Met Ile Lys Lys Gly Leu
65                  70                  75                  80
Arg Leu Glu Ile Leu Leu Thr Pro Thr Leu Phe Gly Ser Glu Met Tyr
                85                  90                  95
Glu Ala Lys

<210> SEQ ID NO 32
<211> LENGTH: 61
<212> TYPE: PRT
<213> ORGANISM: Pyrococcus furiosus

<400> SEQUENCE: 32

Met Arg Arg Met Asp Lys Val Asp Leu Gln Leu Ile Lys Ile Leu Ser
1               5                   10                  15
Gln Asn Ser Arg Leu Thr Tyr Arg Glu Leu Ala Glu Met Leu Gly Thr
                20                  25                  30
Thr Arg Gln Arg Val Ala Arg Lys Val Asp Lys Leu Lys Lys Leu Gly
            35                  40                  45
Ile Ile Arg Lys Phe Thr Ile Ile Pro Asn Leu Glu Lys
        50                  55                  60

<210> SEQ ID NO 33
<211> LENGTH: 82
<212> TYPE: PRT
<213> ORGANISM: Pyrococcus furiosus

<400> SEQUENCE: 33

Gly Arg Lys Val Arg Thr Gln Gln Asn Glu Ile Leu Asn Leu Leu Asn
1               5                   10                  15
Glu Lys Glu Lys Ala Val Leu Arg Ala Ile Leu Glu His Gly Gly Glu
                20                  25                  30
Ile Lys Gln Glu Asp Leu Pro Glu Leu Val Gly Tyr Ser Arg Pro Thr
            35                  40                  45
Ile Ser Lys Val Ile Gln Glu Leu Glu Asn Lys Gly Leu Ile Lys Arg
        50                  55                  60
Glu Lys Ser Gly Lys Thr Phe Val Val Lys Ile Glu Arg Lys Ile Lys
65                  70                  75                  80
Leu Asp

<210> SEQ ID NO 34
<211> LENGTH: 59
<212> TYPE: PRT

<213> ORGANISM: Thermotoga maritima

<400> SEQUENCE: 34

Lys Ser Leu Gln Arg Phe Leu Arg Arg Asn Thr Thr Ser Ile Lys His
1               5                   10                  15

Leu Ser Glu Ile Thr Gly Val Ala Arg Asn Arg Leu Ser Asp Ile Leu
            20                  25                  30

Asn Gly Lys Thr Gln Lys Ile Arg Gly Glu Thr Leu Arg Lys Ile Ala
        35                  40                  45

Lys Ala Phe Glu Lys Ser Asn Ile Leu Ser Phe
    50                  55

<210> SEQ ID NO 35
<211> LENGTH: 107
<212> TYPE: PRT
<213> ORGANISM: Thermotoga

<400> SEQUENCE: 35

Asp Val Ile Gln Arg Ile Lys Glu Lys Tyr Asp Glu Phe Thr Asn Ala
1               5                   10                  15

Glu Lys Lys Ile Ala Asp Thr Ile Leu Ser Asp Pro Lys Gly Ile Ile
            20                  25                  30

Glu Ser Ser Ile Ser Asp Leu Ser Glu Lys Ala Gly Val Lys Ser Glu
        35                  40                  45

Ala Ser Val Val Lys Phe Tyr Lys Lys Leu Gly Leu Asn Ser Phe Gln
    50                  55                  60

Gln Phe Lys Val Leu Leu Ala Gln Ser Ile Ser Arg Ala Pro Leu Glu
65                  70                  75                  80

Ile Val Tyr Glu Asp Val Ser Ser Glu Asp Asp Thr Lys Thr Ile Thr
                85                  90                  95

Glu Lys Ile Phe Lys Ala Thr Val Arg Ala Ile
            100                 105

<210> SEQ ID NO 36
<211> LENGTH: 101
<212> TYPE: PRT
<213> ORGANISM: Thermotoga maritima

<400> SEQUENCE: 36

Lys Ile Arg Asp Lys Ile Leu Asn Val Tyr Thr Gln Phe Ser Pro Ala
1               5                   10                  15

Glu Arg Lys Val Ala Asp Tyr Val Leu Glu Arg Pro Asp Asp Val Ile
            20                  25                  30

His Tyr Ser Ile Thr Glu Phe Ala Lys Ile Val Gly Val Ser Glu Thr
        35                  40                  45

Thr Ile His Arg Met Ile Lys Lys Leu Asp Phe Glu Gly Tyr Gln Ala
    50                  55                  60

Phe Lys Ile Ala Leu Ala Arg Glu Leu Ser Gly Leu Glu Glu Thr Ile
65                  70                  75                  80

Glu Arg Arg Asp Phe Ile Asp Glu Glu Ile Asp Ile Leu Arg Arg Leu
                85                  90                  95

Lys Asp Thr Leu Asp
            100

<210> SEQ ID NO 37
<211> LENGTH: 60
<212> TYPE: PRT
<213> ORGANISM: Thermotoga maritima

<400> SEQUENCE: 37

Lys Arg Arg Pro Thr Ile Asn Asp Val Ala Lys Leu Ala Gly Val Ser
1               5                   10                  15

Ile Ser Thr Val Ser Arg Tyr Leu Lys Asp Pro Ser Gln Val Ser Glu
                20                  25                  30

Lys Leu Gly Glu Arg Ile Arg Glu Ala Ile Lys Leu Gly Tyr Lys
            35                  40                  45

Pro Asn Lys Ile Ala Gln Gly Leu Arg Thr Gly Asp
        50                  55                  60

<210> SEQ ID NO 38
<211> LENGTH: 58
<212> TYPE: PRT
<213> ORGANISM: Thermotoga maritima

<400> SEQUENCE: 38

Met Ala Ser Ile Lys Asp Val Ala Lys Leu Ala Gly Val Ser Ile Ala
1               5                   10                  15

Thr Val Ser Arg Val Ile Asn Gly Tyr Asn Asn Val Ser Glu Glu Thr
                20                  25                  30

Arg Lys Lys Val Ile Asp Ala Ile Arg Lys Leu Asn Tyr His Pro Val
            35                  40                  45

Tyr Ala Val Lys Gly Ala Val Leu Lys Arg
        50                  55

<210> SEQ ID NO 39
<211> LENGTH: 61
<212> TYPE: PRT
<213> ORGANISM: Thermotoga maritima

<400> SEQUENCE: 39

Met Lys Lys Lys Tyr Val Thr Ile Arg Asp Ile Ala Glu Lys Ala Gly
1               5                   10                  15

Val Ser Ile Asn Thr Val Ser Arg Ala Leu Asn Asn Lys Pro Asp Ile
                20                  25                  30

Ser Glu Glu Thr Arg Arg Lys Ile Leu Lys Ile Ala Gln Glu Leu Gly
            35                  40                  45

Tyr Val Lys Asn Ala Thr Ala Ser Ser Leu Arg Ser Lys
        50                  55                  60

<210> SEQ ID NO 40
<211> LENGTH: 58
<212> TYPE: PRT
<213> ORGANISM: Thermotoga

<400> SEQUENCE: 40

Met Pro Thr Ile Glu Asp Val Ala Lys Leu Ala Gly Val Ser Ile Ala
1               5                   10                  15

Thr Val Ser Arg Val Ile Asn Gly Ser Gly Tyr Val Ser Glu Lys Thr
                20                  25                  30

Arg Tyr Lys Val Trp Lys Ala Ile Glu Glu Leu Gly Tyr Lys Pro Glu
            35                  40                  45

Ile Ser Ala Lys Leu Leu Ala Ser Lys Gly
        50                  55

<210> SEQ ID NO 41
<211> LENGTH: 61
<212> TYPE: PRT

<213> ORGANISM: Thermotoga maritima

<400> SEQUENCE: 41

```
Met Arg Ile Gly Glu Lys Leu Arg Lys Leu Arg Leu Ser Arg Gly Leu
1               5                   10                  15

Thr Gln Glu Glu Leu Ala Glu Arg Thr Asp Leu Ser Arg Ser Phe Ile
                20                  25                  30

Ser Gln Leu Glu Ser Asp Lys Thr Ser Pro Ser Ile Asp Thr Leu Glu
            35                  40                  45

Arg Ile Leu Glu Ala Leu Gly Thr Asp Leu Lys His Phe
50                  55                  60
```

<210> SEQ ID NO 42
<211> LENGTH: 67
<212> TYPE: PRT
<213> ORGANISM: Thermotoga maritima

<400> SEQUENCE: 42

```
Met His Met Lys Thr Val Arg Gln Glu Arg Leu Lys Ser Ile Val Arg
1               5                   10                  15

Ile Leu Glu Arg Ser Lys Glu Pro Val Ser Gly Ala Gln Leu Ala Glu
                20                  25                  30

Glu Leu Ser Val Ser Arg Gln Val Ile Val Gln Asp Ile Ala Tyr Leu
            35                  40                  45

Arg Ser Leu Gly Tyr Asn Ile Val Ala Thr Pro Arg Gly Tyr Val Leu
50                  55                  60

Ala Gly Gly
65
```

<210> SEQ ID NO 43
<211> LENGTH: 75
<212> TYPE: PRT
<213> ORGANISM: Thermotoga maritima

<400> SEQUENCE: 43

```
Met Asn Thr Leu Lys Lys Ala Phe Glu Ile Leu Asp Phe Ile Val Lys
1               5                   10                  15

Asn Pro Gly Asp Val Ser Val Ser Glu Ile Ala Glu Lys Phe Asn Met
                20                  25                  30

Ser Val Ser Asn Ala Tyr Lys Tyr Met Val Val Leu Glu Glu Lys Gly
            35                  40                  45

Phe Val Leu Arg Lys Lys Asp Lys Arg Tyr Val Pro Gly Tyr Lys Leu
50                  55                  60

Ile Glu Tyr Gly Ser Phe Val Leu Arg Arg Phe
65                  70                  75
```

<210> SEQ ID NO 44
<211> LENGTH: 81
<212> TYPE: PRT
<213> ORGANISM: Thermotoga maritima

<400> SEQUENCE: 44

```
Met Lys Ile Ser Lys Lys Arg Arg Gln Glu Leu Ile Arg Lys Ile Ile
1               5                   10                  15

His Glu Lys Lys Ile Ser Asn Gln Phe Gln Ile Val Glu Glu Leu Lys
                20                  25                  30

Lys Tyr Gly Ile Lys Ala Val Gln Pro Thr Val Ala Arg Asp Leu Lys
            35                  40                  45
```

-continued

Glu Ile Gly Ala Val Lys Ile Met Asp Glu Ser Gly Asn Tyr Val Tyr
        50                  55                  60

Lys Leu Leu Asp Glu Thr Pro Val Ile Asp Pro Trp Lys Glu Leu Lys
65                  70                  75                  80

Arg

<210> SEQ ID NO 45
<211> LENGTH: 82
<212> TYPE: PRT
<213> ORGANISM: Thermotoga maritima

<400> SEQUENCE: 45

Met His Lys Lys Leu Asn Pro Lys Ser Met Lys Arg Glu Asn Lys Lys
1               5                   10                  15

Met Val Leu Arg Tyr Leu Ile Glu Ser Gly Pro His Ser Arg Val Glu
                20                  25                  30

Ile Ala Arg Lys Thr Gly Leu Ala Gln Ser Ala Ile Trp Arg Ile Ile
            35                  40                  45

Glu Glu Leu Val Asn Glu Gly Leu Val Glu Lys Gly Thr Ala Thr
        50                  55                  60

Gly Arg Arg Arg Lys Ala Val Thr Tyr Gly Pro Thr Arg Ser Phe Ile
65                  70                  75                  80

Thr Ser

<210> SEQ ID NO 46
<211> LENGTH: 79
<212> TYPE: PRT
<213> ORGANISM: Thermotoga maritima

<400> SEQUENCE: 46

Met Pro Ser Pro Leu Leu Arg Arg Glu Asn Lys Ile Lys Ile Leu Arg
1               5                   10                  15

Tyr Ile Leu Lys Asn Gly Lys Thr Thr Arg Asn Gln Leu Ala Ser Asn
                20                  25                  30

Leu Asn Leu Ala His Ser Thr Leu Ser Tyr Ile Ile Asp Glu Leu Leu
            35                  40                  45

Asp Glu Gly Phe Leu Val Phe Glu Gly Ile Lys Lys Arg Gly Arg
        50                  55                  60

Pro Tyr Gln Ile Leu Ser Val Asn Pro Glu Lys Phe Thr Ala Ile
65                  70                  75

<210> SEQ ID NO 47
<211> LENGTH: 79
<212> TYPE: PRT
<213> ORGANISM: Thermotoga maritima

<400> SEQUENCE: 47

Met Lys Glu Glu Arg Leu Lys Glu Ile Leu Asp Ile Val Asp Arg Asn
1               5                   10                  15

Gly Phe Ile Ser Met Lys Asp Leu Gln Glu Gln Leu Gly Val Ser Met
                20                  25                  30

Ile Thr Val Arg Arg Asp Val Ala Glu Leu Val Lys Arg Asn Leu Val
            35                  40                  45

Lys Lys Val His Gly Gly Ile Arg Lys Val Asn Tyr Phe Glu Lys Glu
        50                  55                  60

Thr Asp Phe Met Lys Arg Leu Ser Ile Asn Arg Glu Ala Lys Glu
65                  70                  75

<210> SEQ ID NO 48
<211> LENGTH: 137
<212> TYPE: PRT
<213> ORGANISM: Thermotoga maritima

<400> SEQUENCE: 48

Met Phe Thr Met Arg Ser Glu Tyr Ala Leu Arg Leu Met Ile Val Met
1               5                   10                  15

Ala Lys Glu Tyr Gly Asn Tyr Leu Ser Met Thr Glu Ile Leu Glu Lys
            20                  25                  30

Ala Lys Gln Ser Val Pro Arg Glu Phe Ala Glu Lys Ile Leu Tyr Thr
        35                  40                  45

Leu Lys Lys Ala Gly Leu Val Lys Thr Arg Arg Gly Lys Ser Gly Gly
    50                  55                  60

Tyr Met Leu Ser Arg Pro Pro Lys Glu Ile Lys Val Ser Glu Ile Val
65                  70                  75                  80

Phe Leu Leu Asp Arg Lys Ser Lys Val Phe Phe Asp Met Pro Gly Cys
                85                  90                  95

Pro Asp Glu Leu Asp Cys Val Ile Arg Ala Leu Trp Lys Arg Val Glu
            100                 105                 110

Asn Glu Ile Glu Lys Ile Leu Ser Gly Val Thr Leu Glu Asp Leu Val
        115                 120                 125

Arg Glu Gln Glu Lys Met Lys Gln
    130                 135

<210> SEQ ID NO 49
<211> LENGTH: 95
<212> TYPE: PRT
<213> ORGANISM: Thermotoga naphthophila

<400> SEQUENCE: 49

Met Arg Asp Thr Lys Gly His Leu Lys Phe Leu Val Leu His Ile Ile
1               5                   10                  15

Ser Gln Gln Pro Ser His Gly Tyr Tyr Ile Met Lys Lys Ile Ser Gln
            20                  25                  30

Ile Ile Gly Ala Glu Pro Pro Ser Pro Gly Ala Leu Tyr Pro Ile Leu
        35                  40                  45

Ser Ser Leu Arg Lys Gln Lys Tyr Ile Glu Thr Tyr Asn Glu Gly Lys
    50                  55                  60

Arg Lys Val Tyr Arg Leu Thr Asp Lys Gly Arg Lys Tyr Leu Glu Glu
65                  70                  75                  80

His Lys Glu Glu Ile Lys Lys Ala Leu Asp Phe Ala Glu Arg Phe
                85                  90                  95

<210> SEQ ID NO 50
<211> LENGTH: 118
<212> TYPE: PRT
<213> ORGANISM: Thermotoga maritima

<400> SEQUENCE: 50

Met Arg His Arg Gly Gly Arg Gly Phe Arg Gly Trp Trp Leu Ala Ser
1               5                   10                  15

Thr Ile Leu Leu Leu Val Ala Glu Lys Pro Ser His Gly Tyr Glu Leu
            20                  25                  30

Ala Glu Arg Leu Ala Glu Phe Gly Ile Glu Ile Pro Gly Ile Gly His
        35                  40                  45

Met Gly Asn Ile Tyr Arg Val Leu Ala Asp Leu Glu Glu Ser Gly Phe

|    |    |    |    |    | 50 |    |    |    |    | 55 |    |    |    |    | 60 |    |    |

Leu Ser Thr Glu Trp Asp Thr Thr Val Ser Pro Pro Arg Lys Ile Tyr
65                  70                  75                  80

Arg Ile Thr Pro Gln Gly Lys Leu Tyr Leu Arg Glu Ile Leu Arg Ser
                    85                  90                  95

Leu Glu Asp Met Lys Arg Arg Ile Glu Thr Leu Glu Glu Arg Ile Lys
                100                 105                 110

Arg Val Leu Gln Glu Glu
            115

<210> SEQ ID NO 51
<211> LENGTH: 70
<212> TYPE: PRT
<213> ORGANISM: Thermotoga maritima

<400> SEQUENCE: 51

Met Leu Ser Lys Arg Asp Ala Ile Leu Lys Ala Val Glu Val Phe
1               5                   10                  15

Gly Lys Lys Gly Tyr Asp Arg Ala Thr Thr Asp Glu Ile Ala Glu Lys
                20                  25                  30

Ala Gly Val Ala Lys Gly Leu Ile Phe His Tyr Phe Lys Asn Lys Glu
                35                  40                  45

Glu Leu Tyr Tyr Gln Ala Tyr Met Ser Val Thr Glu Lys Leu Gln Lys
            50                  55                  60

Glu Phe Glu Asn Phe Leu
65                  70

<210> SEQ ID NO 52
<211> LENGTH: 883
<212> TYPE: PRT
<213> ORGANISM: Enterobacteria bacteriophage 13a

<400> SEQUENCE: 52

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
                20                  25                  30

Ala Arg Glu Gln Leu Ala Leu Glu His Glu Ser Tyr Glu Met Gly Glu
            35                  40                  45

Ala Arg Phe Arg Lys Met Phe Glu Arg Gln Leu Lys Ala Gly Glu Val
        50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
                100                 105                 110

Ala Val Ala Tyr Ile Thr Ile Lys Thr Thr Leu Ala Cys Leu Thr Ser
            115                 120                 125

Val Asp Asn Thr Thr Val Gln Ala Val Ala Ser Ala Ile Gly Arg Ala
        130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser

```
            180                 185                 190
Lys Gly Leu Leu Gly Gly Glu Ala Trp Ser Ser Trp His Lys Glu Asp
            195                 200                 205
Ser Ile His Val Gly Val Arg Cys Ile Glu Met Leu Ile Glu Ser Thr
            210                 215                 220
Gly Met Val Ser Leu His Arg Gln Asn Ala Gly Val Val Gly Gln Asp
225                 230                 235                 240
Ser Glu Thr Ile Glu Leu Ala Pro Glu Tyr Ala Glu Ala Ile Ala Thr
            245                 250                 255
Arg Ala Gly Ala Leu Ala Gly Ile Ser Pro Met Phe Gln Pro Cys Val
            260                 265                 270
Val Pro Pro Lys Pro Trp Thr Gly Ile Thr Gly Gly Tyr Trp Ala
            275                 280                 285
Asn Gly Arg Arg Pro Leu Ala Leu Val Arg Thr His Ser Lys Lys Ala
            290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
            325                 330                 335
Val Ala Asn Val Ile Thr Lys Trp Lys His Cys Pro Val Glu Asp Ile
            340                 345                 350
Pro Ala Ile Glu Arg Glu Leu Pro Met Lys Pro Glu Asp Ile Asp
            355                 360                 365
Thr Asn Pro Asp Ala Leu Thr Ala Trp Lys Arg Ala Ala Ala Val
370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
            405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Asp Asn His Glu Asn Ile Met Ala Cys Ala Lys Ser Pro
            485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His Gly Leu Ser Tyr
            515                 520                 525
Asn Cys Ser Leu Pro Leu Ala Phe Asp Gly Ser Cys Ser Gly Ile Gln
            530                 535                 540
His Phe Ser Ala Met Leu Leu Asp Glu Ile Gly Gly Arg Ala Val Asn
545                 550                 555                 560
Leu Leu Pro Ser Glu Thr Val Gln Asp Ile Tyr Gly Ile Val Ala Lys
            565                 570                 575
Lys Val Asn Val Ile Leu Gln Ala Asp Val Ile Asn Gly Thr Asp Asn
            580                 585                 590
Glu Val Val Thr Val Thr Asp Glu Asn Thr Gly Glu Ile Ser Glu Lys
            595                 600                 605
```

```
Val Lys Leu Gly Thr Lys Ala Leu Ala Gly Gln Trp Leu Ala Tyr Gly
    610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ala Ser Val Thr
            675                 680                 685
Val Val Ala Ala Val Glu Ala Met Asn Trp Leu Lys Ser Ala Ala Lys
    690                 695                 700
Leu Leu Ala Ala Glu Val Lys Asp Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
    755                 760                 765
Ile Asp Ala His Lys Gln Glu Ser Gly Ile Ala Pro Asn Phe Val His
770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
            835                 840                 845
Phe Ala Asp Gln Leu His Glu Ser Gln Leu Asp Lys Met Pro Ala Leu
    850                 855                 860
Pro Ala Lys Gly Asn Leu Asn Leu Gln Asp Ile Leu Lys Ser Asp Phe
865                 870                 875                 880
Ala Phe Ala

<210> SEQ ID NO 53
<211> LENGTH: 883
<212> TYPE: PRT
<213> ORGANISM: Yersinia bacteriophage YpP-R

<400> SEQUENCE: 53

Met Asn Thr Ile Asn Ile Ala Lys Asn Asp Phe Ser Asp Ile Glu Leu
1               5                   10                  15
Ala Ala Ile Pro Phe Asn Thr Leu Ala Asp His Tyr Gly Glu Arg Leu
            20                  25                  30
Ala Arg Glu Gln Leu Ala Leu Glu His Glu Ser Tyr Glu Met Gly Glu
        35                  40                  45
Ala Arg Phe Arg Lys Met Phe Glu Arg Gln Leu Lys Ala Gly Glu Val
    50                  55                  60
Ala Asp Asn Ala Ala Ala Lys Pro Leu Ile Thr Thr Leu Leu Pro Lys
65                  70                  75                  80
Met Ile Ala Arg Ile Asn Asp Trp Phe Glu Glu Val Lys Ala Lys Arg
                85                  90                  95
```

```
Gly Lys Arg Pro Thr Ala Phe Gln Phe Leu Gln Ile Lys Pro Glu
            100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Gln Leu Asn Lys Arg Val Gly His
                165                 170                 175

Val Tyr Lys Lys Ala Phe Met Gln Val Glu Ala Asp Met Leu Ser
                180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
            210                 215                 220

Gly Met Val Asn Leu His Arg Gln Asn Ala Gly Val Val Gly Gln Asp
225                 230                 235                 240

Ser Glu Thr Ile Glu Leu Thr Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
            355                 360                 365

Thr Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Asp Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510
```

Ala Phe Cys Phe Glu Tyr Ala Gly Val Gln His His Gly Leu Ser Tyr
515                 520                 525

Asn Cys Ser Leu Pro Leu Ala Phe Asp Gly Ser Cys Ser Gly Ile Gln
530                 535                 540

His Phe Ser Ala Met Leu Leu Asp Glu Val Gly Gly Leu Ala Val Asn
545                 550                 555                 560

Leu Leu Pro Ser Ala Thr Val Gln Asp Ile Tyr Gly Ile Val Ala Lys
                565                 570                 575

Lys Val Asn Val Ile Leu Gln Ala Asp Val Ile Asn Gly Thr Asp Asn
                580                 585                 590

Glu Val Val Thr Val Thr Asp Glu Asn Thr Gly Glu Ile Ser Glu Lys
595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ala Val Ser Val Thr
                675                 680                 685

Val Val Ala Ala Val Glu Ala Met Asn Trp Leu Lys Ser Ala Ala Lys
690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
                755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
850                 855                 860

Pro Ala Lys Gly Asn Leu Asn Leu Gln Asp Ile Leu Lys Ser Asp Phe
865                 870                 875                 880

Ala Phe Ala

<210> SEQ ID NO 54
<211> LENGTH: 883
<212> TYPE: PRT
<213> ORGANISM: Yersinia bacteriophage R

<400> SEQUENCE: 54

-continued

```
Met Asn Thr Ile Asn Ile Ala Lys Asn Asp Phe Ser Asp Ile Glu Leu
 1               5                  10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
         35                  40                  45

Ala Arg Phe Arg Lys Met Phe Glu Arg Gln Leu Lys Ala Gly Glu Val
     50                  55                  60

Ala Asp Asn Ala Ala Lys Pro Leu Ile Thr Leu Leu Pro Lys
 65              70                  75                  80

Met Ile Ala Arg Ile Asn Asp Trp Phe Glu Glu Val Lys Ala Lys Arg
                 85                  90                  95

Gly Lys Arg Pro Thr Ala Phe Gln Phe Leu Gln Glu Ile Lys Pro Glu
             100                 105                 110

Ala Val Ala Tyr Ile Thr Ile Lys Thr Thr Leu Ala Cys Leu Thr Ser
         115                 120                 125

Ala Asp Asn Thr Thr Val Gln Ala Val Ala Ser Ala Ile Gly Arg Ala
     130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                 165                 170                 175

Val Tyr Lys Lys Ala Phe Met Gln Val Val Glu Ala Asp Met Leu Ser
             180                 185                 190

Lys Gly Leu Leu Gly Gly Glu Ala Trp Ser Ser Trp His Lys Glu Asp
         195                 200                 205

Ser Ile His Val Gly Val Arg Cys Ile Glu Met Leu Ile Glu Ser Thr
     210                 215                 220

Gly Met Val Asn Leu His Arg Gln Asn Ala Gly Val Val Gly Gln Asp
225                 230                 235                 240

Ser Glu Thr Ile Glu Leu Thr Pro Glu Tyr Ala Glu Ala Ile Ala Thr
                 245                 250                 255

Arg Ala Gly Ala Leu Ala Gly Ile Ser Pro Met Phe Gln Pro Cys Val
             260                 265                 270

Val Pro Pro Lys Pro Trp Thr Gly Ile Thr Gly Gly Gly Tyr Trp Ala
         275                 280                 285

Asn Gly Arg Arg Pro Leu Ala Leu Val Arg Thr His Ser Lys Lys Ala
     290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                 325                 330                 335

Val Ala Asn Val Ile Thr Lys Trp Lys His Cys Pro Val Glu Asp Ile
             340                 345                 350

Pro Ala Ile Glu Arg Glu Glu Leu Pro Met Lys Pro Glu Asp Ile Asp
         355                 360                 365

Thr Asn Pro Glu Ala Leu Thr Ala Trp Lys Arg Ala Ala Ala Val
     370                 375                 380

Tyr Arg Lys Asp Lys Arg Lys Ser Arg Arg Ile Ser Leu Glu Phe
385                 390                 395                 400

Met Leu Glu Gln Ala Asn Lys Phe Ala Asn His Lys Ala Ile Trp Phe
                 405                 410                 415

Pro Tyr Asn Met Asp Trp Arg Gly Arg Val Tyr Ala Val Ser Met Phe
```

```
            420                 425                 430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Asp Asn His Glu Asn Ile Met Ala Cys Ala Lys Ser Pro
                    485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
            530                 535                 540
His Phe Ser Ala Met Leu Leu Asp Glu Val Gly Gly Leu Ala Val Asn
545                 550                 555                 560
Leu Leu Pro Ser Ala Thr Val Gln Asp Ile Tyr Gly Ile Val Ala Lys
                    565                 570                 575
Lys Val Asn Val Ile Leu Gln Ala Asp Val Ile Asn Gly Thr Asp Asn
                    580                 585                 590
Glu Val Val Thr Val Thr Asp Glu Asn Thr Gly Glu Ile Pro Glu Lys
            595                 600                 605
Val Lys Leu Gly Thr Lys Ala Leu Ala Gly Gln Trp Leu Ala Tyr Gly
            610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                    645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ala Val Ser Val Thr
            675                 680                 685
Val Val Ala Ala Val Glu Ala Met Asn Trp Leu Lys Ser Ala Ala Lys
            690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                    725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
            755                 760                 765
Ile Asp Ala His Lys Gln Glu Ser Gly Ile Ala Pro Asn Phe Val His
            770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                    805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
            835                 840                 845
```

```
Phe Ala Asp Gln Leu His Glu Ser Gln Leu Asp Lys Met Pro Ala Leu
            850                 855                 860

Pro Ala Lys Gly Asn Leu Asn Leu Gln Asp Ile Leu Lys Ser Asp Phe
865                 870                 875                 880

Ala Phe Ala

<210> SEQ ID NO 55
<211> LENGTH: 883
<212> TYPE: PRT
<213> ORGANISM: Yersinia bacteriophage phiA1122

<400> SEQUENCE: 55

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Asn Leu His Arg Gln Asn Ala Gly Val Val Gly Gln Asp
225                 230                 235                 240

Ser Glu Thr Ile Glu Leu Thr Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335
```

```
Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Thr Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Asp Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Leu Asp Glu Val Gly Gly Leu Ala Val Asn
545                 550                 555                 560

Leu Leu Pro Ser Ala Thr Val Gln Asp Ile Tyr Gly Ile Val Ala Lys
                565                 570                 575

Lys Val Asn Val Ile Leu Gln Ala Asp Val Ile Asn Gly Thr Asp Asn
            580                 585                 590

Glu Val Val Thr Val Thr Asp Glu Asn Thr Gly Glu Ile Pro Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ala Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750
```

```
Gly Gln Phe Arg Leu Gln Pro Thr Ile Asn Thr Asn Lys Asp Ser Glu
            755                 760                 765
Ile Asp Ala His Lys Gln Glu Ser Gly Ile Ala Pro Asn Phe Val His
770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
                820                 825                 830
Val Asp Thr Tyr Glu Ser Cys Asp Val Leu Ala Asp Phe Tyr Asp Gln
            835                 840                 845
Phe Ala Asp Gln Leu His Glu Ser Gln Leu Asp Lys Met Pro Ala Leu
850                 855                 860
Pro Ala Lys Gly Asn Leu Asn Leu Gln Asp Ile Leu Lys Ser Asp Phe
865                 870                 875                 880
Ala Phe Ala

<210> SEQ ID NO 56
<211> LENGTH: 883
<212> TYPE: PRT
<213> ORGANISM: Escherichia bacteriophage CICC 80001

<400> SEQUENCE: 56

Met Asn Thr Ile Asn Ile Ala Lys Asn Asp Phe Ser Asp Ile Glu Leu
1               5                   10                  15
Ala Ala Ile Pro Phe Asn Thr Leu Ala Asp His Tyr Gly Glu Arg Leu
                20                  25                  30
Ala Arg Glu Gln Leu Ala Leu Glu His Glu Ser Tyr Glu Met Gly Glu
            35                  40                  45
Ala Arg Phe Arg Lys Met Phe Glu Arg Gln Leu Lys Ala Gly Glu Val
        50                  55                  60
Ala Asp Asn Ala Ala Ala Lys Pro Leu Ile Thr Thr Leu Leu Pro Lys
65                  70                  75                  80
Met Ile Ala Arg Ile Asn Asp Trp Phe Glu Val Val Lys Ala Lys Arg
                85                  90                  95
Gly Lys Arg Pro Thr Ala Phe Gln Phe Leu Gln Glu Ile Lys Pro Glu
            100                 105                 110
Ala Val Ala Tyr Ile Thr Ile Lys Thr Thr Leu Ala Cys Leu Thr Ser
        115                 120                 125
Ala Asp Asn Thr Thr Val Gln Ala Val Ala Ser Ala Ile Gly Arg Ala
130                 135                 140
Ile Glu Asp Glu Ser Arg Phe Gly Arg Ile Arg Asp Leu Glu Ala Lys
145                 150                 155                 160
His Phe Lys Lys Asn Val Glu Glu Gln Leu Asn Lys Arg Val Gly His
                165                 170                 175
Val Tyr Arg Lys Ala Phe Met Gln Val Val Glu Ala Asp Met Leu Ser
            180                 185                 190
Lys Gly Leu Met Gly Gly Glu Ala Trp Ser Ser Trp His Lys Glu Asp
        195                 200                 205
Ser Ile His Val Gly Val Arg Cys Ile Glu Met Leu Ile Glu Ser Thr
210                 215                 220
Gly Met Val Ser Leu His Arg Gln Asn Ala Gly Val Val Gly Gln Asp
225                 230                 235                 240
```

-continued

Ser Glu Thr Ile Glu Leu Ala Pro Glu Tyr Ala Glu Ile Ala Thr
            245                 250                 255

Arg Ala Gly Ala Leu Ala Gly Ile Ser Pro Met Phe Gln Pro Cys Val
        260                 265                 270

Val Pro Pro Lys Pro Trp Thr Gly Ile Thr Gly Gly Tyr Trp Ala
    275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Thr Asn Pro Glu Ala Leu Thr Ala Trp Lys Arg Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ser Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Asp Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Leu Ala Val Asn
545                 550                 555                 560

Leu Leu Pro Ser Glu Thr Val Gln Asp Ile Tyr Gly Ile Val Ala Lys
                565                 570                 575

Lys Val Asn Val Ile Leu Gln Glu Asp Val Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln

```
                        660                 665                 670
Ala Ala Gly Tyr Met Ala Lys Leu Ile Trp Glu Ala Val Ser Val Thr
                675                 680                 685

Val Val Ala Ala Val Glu Ala Met Asn Trp Leu Lys Ser Ala Ala Lys
        690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                    725                 730                 735

Gln Glu Tyr Lys Lys Pro Ile Gln Thr Arg Leu Asn Leu Ile Phe Leu
                740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
        770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                    805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
        850                 855                 860

Pro Ala Lys Gly Asn Leu Asn Leu Gln Asp Ile Leu Lys Ser Asp Phe
865                 870                 875                 880

Ala Phe Ala

<210> SEQ ID NO 57
<211> LENGTH: 903
<212> TYPE: PRT
<213> ORGANISM: Yersinia bacteriophage YpsP-G

<400> SEQUENCE: 57

Met Thr Glu Arg Thr Asp Gly Leu Lys Lys Gly Tyr Met Pro Asn Gly
1               5                   10                  15

Thr Leu Tyr Ala Ala Asn Arg Arg Leu Val Arg Thr Trp Arg Glu Asn
                20                  25                  30

Asn Leu Glu Leu Ala Ala Ile Pro Phe Asn Thr Leu Ala Asp His Tyr
            35                  40                  45

Gly Glu Arg Leu Ala Arg Glu Gln Leu Ala Leu Glu His Glu Ser Tyr
        50                  55                  60

Glu Met Gly Glu Ala Arg Phe Arg Lys Met Phe Glu Arg Gln Leu Lys
65                  70                  75                  80

Ala Gly Glu Val Ala Asp Asn Ala Ala Lys Pro Leu Ile Thr Thr
                85                  90                  95

Leu Leu Pro Lys Met Ile Ala Arg Ile Asn Asp Trp Phe Glu Glu Val
                100                 105                 110

Lys Ala Lys Arg Gly Lys Arg Pro Thr Ala Phe Gln Phe Leu Gln Glu
            115                 120                 125

Ile Lys Pro Glu Ala Val Ala Tyr Ile Thr Ile Lys Thr Thr Leu Ala
        130                 135                 140

Cys Leu Thr Ser Ala Asp Asn Thr Thr Val Gln Ala Val Ala Ser Ala
```

```
            145                 150                 155                 160
    Ile Gly Arg Ala Ile Glu Asp Glu Ala Arg Phe Gly Arg Ile Arg Asp
                    165                 170                 175

Leu Glu Ala Lys His Phe Lys Lys Asn Val Glu Glu Gln Leu Asn Lys
                    180                 185                 190

Arg Val Gly His Val Tyr Lys Lys Ala Phe Met Gln Val Glu Ala
                    195                 200                 205

Asp Met Leu Ser Lys Gly Leu Leu Gly Gly Ala Trp Ser Ser Trp
        210                 215                 220

His Lys Glu Asp Ser Ile His Val Gly Val Arg Cys Ile Glu Met Leu
    225                 230                 235                 240

Ile Glu Ser Thr Gly Met Val Asn Leu His Arg Gln Asn Ala Gly Val
                    245                 250                 255

Val Gly Gln Asp Ser Glu Thr Ile Glu Leu Thr Pro Glu Tyr Ala Glu
                    260                 265                 270

Ala Ile Ala Thr Arg Ala Gly Ala Leu Ala Gly Ile Ser Pro Met Phe
                    275                 280                 285

Gln Pro Cys Val Val Pro Pro Lys Pro Trp Thr Gly Ile Thr Gly Gly
        290                 295                 300

Gly Tyr Trp Ala Asn Gly Arg Arg Pro Leu Ala Leu Val Arg Thr His
    305                 310                 315                 320

Ser Lys Lys Ala Leu Met Arg Tyr Glu Asp Val Tyr Met Pro Glu Val
                    325                 330                 335

Tyr Lys Ala Ile Asn Ile Ala Gln Asn Thr Ala Trp Lys Ile Asn Lys
                    340                 345                 350

Lys Val Leu Ala Val Ala Asn Val Ile Thr Lys Trp Lys His Cys Pro
                    355                 360                 365

Val Glu Asp Ile Pro Ala Ile Glu Arg Glu Leu Pro Met Lys Pro
        370                 375                 380

Glu Asp Ile Asp Thr Asn Pro Glu Ala Leu Thr Ala Trp Lys Arg Ala
    385                 390                 395                 400

Ala Ala Ala Val Tyr Arg Lys Asp Lys Ala Arg Lys Ser Arg Arg Ile
                    405                 410                 415

Ser Leu Glu Phe Met Leu Glu Gln Ala Asn Lys Phe Ala Asn His Lys
                    420                 425                 430

Ala Ile Trp Phe Pro Tyr Asn Met Asp Trp Arg Gly Arg Val Tyr Ala
                    435                 440                 445

Val Ser Met Phe Asn Pro Gln Gly Asn Asp Met Thr Lys Gly Leu Leu
        450                 455                 460

Thr Leu Ala Lys Gly Lys Pro Ile Gly Lys Glu Gly Tyr Tyr Trp Leu
    465                 470                 475                 480

Lys Ile His Gly Ala Asn Cys Ala Gly Val Asp Lys Val Pro Phe Pro
                    485                 490                 495

Glu Arg Ile Lys Phe Ile Glu Asp Asn His Glu Asn Ile Met Ala Cys
                    500                 505                 510

Ala Lys Ser Pro Leu Glu Asn Thr Trp Trp Ala Glu Gln Asp Ser Pro
                    515                 520                 525

Phe Cys Phe Leu Ala Phe Cys Phe Glu Tyr Ala Gly Val Gln His His
        530                 535                 540

Gly Leu Ser Tyr Asn Cys Ser Leu Pro Leu Ala Phe Asp Gly Ser Cys
    545                 550                 555                 560

Ser Gly Ile Gln His Phe Ser Ala Met Leu Leu Asp Glu Val Gly Gly
                    565                 570                 575
```

Leu Ala Val Asn Leu Leu Pro Ser Ala Thr Val Gln Asp Ile Tyr Gly
            580                 585                 590

Ile Val Ala Lys Lys Val Asn Val Ile Leu Gln Ala Asp Val Ile Asn
        595                 600                 605

Gly Thr Asp Asn Glu Val Val Thr Val Thr Asp Glu Asn Thr Gly Glu
610                 615                 620

Ile Ser Glu Lys Val Lys Leu Gly Thr Lys Ala Leu Ala Gly Gln Trp
625                 630                 635                 640

Leu Ala Tyr Gly Val Thr Arg Ser Val Thr Lys Arg Ser Val Met Thr
            645                 650                 655

Leu Ala Tyr Gly Ser Lys Glu Phe Gly Phe Arg Gln Gln Val Leu Glu
            660                 665                 670

Asp Thr Ile Gln Pro Val Ile Asp Ser Gly Lys Gly Leu Met Phe Thr
        675                 680                 685

Gln Pro Asn Gln Ala Ala Gly Tyr Met Ala Lys Leu Ile Trp Glu Ala
    690                 695                 700

Val Ser Val Thr Val Ala Ala Val Glu Ala Met Asn Trp Leu Lys
705                 710                 715                 720

Ser Ala Ala Lys Leu Leu Ala Ala Glu Val Lys Asp Lys Lys Thr Gly
            725                 730                 735

Glu Ile Leu Arg Lys Arg Cys Ala Val His Trp Val Thr Pro Asp Gly
            740                 745                 750

Phe Pro Val Trp Gln Glu Tyr Lys Lys Pro Ile Gln Thr Arg Leu Asn
        755                 760                 765

Leu Met Phe Leu Gly Gln Phe Arg Leu Gln Pro Thr Ile Asn Thr Asn
    770                 775                 780

Lys Asp Ser Glu Ile Asp Ala His Lys Gln Glu Ser Gly Ile Ala Pro
785                 790                 795                 800

Asn Phe Val His Ser Gln Asp Gly Ser His Leu Arg Lys Thr Val Val
            805                 810                 815

Trp Ala His Glu Lys Tyr Gly Ile Glu Ser Phe Ala Leu Ile His Asp
            820                 825                 830

Ser Phe Gly Thr Ile Pro Ala Asp Ala Ala Asn Leu Phe Lys Ala Val
        835                 840                 845

Arg Glu Thr Met Val Asp Thr Tyr Glu Ser Cys Asp Val Leu Ala Asp
850                 855                 860

Phe Tyr Asp Gln Phe Ala Asp Gln Leu His Glu Ser Gln Leu Asp Lys
865                 870                 875                 880

Met Pro Ala Leu Pro Ala Lys Gly Asn Leu Asn Leu Gln Asp Ile Leu
            885                 890                 895

Lys Ser Asp Phe Ala Phe Ala
            900

<210> SEQ ID NO 58
<211> LENGTH: 883
<212> TYPE: PRT
<213> ORGANISM: Salmonella bacteriophage Vi06

<400> SEQUENCE: 58

Met Asn Thr Ile Ser Ile Thr Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu

```
              35                  40                  45
Val Arg Phe Arg Lys Met Phe Glu Arg Gln Leu Lys Ala Gly Glu Ile
 50                  55                  60

Ala Asp Asn Asp Ala Thr Lys Pro Leu Ile Thr Thr Leu Leu Pro Lys
 65                  70                  75                  80

Met Ile Ala Arg Ile Asn Ser Trp Phe Lys Glu Val Gln Ala Lys Cys
                 85                  90                  95

Gly Lys Arg Pro Thr Ala Phe Gln Phe Leu Gln Gly Ile Lys Pro Glu
                100                 105                 110

Ala Ile Ala Tyr Ile Thr Ile Lys Thr Thr Leu Ala Arg Leu Thr Ser
                115                 120                 125

Met Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Ile Glu Ala Asp Met Leu Ser
                180                 185                 190

Lys Gly Leu Leu Gly Gly Glu Ser Trp Ser Ser Trp His Lys Glu Asp
                195                 200                 205

Ser Ile His Val Gly Val Arg Cys Ile Glu Met Leu Ile Glu Ser Thr
                210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Ser Ile Ser Gly Gly Gly Tyr Trp Ala
                275                 280                 285

Asn Gly Arg Arg Pro Leu Ala Leu Val Arg Thr His Ser Lys Lys Ala
                290                 295                 300

Leu Met Arg Tyr Ala Asp Val Tyr Met Pro Glu Val Tyr Lys Ala Val
305                 310                 315                 320

Asn Ile Ala Gln Asn Thr Ala Trp Arg Ile Asn Lys Lys Val Leu Ala
                325                 330                 335

Val Ala Asn Val Val Thr Lys Trp Lys His Cys Pro Val Asp Tyr Ile
                340                 345                 350

Pro Thr Ile Glu Arg Glu Glu Leu Pro Met Lys Pro Glu Asp Ile Asp
                355                 360                 365

Thr Asn Pro Glu Ala Leu Ala Ser Trp Lys Arg Ala Ala Ala Ala Val
                370                 375                 380

Tyr Arg Lys Asp Lys Ala Arg Lys Ser Arg Arg Met Ser Leu Glu Phe
385                 390                 395                 400

Met Leu Glu Gln Ala Asn Lys Phe Ala Asn His Arg Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Phe Tyr Trp Leu Lys Ile His Gly
450                 455                 460
```

```
Ala Asn Cys Ala Gly Val Asp Lys Val Pro Phe Pro Glu Arg Ile Lys
465                 470                 475                 480

Phe Ile Glu Asp Asn His Glu Asn Ile Leu Ala Cys Ala Lys Ser Pro
            485                 490                 495

Leu Glu Asn Thr Trp Trp Ser Glu Gln Asp Ser Pro Phe Cys Phe Leu
                500                 505                 510

Ala Phe Cys Phe Glu Tyr Ala Gly Gly Gln His His Gly Leu Ser Tyr
            515                 520                 525

Asn Cys Ser Leu Pro Leu Ala Phe Asp Gly Ser Cys Phe Gly Ile Gln
            530                 535                 540

His Phe Ser Val Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Val Asp Met Ile Asn Gly Thr Asp Asn
                580                 585                 590

Glu Val Thr Val Thr Asp Asp Lys Thr Gly Glu Ile Tyr Glu Lys
                595                 600                 605

Ile Lys Leu Gly Thr Lys Glu Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr His Pro Asn Gln
                660                 665                 670

Ala Ala Gly Tyr Met Ala Lys Leu Ile Trp Glu Ala Val Ser Val Thr
                675                 680                 685

Val Val Ala Ala Val Glu Ala Met Asn Trp Leu Lys Ser Ala Ala Lys
                690                 695                 700

Leu Leu Ala Val Glu Val Lys Asp Arg Lys Thr Gly Glu Ile Leu Arg
705                 710                 715                 720

Lys Arg Cys Ala Val His Trp Thr Thr Pro Asp Gly Phe Pro Val Trp
                725                 730                 735

Gln Glu Tyr Lys Lys Pro Val Gln Thr Arg Leu Asn Leu Ile Phe Leu
                740                 745                 750

Gly Gln Phe Arg Leu Gln Pro Thr Ile Asn Thr Asn Arg Asp Ser Glu
                755                 760                 765

Ile Asp Ala Tyr Lys Gln Glu Ser Gly Ile Ala Pro Asn Phe Val His
                770                 775                 780

Ser Gln Asp Gly Ser His Leu Arg Lys Thr Val Val Trp Ala His Glu
785                 790                 795                 800

Lys Tyr Gly Ile Asp Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Ala Thr Tyr Glu Ser Cys Asp Val Leu Ala Asp Phe Tyr Ala Gln
                835                 840                 845

Phe Ala Asp Gln Leu His Lys Ser Gln Leu Lys Met Pro Val Leu
                850                 855                 860

Pro Ser Lys Gly Asn Leu Asn Leu Gln Asp Ile Leu Lys Ser Asp Phe
865                 870                 875                 880
```

Ala Phe Ala

<210> SEQ ID NO 59
<211> LENGTH: 883
<212> TYPE: PRT
<213> ORGANISM: Stenotrophomonas bacteriophage IME15

<400> SEQUENCE: 59

```
Met Thr Val Ile Ala Ile Glu Lys Asn Asp Phe Ser Asp Val Glu Leu
1               5                   10                  15

Ala Val Ile Pro Phe Asn Thr Leu Ala Asp His Tyr Gly Glu Lys Leu
            20                  25                  30

Ala Arg Glu Gln Leu Ala Leu Glu His Glu Ala Tyr Glu Met Gly Glu
        35                  40                  45

Ala Arg Phe Arg Lys Ile Phe Glu Arg Gln Leu Lys Ala Gly Glu Val
    50                  55                  60

Ala Asp Asn Ala Ala Ala Lys Pro Leu Val Ala Thr Leu Leu Pro Lys
65                  70                  75                  80

Met Ile Glu Arg Ile His Ala Trp Phe Glu Glu Val Ser Ala Lys Arg
                85                  90                  95

Gly Lys Arg Pro Thr Ala Phe Lys Phe Leu Gln Glu Val Lys Pro Glu
            100                 105                 110

Ala Ile Ala Tyr Ile Thr Ile Lys Thr Val Leu Gly Thr Leu Thr Ser
        115                 120                 125

Ala Glu Gln Thr Thr Val Gln Ala Ala Ala Ser Ala Val Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Leu Gln Val Val Glu Ala Asp Met Leu Ser
            180                 185                 190

Lys Gly Leu Met Gly Gly Glu Ala Trp Ser Ser Trp His Lys Glu Asp
        195                 200                 205

Ser Ile His Val Gly Val Arg Cys Ile Glu Met Leu Ile Glu Ala Thr
    210                 215                 220

Gly Leu Val Val Leu Glu Arg Gln Asn Ala Gly Val Val Gly Ala Asp
225                 230                 235                 240

Ala Glu Thr Leu Ser Leu Ala Ser Glu Tyr Ala Asp Ala Ile Ala Thr
                245                 250                 255

Arg Ala Gly Ala Leu Ala Gly Ile Ser Pro Met Tyr Gln Pro Cys Val
            260                 265                 270

Val Pro Pro Lys Pro Trp Thr Thr Val Thr Gly Gly Gly Tyr Trp Ala
        275                 280                 285

Asn Gly Arg Arg Pro Leu Ala Leu Val Arg Thr His Gly Lys Lys Ala
    290                 295                 300

Leu Met Arg Tyr Glu Asp Val Tyr Met Pro Glu Val Tyr Lys Ala Val
305                 310                 315                 320

Asn Leu Ala Gln Ser Thr Ala Trp Lys Ile Asn Lys Lys Val Leu Ala
                325                 330                 335

Val Ala Asn Glu Ile Thr Lys Trp Lys His Cys Pro Val Glu Asp Ile
            340                 345                 350

Pro Ala Ile Glu Arg Glu Glu Leu Pro Val Lys Pro Asp Asp Ile Asp
        355                 360                 365
```

```
Glu Asn Pro Glu Ala Leu Thr Asn Trp Lys Arg Ala Ala Ala Val
    370                 375                 380

Tyr Arg Lys Asp Lys Ala Arg Lys Ser Arg Arg Leu Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
                435                 440                 445

Gly Lys Ala Ile Gly Lys Glu Gly Phe Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Asp Asn His Glu His Ile Met Ala Ser Ala Lys Asn Pro
                485                 490                 495

Leu Glu Tyr Thr Trp Trp Ala Glu Gln Asp Ser Pro Phe Cys Phe Leu
                500                 505                 510

Ala Phe Cys Phe Glu Tyr Ala Gly Val Met His His Gly Leu Ser Tyr
            515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Met Gln Arg Asp Val Ile Ser Gly Thr Asp Asp
                580                 585                 590

Glu Leu Val Thr Glu Thr Asp Lys Thr Thr Gly Glu Ile Thr Glu Lys
                595                 600                 605

Ala Val Leu Gly Thr Arg Thr Leu Ala Gly Gln Trp Leu Ala Tyr Gly
                610                 615                 620

Ala Asn Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Arg
                645                 650                 655

Pro Ala Ile Asp Ser Gly Lys Gly Leu Met Phe Thr Ile Pro Asn Gln
                660                 665                 670

Ala Ala Gly Tyr Met Ala Lys Leu Ile Trp Asp Ser Val Ser Val Thr
            675                 680                 685

Val Val Ala Ala Val Glu Ala Met Lys Trp Leu Gln Ser Ala Ala Lys
            690                 695                 700

Leu Leu Ala Ala Glu Val Lys Asp Lys Lys Thr Gly Glu Val Leu Arg
705                 710                 715                 720

Asn Arg Cys Ala Val His Trp Val Thr Pro Asp Gly Phe Pro Val Trp
                725                 730                 735

Gln Glu Tyr Arg Lys Pro Leu Gln Thr Arg Leu Asn Leu Met Phe Leu
                740                 745                 750

Gly Gln Phe Arg Leu Gln Pro Thr Ile Asn Thr Asn Lys Asp Ser Gly
                755                 760                 765

Ile Asp Ala His Lys Gln Glu Ser Gly Ile Ala Pro Asn Phe Val His
                770                 775                 780

Ser Gln Asp Gly Ser His Leu Arg Lys Thr Val Val Trp Ala His Glu
```

```
                785                 790                 795                 800
Lys Tyr Gly Ile Glu Ser Phe Ala Leu Ile His Asp Ser Phe Gly Thr
                    805                 810                 815

Ile Pro Ala Asp Ala Gly Asn Leu Phe Lys Ala Val Arg Glu Thr Met
                    820                 825                 830

Val Asp Thr Tyr Glu Asn Cys Asp Val Leu Ala Asp Phe Tyr Glu Gln
                    835                 840                 845

Phe Ala Asp Gln Leu His Glu Ser Gln Leu Asp Lys Met Pro Ala Leu
850                 855                 860

Pro Lys Lys Gly Asn Leu Asn Leu Arg Asp Ile Leu Glu Ser Asp Phe
865                 870                 875                 880

Ala Phe Ala

<210> SEQ ID NO 60
<211> LENGTH: 884
<212> TYPE: PRT
<213> ORGANISM: Citrobacter bacteriophage SH2

<400> SEQUENCE: 60

Met Asn Ile Ile Glu Asn Ile Glu Lys Asn Asp Phe Ser Glu Ile Glu
1               5                   10                  15

Leu Ala Ala Ile Pro Phe Asn Thr Leu Ala Asp His Tyr Gly Ser Ala
                20                  25                  30

Leu Ala Arg Glu Gln Leu Ala Leu Glu His Glu Ser Tyr Glu Leu Gly
            35                  40                  45

Glu Arg Arg Phe Leu Lys Met Leu Glu Arg Gln Ala Lys Ala Gly Glu
        50                  55                  60

Ile Ala Asp Asn Ala Ala Ala Lys Pro Leu Leu Ala Thr Leu Leu Pro
65                  70                  75                  80

Lys Leu Thr Ala Arg Ile Val Glu Trp Leu Glu Glu Tyr Ala Ser Lys
                85                  90                  95

Lys Gly Arg Lys Pro Val Ala Tyr Ala Pro Leu Gln Leu Leu Lys Pro
            100                 105                 110

Glu Ala Ser Ala Phe Ile Thr Leu Lys Val Ile Leu Ala Ser Leu Thr
        115                 120                 125

Ser Thr Asn Met Thr Thr Ile Gln Ala Ala Gly Met Leu Gly Lys
130                 135                 140

Ala Ile Glu Asp Glu Ala Arg Phe Gly Arg Ile Arg Asp Leu Glu Ala
145                 150                 155                 160

Lys His Phe Lys Lys His Val Glu Glu Gln Leu Asn Lys Arg His Gly
                165                 170                 175

Gln Val Tyr Lys Lys Ala Phe Met Gln Val Val Glu Ala Asp Met Ile
            180                 185                 190

Gly Arg Gly Leu Leu Gly Gly Glu Ala Trp Ser Ser Trp Asp Lys Glu
        195                 200                 205

Thr Thr Met His Val Gly Ile Arg Leu Ile Glu Met Leu Ile Glu Ser
    210                 215                 220

Thr Gly Leu Val Glu Leu Gln Arg His Asn Ala Gly Asn Ala Gly Ser
225                 230                 235                 240

Asp His Glu Ala Leu Gln Leu Ala Gln Glu Tyr Val Asp Val Leu Ala
                245                 250                 255

Lys Arg Ala Gly Ala Leu Ala Gly Ile Ser Pro Met Phe Gln Pro Cys
            260                 265                 270

Val Val Pro Pro Lys Pro Trp Val Ser Ile Thr Gly Gly Gly Tyr Trp
```

```
            275                 280                 285
Ala Asn Gly Arg Arg Pro Leu Ala Leu Val Arg Thr His Ser Lys Lys
290                 295                 300

Gly Leu Met Arg Tyr Glu Asp Val Tyr Met Pro Glu Val Tyr Lys Ala
305                 310                 315                 320

Val Asn Ile Ala Gln Asn Thr Ala Trp Lys Ile Asn Lys Lys Val Leu
            325                 330                 335

Ala Val Val Asn Glu Ile Val Asn Trp Lys Asn Cys Pro Val Ala Asp
            340                 345                 350

Ile Pro Ser Leu Glu Arg Gln Glu Leu Pro Pro Lys Pro Asp Asp Ile
            355                 360                 365

Asp Thr Asn Glu Ala Ala Leu Lys Glu Trp Lys Lys Ala Ala Ala Gly
            370                 375                 380

Val Tyr Arg Leu Asp Lys Ala Arg Val Ser Arg Arg Ile Ser Leu Glu
385                 390                 395                 400

Phe Met Leu Glu Gln Ala Asn Lys Phe Ala Asn Lys Lys Ala Ile Trp
            405                 410                 415

Phe Pro Tyr Asn Met Asp Trp Arg Gly Arg Val Tyr Ala Val Pro Met
            420                 425                 430

Phe Asn Pro Gln Gly Asn Asp Met Thr Lys Gly Leu Leu Thr Leu Ala
            435                 440                 445

Lys Gly Lys Pro Ile Gly Glu Glu Gly Phe Tyr Trp Leu Lys Ile His
450                 455                 460

Gly Ala Asn Cys Ala Gly Val Asp Lys Val Pro Phe Pro Glu Arg Ile
465                 470                 475                 480

Ala Phe Ile Glu Lys His Val Asp Asp Ile Leu Ala Cys Ala Lys Asp
            485                 490                 495

Pro Ile Asn Asn Thr Trp Trp Ala Glu Gln Asp Ser Pro Phe Cys Phe
            500                 505                 510

Leu Ala Phe Cys Phe Glu Tyr Ala Gly Val Ala His His Gly Leu Ser
            515                 520                 525

Tyr Asn Cys Ser Leu Pro Leu Ala Phe Asp Gly Ser Cys Ser Gly Ile
            530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
            565                 570                 575

Gln Lys Val Asn Glu Ile Leu Lys Gln Asp Ala Ile Asn Gly Thr Pro
            580                 585                 590

Asn Glu Met Ile Thr Val Thr Asp Lys Asp Thr Gly Glu Ile Ser Glu
            595                 600                 605

Lys Leu Lys Leu Gly Thr Ser Thr Leu Ala Gln Gln Trp Leu Ala Tyr
            610                 615                 620

Gly Val Thr Arg Ser Val Thr Lys Arg Ser Val Met Thr Leu Ala Tyr
625                 630                 635                 640

Gly Ser Lys Glu Phe Gly Phe Arg Gln Gln Val Leu Asp Asp Thr Ile
            645                 650                 655

Gln Pro Ala Ile Asp Ser Gly Lys Gly Leu Met Phe Thr Gln Pro Asn
            660                 665                 670

Gln Ala Ala Gly Tyr Met Ala Lys Leu Ile Trp Asp Ala Val Ser Val
            675                 680                 685

Thr Val Val Ala Ala Val Glu Ala Met Asn Trp Leu Lys Ser Ala Ala
            690                 695                 700
```

Lys Leu Leu Ala Ala Glu Val Lys Asp Lys Thr Lys Glu Ile Leu
705                 710                 715                 720

Arg His Arg Cys Ala Val His Trp Thr Thr Pro Asp Gly Phe Pro Val
            725                 730                 735

Trp Gln Glu Tyr Arg Lys Pro Leu Gln Lys Arg Leu Asp Met Ile Phe
            740                 745                 750

Leu Gly Gln Phe Arg Leu Gln Pro Thr Ile Asn Thr Leu Lys Asp Ser
            755                 760                 765

Gly Ile Asp Ala His Lys Gln Glu Ser Gly Ile Ala Pro Asn Phe Val
770                 775                 780

His Ser Gln Asp Gly Ser His Leu Arg Met Thr Val Val Tyr Ala His
785                 790                 795                 800

Glu Lys Tyr Gly Ile Glu Ser Phe Ala Leu Ile His Asp Ser Phe Gly
                805                 810                 815

Thr Ile Pro Ala Asp Ala Gly Lys Leu Phe Lys Ala Val Arg Glu Thr
                820                 825                 830

Met Val Ile Thr Tyr Glu Asn Asn Asp Val Leu Ala Asp Phe Tyr Asp
                835                 840                 845

Gln Phe Ala Asp Gln Leu His Glu Thr Gln Leu Asp Lys Met Pro Pro
850                 855                 860

Leu Pro Lys Lys Gly Asn Leu Asn Leu Gln Asp Ile Leu Lys Ser Asp
865                 870                 875                 880

Phe Ala Phe Ala

<210> SEQ ID NO 61
<211> LENGTH: 884
<212> TYPE: PRT
<213> ORGANISM: Enterobacter bacteriophage E-4

<400> SEQUENCE: 61

Met Asn Ile Ile Glu Asn Ile Glu Lys Asn Asp Phe Ser Glu Ile Glu
1               5                   10                  15

Leu Ala Ala Ile Pro Phe Asn Thr Leu Ala Asp His Tyr Gly Ser Ala
                20                  25                  30

Leu Ala Arg Glu Gln Leu Ala Leu Glu His Glu Ser Tyr Glu Leu Gly
            35                  40                  45

Glu Arg Arg Phe Leu Lys Met Leu Glu Arg Gln Ala Lys Ala Gly Glu
        50                  55                  60

Ile Ala Asp Asn Ala Ala Lys Pro Leu Leu Ala Thr Leu Pro
65                  70                  75                  80

Lys Leu Thr Ala Arg Ile Val Glu Trp Leu Glu Glu Tyr Ala Ser Lys
                85                  90                  95

Lys Gly Arg Lys Pro Ser Ala Tyr Ala Pro Leu Gln Leu Leu Lys Pro
            100                 105                 110

Glu Ala Ser Ala Phe Ile Thr Leu Lys Val Ile Leu Ala Ser Leu Thr
        115                 120                 125

Ser Thr Asn Met Thr Thr Ile Gln Ala Ala Gly Met Leu Gly Lys
130                 135                 140

Ala Ile Glu Asp Glu Ala Arg Phe Gly Arg Ile Arg Asp Leu Glu Ala
145                 150                 155                 160

Lys His Phe Lys Lys His Val Glu Glu Gln Leu Asn Lys Arg His Gly
                165                 170                 175

Gln Val Tyr Lys Lys Ala Phe Met Gln Val Val Glu Ala Asp Met Ile
            180                 185                 190

```
Gly Arg Gly Leu Leu Gly Gly Glu Ala Trp Ser Ser Trp Asp Lys Glu
            195                 200                 205

Thr Thr Met His Val Gly Ile Arg Leu Ile Glu Met Leu Ile Glu Ser
            210                 215                 220

Thr Gly Leu Val Glu Leu Gln Arg His Asn Ala Gly Asn Ala Gly Ser
225                 230                 235                 240

Asp His Glu Ala Leu Gln Leu Ala Gln Glu Tyr Val Asp Val Leu Ala
            245                 250                 255

Lys Arg Ala Gly Ala Leu Ala Gly Ile Ser Pro Met Phe Gln Pro Cys
            260                 265                 270

Val Val Pro Pro Lys Pro Trp Val Ser Ile Thr Gly Gly Tyr Trp
            275                 280                 285

Ala Asn Gly Arg Arg Pro Leu Ala Leu Val Arg Thr His Ser Lys Lys
            290                 295                 300

Gly Leu Met Arg Tyr Glu Asp Val Tyr Met Pro Glu Val Tyr Lys Ala
305                 310                 315                 320

Val Asn Ile Ala Gln Asn Thr Ala Trp Lys Ile Asn Lys Lys Val Leu
            325                 330                 335

Ala Val Val Asn Glu Ile Val Asn Trp Lys Asn Cys Pro Val Ala Asp
            340                 345                 350

Ile Pro Ser Leu Glu Arg Gln Glu Leu Pro Pro Lys Pro Asp Asp Ile
            355                 360                 365

Asp Thr Asn Glu Ala Ala Leu Lys Glu Trp Lys Lys Ala Ala Ala Gly
            370                 375                 380

Ile Tyr Arg Leu Asp Lys Ala Arg Val Ser Arg Ile Ser Leu Glu
385                 390                 395                 400

Phe Met Leu Glu Gln Ala Asn Lys Phe Ala Asn Lys Lys Ala Ile Trp
            405                 410                 415

Phe Pro Tyr Asn Met Asp Trp Arg Gly Arg Val Tyr Ala Val Pro Met
            420                 425                 430

Phe Asn Pro Gln Gly Asn Asp Met Thr Lys Gly Leu Leu Thr Leu Ala
            435                 440                 445

Lys Gly Lys Pro Ile Gly Glu Glu Gly Phe Tyr Trp Leu Lys Ile His
            450                 455                 460

Gly Ala Asn Cys Ala Gly Val Asp Lys Val Pro Phe Pro Glu Arg Ile
465                 470                 475                 480

Ala Phe Ile Glu Lys His Val Asp Asp Ile Leu Ala Cys Ala Lys Asp
            485                 490                 495

Pro Ile Asn Asn Thr Trp Trp Ala Glu Gln Asp Ser Pro Phe Cys Phe
            500                 505                 510

Leu Ala Phe Cys Phe Glu Tyr Ala Gly Val Ala His His Gly Leu Ser
            515                 520                 525

Tyr Asn Cys Ser Leu Pro Leu Ala Phe Asp Gly Ser Cys Ser Gly Ile
            530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
            565                 570                 575

Gln Lys Val Asn Glu Ile Leu Lys Gln Asp Ala Ile Asn Gly Thr Pro
            580                 585                 590

Asn Glu Met Ile Thr Val Thr Asp Lys Asp Thr Gly Glu Ile Ser Glu
            595                 600                 605
```

Lys Leu Lys Leu Gly Thr Ser Thr Leu Ala Gln Gln Trp Leu Ala Tyr
610                 615                 620

Gly Val Thr Arg Ser Val Thr Lys Arg Ser Val Met Thr Leu Ala Tyr
625                 630                 635                 640

Gly Ser Lys Glu Phe Gly Phe Arg Gln Gln Val Leu Asp Asp Thr Ile
            645                 650                 655

Gln Pro Ala Ile Asp Ser Gly Lys Gly Leu Met Phe Thr Gln Pro Asn
        660                 665                 670

Gln Ala Ala Gly Tyr Met Ala Lys Leu Ile Trp Asp Ala Val Ser Val
            675                 680                 685

Thr Val Val Ala Ala Val Glu Ala Met Asn Trp Leu Lys Ser Ala Ala
690                 695                 700

Lys Leu Leu Ala Ala Glu Val Lys Asp Lys Thr Lys Glu Ile Leu
705                 710                 715                 720

Arg His Arg Cys Ala Val His Trp Thr Thr Pro Asp Gly Phe Pro Val
                725                 730                 735

Trp Gln Glu Tyr Arg Lys Pro Leu Gln Lys Arg Leu Asp Met Ile Phe
        740                 745                 750

Leu Gly Gln Phe Arg Leu Gln Pro Thr Ile Asn Thr Leu Lys Asp Ser
            755                 760                 765

Gly Ile Asp Ala His Lys Gln Glu Ser Gly Ile Ala Pro Asn Phe Val
770                 775                 780

His Ser Gln Asp Gly Ser His Leu Arg Met Thr Val Val Tyr Ala His
785                 790                 795                 800

Glu Lys Tyr Gly Ile Glu Ser Phe Ala Leu Ile His Asp Ser Phe Gly
                805                 810                 815

Thr Ile Pro Ala Asp Ala Gly Lys Leu Phe Lys Ala Val Arg Glu Thr
        820                 825                 830

Met Val Leu Thr Tyr Glu Asn Asn Asp Val Leu Ala Asp Phe Tyr Asp
            835                 840                 845

Gln Phe Ala Asp Gln Leu His Glu Thr Gln Leu Asp Lys Met Pro Pro
850                 855                 860

Leu Pro Lys Lys Gly Asn Leu Asn Leu Gln Asp Ile Leu Lys Ser Asp
865                 870                 875                 880

Phe Ala Phe Ala

<210> SEQ ID NO 62
<211> LENGTH: 884
<212> TYPE: PRT
<213> ORGANISM: Yersinia bacteriophage phiYe-F10

<400> SEQUENCE: 62

Met Asn Ile Ile Glu Asn Ile Glu Lys Asn Asp Phe Ser Glu Ile Glu
1               5                   10                  15

Leu Ala Ala Ile Pro Phe Asn Thr Leu Ala Asp His Tyr Gly Ser Ala
            20                  25                  30

Leu Ala Arg Glu Gln Leu Ala Leu His Glu Ser Tyr Glu Leu Gly
        35                  40                  45

Glu Arg Arg Phe Leu Lys Met Leu Glu Arg Gln Ala Lys Ala Gly Glu
    50                  55                  60

Ile Ala Asp Asn Ala Ala Ala Lys Pro Leu Leu Ala Thr Leu Leu Pro
65                  70                  75                  80

Lys Leu Thr Ala Arg Ile Val Glu Trp Leu Glu Glu Tyr Ala Ser Lys
                85                  90                  95

```
Lys Gly Arg Lys Pro Val Ala Tyr Ala Pro Leu Gln Ser Leu Lys Pro
                100                 105                 110

Glu Ala Ser Ala Phe Ile Thr Leu Lys Val Ile Leu Ala Ser Leu Thr
            115                 120                 125

Ser Thr Asn Met Thr Thr Ile Gln Ala Ala Gly Met Leu Gly Lys
130                 135                 140

Ala Ile Glu Asp Glu Ala Arg Phe Gly Arg Ile Arg Asp Leu Glu Ala
145                 150                 155                 160

Lys His Phe Lys Lys His Val Glu Glu Gln Leu Asn Lys Arg His Gly
                165                 170                 175

Gln Val Tyr Lys Lys Ala Phe Met Gln Val Val Glu Ala Asp Met Ile
            180                 185                 190

Gly Arg Gly Leu Leu Gly Gly Glu Ala Trp Ser Ser Trp Asp Lys Glu
        195                 200                 205

Thr Thr Met His Val Gly Ile Arg Leu Ile Glu Met Leu Ile Glu Ser
210                 215                 220

Thr Gly Leu Val Glu Leu Gln Arg His Asn Ala Gly Asn Ala Gly Ser
225                 230                 235                 240

Asp His Glu Ala Leu Gln Leu Ala Gln Glu Tyr Val Asp Val Leu Ala
                245                 250                 255

Lys Arg Ala Gly Ala Leu Ala Gly Ile Ser Pro Met Phe Gln Pro Cys
            260                 265                 270

Val Val Pro Pro Lys Pro Trp Val Ser Ile Thr Gly Gly Tyr Trp
        275                 280                 285

Ala Asn Gly Arg Arg Pro Leu Ala Leu Ile Arg Thr His Ser Lys Lys
290                 295                 300

Gly Leu Met Arg Tyr Glu Asp Val Tyr Met Pro Glu Val Tyr Lys Ala
305                 310                 315                 320

Val Asn Ile Ala Gln Asn Thr Ala Trp Lys Ile Asn Lys Lys Val Leu
                325                 330                 335

Ala Val Val Asn Glu Ile Val Asn Trp Lys Asn Cys Pro Val Ala Asp
            340                 345                 350

Ile Pro Ser Leu Glu Arg Gln Glu Leu Pro Pro Lys Pro Asp Asp Ile
        355                 360                 365

Asp Thr Asn Glu Ala Ala Leu Lys Glu Trp Lys Lys Ala Ala Ala Gly
370                 375                 380

Val Tyr Arg Leu Asp Lys Ala Arg Val Ser Arg Ile Ser Leu Glu
385                 390                 395                 400

Phe Met Leu Glu Gln Ala Asn Lys Phe Ala Ser Lys Lys Ala Ile Trp
                405                 410                 415

Phe Pro Tyr Asn Met Asp Trp Arg Gly Arg Val Tyr Ala Val Pro Met
            420                 425                 430

Phe Asn Pro Gln Gly Asn Asp Met Thr Lys Gly Leu Leu Thr Leu Ala
        435                 440                 445

Lys Gly Lys Pro Ile Gly Glu Glu Gly Phe Tyr Trp Leu Lys Ile His
450                 455                 460

Gly Ala Asn Cys Ala Gly Val Asp Lys Val Pro Phe Pro Glu Arg Ile
465                 470                 475                 480

Ala Phe Ile Glu Lys His Val Asp Asp Ile Leu Ala Cys Ala Lys Asp
                485                 490                 495

Pro Ile Asn Asn Thr Trp Trp Ala Glu Gln Asp Ser Pro Phe Cys Phe
            500                 505                 510

Leu Ala Phe Cys Phe Glu Tyr Ala Gly Val Ala His His Gly Leu Ser
```

```
              515                 520                 525
Tyr Asn Cys Ser Leu Pro Leu Ala Phe Asp Gly Ser Cys Ser Gly Ile
530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
                565                 570                 575

Gln Lys Val Asn Glu Ile Leu Lys Gln Asp Ala Ile Asn Gly Thr Pro
                580                 585                 590

Asn Glu Met Ile Thr Val Thr Asp Lys Asp Thr Gly Glu Ile Ser Glu
                595                 600                 605

Lys Leu Lys Leu Gly Thr Ser Thr Leu Ala Gln Gln Trp Leu Ala Tyr
610                 615                 620

Gly Val Thr Arg Ser Val Thr Lys Arg Ser Val Met Thr Leu Ala Tyr
625                 630                 635                 640

Gly Ser Lys Glu Phe Gly Phe Arg Gln Gln Val Leu Asp Asp Thr Ile
                645                 650                 655

Gln Pro Ala Ile Asp Ser Gly Lys Gly Leu Met Phe Thr Gln Pro Asn
                660                 665                 670

Gln Ala Ala Gly Tyr Met Ala Lys Leu Ile Trp Asp Ala Val Ser Val
                675                 680                 685

Thr Val Val Ala Ala Val Glu Ala Met Asn Trp Leu Lys Ser Ala Ala
                690                 695                 700

Lys Leu Leu Ala Ala Glu Val Lys Asp Lys Lys Thr Lys Glu Ile Leu
705                 710                 715                 720

Arg His Arg Cys Ala Val His Trp Thr Thr Pro Asp Gly Phe Pro Val
                725                 730                 735

Trp Gln Glu Tyr Arg Lys Pro Leu Gln Lys Arg Leu Asp Met Ile Phe
                740                 745                 750

Leu Gly Gln Phe Arg Leu Gln Pro Thr Ile Asn Thr Leu Lys Asp Ser
                755                 760                 765

Gly Ile Asp Ala His Lys Gln Glu Ser Gly Ile Ala Pro Asn Phe Val
770                 775                 780

His Ser Gln Asp Gly Ser His Leu Arg Met Thr Val Val Tyr Ala His
785                 790                 795                 800

Glu Lys Tyr Gly Ile Glu Ser Phe Ala Leu Ile His Asp Ser Phe Gly
                805                 810                 815

Thr Ile Pro Ala Asp Ala Gly Lys Leu Phe Lys Ala Val Arg Glu Thr
                820                 825                 830

Met Val Ile Thr Tyr Glu Asn Asn Asp Val Leu Ala Asp Phe Tyr Asp
                835                 840                 845

Gln Phe Ala Asp Gln Leu His Glu Thr Gln Leu Asp Lys Met Pro Pro
                850                 855                 860

Leu Pro Lys Lys Gly Asn Leu Asn Leu Gln Asp Ile Leu Lys Ser Asp
865                 870                 875                 880

Phe Ala Phe Ala

<210> SEQ ID NO 63
<211> LENGTH: 884
<212> TYPE: PRT
<213> ORGANISM: Citrobacter bacteriophage phiCFP-1

<400> SEQUENCE: 63

Met Asn Ile Ile Glu Asn Ile Glu Lys Asn Asp Phe Ser Glu Ile Glu
```

-continued

```
1               5                   10                  15
Leu Ala Ala Ile Pro Phe Asn Thr Leu Ala Asp His Tyr Gly Ser Ala
            20                  25                  30
Leu Ala Arg Glu Gln Leu Ala Leu Glu His Glu Ser Tyr Glu Leu Gly
            35                  40                  45
Glu Arg Arg Phe Leu Lys Met Leu Glu Arg Gln Ala Lys Ala Gly Glu
            50                  55                  60
Ile Ala Asp Asn Ala Ala Ala Lys Pro Leu Leu Ala Thr Leu Leu Pro
65                  70                  75                  80
Lys Leu Thr Ala Arg Ile Val Glu Trp Leu Glu Glu Tyr Asp Ser Lys
            85                  90                  95
Lys Gly Arg Lys Pro Val Ala Tyr Ala Pro Leu Gln Leu Leu Lys Pro
            100                 105                 110
Glu Ala Ser Ala Phe Ile Thr Leu Lys Val Ile Leu Ala Ser Leu Thr
            115                 120                 125
Ser Thr Asn Met Thr Thr Ile Gln Ala Ala Gly Met Leu Gly Lys
            130                 135                 140
Ala Ile Glu Asp Glu Ala Arg Phe Gly Arg Ile Arg Asp Leu Glu Ala
145                 150                 155                 160
Lys His Phe Lys Lys His Val Glu Glu Gln Leu Asn Lys Arg His Gly
            165                 170                 175
Gln Val Tyr Lys Lys Ala Phe Met Gln Val Val Glu Ala Asp Met Ile
            180                 185                 190
Gly Arg Gly Leu Leu Gly Gly Glu Ala Trp Ser Ser Trp Asp Lys Glu
            195                 200                 205
Thr Thr Met His Val Gly Ile Arg Leu Ile Glu Met Leu Ile Glu Ser
            210                 215                 220
Thr Gly Leu Val Glu Leu Gln Arg His Asn Ala Gly Asn Ala Gly Ser
225                 230                 235                 240
Asp His Glu Ala Leu Gln Leu Ala Gln Glu Tyr Val Asp Val Leu Ala
            245                 250                 255
Lys Arg Ala Gly Ala Leu Ala Gly Ile Ser Pro Met Phe Gln Pro Cys
            260                 265                 270
Val Val Pro Pro Lys Pro Trp Val Ala Ile Thr Gly Gly Tyr Trp
            275                 280                 285
Ala Asn Gly Arg Arg Pro Leu Ala Leu Val Arg Thr His Ser Lys Lys
            290                 295                 300
Gly Leu Met Arg Tyr Glu Asp Val Tyr Met Pro Glu Val Tyr Lys Ala
305                 310                 315                 320
Val Asn Ile Ala Gln Asn Thr Ala Trp Lys Ile Asn Lys Lys Val Leu
            325                 330                 335
Ala Val Val Asn Glu Ile Val Asn Trp Lys Asn Cys Pro Val Ala Asp
            340                 345                 350
Ile Pro Ser Leu Glu Arg Gln Glu Leu Pro Pro Lys Pro Asp Asp Ile
            355                 360                 365
Asp Thr Asn Glu Ala Ala Leu Lys Glu Trp Lys Lys Ala Ala Gly
            370                 375                 380
Ile Tyr Arg Leu Asp Lys Ala Arg Val Ser Arg Ile Ser Leu Glu
385                 390                 395                 400
Phe Met Leu Glu Gln Ala Asn Lys Phe Ala Ser Lys Lys Ala Ile Trp
            405                 410                 415
Phe Pro Tyr Asn Met Asp Trp Arg Gly Arg Val Tyr Ala Val Pro Met
            420                 425                 430
```

```
Phe Asn Pro Gln Gly Asn Asp Met Thr Lys Gly Leu Leu Thr Leu Ala
        435                 440                 445

Lys Gly Lys Pro Ile Gly Glu Gly Phe Tyr Trp Leu Lys Ile His
450                 455                 460

Gly Ala Asn Cys Ala Gly Val Asp Lys Val Pro Phe Pro Glu Arg Ile
465                 470                 475                 480

Ala Phe Ile Glu Lys His Val Asp Asp Ile Leu Ala Cys Ala Lys Asp
                485                 490                 495

Pro Ile Asn Asn Thr Trp Trp Ala Glu Gln Asp Ser Pro Phe Cys Phe
                500                 505                 510

Leu Ala Phe Cys Phe Glu Tyr Ala Gly Val Ala His His Gly Leu Ser
                515                 520                 525

Tyr Asn Cys Ser Leu Pro Leu Ala Phe Asp Gly Ser Cys Ser Gly Ile
530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
                565                 570                 575

Gln Lys Val Asn Glu Ile Leu Lys Gln Asp Ala Ile Asn Gly Thr Pro
                580                 585                 590

Asn Glu Met Ile Thr Val Thr Asp Lys Asp Thr Gly Glu Ile Ser Glu
                595                 600                 605

Lys Leu Lys Leu Gly Thr Ser Thr Leu Ala Gln Gln Trp Leu Ala Tyr
610                 615                 620

Gly Val Thr Arg Ser Val Thr Lys Arg Ser Val Met Thr Leu Ala Tyr
625                 630                 635                 640

Gly Ser Lys Glu Phe Gly Phe Arg Gln Gln Val Leu Asp Asp Thr Ile
                645                 650                 655

Gln Pro Ala Ile Asp Ser Gly Lys Gly Leu Met Phe Thr Gln Pro Asn
                660                 665                 670

Gln Ala Ala Gly Tyr Met Ala Lys Leu Ile Trp Asp Ala Val Ser Val
                675                 680                 685

Thr Val Val Ala Ala Val Glu Ala Met Asn Trp Leu Lys Ser Ala Ala
                690                 695                 700

Lys Leu Leu Ala Ala Glu Val Lys Asp Lys Thr Lys Glu Ile Leu
705                 710                 715                 720

Arg His Arg Cys Ala Val His Trp Thr Thr Pro Asp Gly Phe Pro Val
                725                 730                 735

Trp Gln Glu Tyr Arg Lys Pro Leu Gln Lys Arg Leu Asp Met Ile Phe
                740                 745                 750

Leu Gly Gln Phe Arg Leu Gln Pro Thr Ile Asn Thr Leu Lys Asp Ser
                755                 760                 765

Gly Ile Asp Ala His Lys Gln Glu Ser Gly Ile Ala Pro Asn Phe Val
770                 775                 780

His Ser Gln Asp Gly Ser His Leu Arg Met Thr Val Val Tyr Ala His
785                 790                 795                 800

Glu Lys Tyr Gly Ile Glu Ser Phe Ala Leu Ile His Asp Ser Phe Gly
                805                 810                 815

Thr Ile Pro Ala Asp Ala Gly Lys Leu Phe Lys Ala Val Arg Glu Thr
                820                 825                 830

Met Val Ile Thr Tyr Glu Asn Asn Asp Val Leu Ala Asp Phe Tyr Asp
                835                 840                 845
```

```
                Gln Phe Ala Asp Gln Leu His Glu Thr Gln Leu Asp Lys Met Pro Pro
                850                 855                 860
                Leu Pro Lys Lys Gly Asn Leu Asn Leu Gln Asp Ile Leu Lys Ser Asp
                865                 870                 875                 880
                Phe Ala Phe Ala

<210> SEQ ID NO 64
<211> LENGTH: 884
<212> TYPE: PRT
<213> ORGANISM: Citrobacter bacteriophage SH1

<400> SEQUENCE: 64

Met Asn Ile Ile Glu Asn Ile Glu Lys Asn Asp Phe Ser Glu Ile Glu
1               5                   10                  15

Leu Ala Ala Ile Pro Phe Asn Thr Leu Ala Asp His Tyr Gly Ser Ala
                20                  25                  30

Leu Ala Arg Glu Gln Leu Ala Leu Glu His Glu Ser Tyr Glu Leu Gly
            35                  40                  45

Glu Arg Arg Phe Leu Lys Met Leu Glu Arg Gln Ala Lys Ala Gly Glu
50                  55                  60

Ile Ala Asp Asn Ala Ala Ala Lys Pro Leu Leu Ala Thr Leu Leu Pro
65                  70                  75                  80

Lys Leu Thr Ala Arg Ile Val Glu Trp Leu Glu Glu Tyr Ala Ser Lys
                85                  90                  95

Lys Gly Arg Lys Pro Val Ala Tyr Ala Pro Leu Gln Leu Leu Lys Pro
            100                 105                 110

Glu Ala Ser Ala Phe Ile Thr Leu Lys Val Ile Leu Ala Ser Leu Thr
        115                 120                 125

Ser Thr Asn Met Thr Thr Ile Gln Ala Ala Ala Gly Met Leu Gly Lys
130                 135                 140

Ala Ile Glu Asp Glu Ala Arg Phe Gly Arg Ile Arg Asp Leu Glu Ala
145                 150                 155                 160

Lys His Phe Lys Lys His Val Glu Glu Gln Leu Asn Lys Arg His Gly
                165                 170                 175

Gln Val Tyr Lys Lys Ala Phe Met Gln Val Glu Ala Asp Met Ile
            180                 185                 190

Gly Arg Gly Leu Leu Gly Gly Glu Ala Trp Ser Ser Trp Asp Lys Glu
        195                 200                 205

Thr Thr Met His Val Gly Ile Arg Leu Ile Glu Met Leu Ile Glu Ser
210                 215                 220

Thr Gly Leu Val Glu Leu Gln Arg His Asn Ala Gly Asn Ala Gly Ser
225                 230                 235                 240

Asp His Glu Ala Leu Gln Leu Ala Gln Glu Tyr Val Asp Val Leu Ala
                245                 250                 255

Lys Arg Ala Gly Ala Leu Ala Gly Ile Ser Pro Met Phe Gln Pro Cys
            260                 265                 270

Val Val Pro Pro Lys Pro Trp Val Ser Ile Thr Gly Gly Gly Tyr Trp
        275                 280                 285

Ala Asn Gly Arg Arg Pro Leu Ala Leu Val Arg Thr His Ser Lys Lys
290                 295                 300

Gly Leu Met Arg Tyr Glu Asp Val Tyr Met Pro Glu Val Tyr Lys Ala
305                 310                 315                 320

Val Asn Ile Ala Gln Asn Thr Ala Trp Lys Ile Asn Lys Lys Val Leu
                325                 330                 335
```

-continued

```
Ala Val Val Asn Glu Ile Val Asn Trp Lys Asn Cys Pro Val Ala Asp
            340                 345                 350

Ile Pro Ser Leu Glu Arg Gln Glu Leu Pro Pro Lys Pro Asp Asp Ile
        355                 360                 365

Asp Thr Asn Glu Ala Ala Leu Lys Glu Trp Lys Lys Ala Ala Ala Gly
    370                 375                 380

Ile Tyr Arg Leu Asp Lys Ala Arg Val Ser Arg Ile Ser Leu Glu
385                 390                 395                 400

Phe Met Leu Glu Gln Ala Asn Lys Phe Ala Ser Lys Lys Ala Ile Trp
                405                 410                 415

Phe Pro Tyr Asn Met Asp Trp Arg Gly Arg Val Tyr Ala Val Pro Met
            420                 425                 430

Phe Asn Pro Gln Gly Asn Asp Met Thr Lys Gly Leu Leu Thr Leu Ala
        435                 440                 445

Lys Gly Lys Pro Ile Gly Glu Gly Phe Tyr Trp Leu Lys Ile His
    450                 455                 460

Gly Ala Asn Cys Ala Gly Val Asp Lys Val Pro Phe Pro Glu Arg Ile
465                 470                 475                 480

Ala Phe Ile Glu Lys His Val Asp Asp Ile Leu Ala Cys Ala Lys Asp
                485                 490                 495

Pro Ile Asn Asn Thr Trp Trp Ala Glu Gln Asp Ser Pro Phe Cys Phe
            500                 505                 510

Leu Ala Phe Cys Phe Glu Tyr Ala Gly Val Ala His His Gly Leu Ser
        515                 520                 525

Tyr Asn Cys Ser Leu Pro Leu Ala Phe Asp Gly Ser Cys Ser Gly Ile
    530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
                565                 570                 575

Gln Lys Val Asn Glu Ile Leu Lys Gln Asp Ala Ile Asn Gly Thr Pro
            580                 585                 590

Asn Glu Met Ile Thr Val Thr Asp Lys Asp Thr Gly Glu Ile Ser Glu
        595                 600                 605

Lys Leu Lys Leu Gly Thr Ser Thr Leu Ala Gln Gln Trp Leu Ala Tyr
    610                 615                 620

Gly Val Thr Arg Ser Val Thr Lys Arg Ser Val Met Thr Leu Ala Tyr
625                 630                 635                 640

Gly Ser Lys Glu Phe Gly Phe Arg Gln Gln Val Leu Asp Asp Thr Ile
                645                 650                 655

Gln Pro Ala Ile Asp Ser Gly Lys Gly Leu Met Phe Thr Gln Pro Asn
            660                 665                 670

Gln Ala Ala Gly Tyr Met Ala Lys Leu Ile Trp Asp Ala Val Ser Val
        675                 680                 685

Thr Val Val Ala Ala Val Glu Ala Met Asn Trp Leu Lys Ser Ala Ala
    690                 695                 700

Lys Leu Leu Ala Asp Glu Val Lys Asp Lys Thr Lys Glu Ile Leu
705                 710                 715                 720

Arg His Arg Cys Ala Val His Trp Thr Thr Pro Asp Gly Phe Pro Val
                725                 730                 735

Trp Gln Glu Tyr Arg Lys Pro Leu Gln Lys Arg Leu Asp Met Ile Phe
            740                 745                 750

Leu Gly Gln Phe Arg Leu Gln Pro Thr Ile Asn Thr Leu Lys Asp Ser
```

```
                755                 760                 765
Gly Ile Asp Ala His Lys Gln Glu Ser Gly Ile Ala Pro Asn Phe Val
770                 775                 780

His Ser Gln Asp Gly Ser His Leu Arg Met Thr Val Val Tyr Ala His
785                 790                 795                 800

Glu Lys Tyr Gly Ile Glu Ser Phe Ala Leu Ile His Asp Ser Phe Gly
                805                 810                 815

Thr Ile Pro Ala Asp Ala Gly Lys Leu Phe Lys Ala Val Arg Glu Thr
            820                 825                 830

Met Val Ile Thr Tyr Glu Asn Asn Asp Val Leu Ala Asp Phe Tyr Asp
            835                 840                 845

Gln Phe Ala Asp Gln Leu His Glu Thr Gln Leu Asp Lys Met Pro Pro
850                 855                 860

Leu Pro Lys Lys Gly Asn Leu Asn Leu Gln Asp Ile Leu Lys Ser Asp
865                 870                 875                 880

Phe Ala Phe Ala

<210> SEQ ID NO 65
<211> LENGTH: 884
<212> TYPE: PRT
<213> ORGANISM: Salmonella bacteriophage phiSG-JL2

<400> SEQUENCE: 65

Met Asn Ile Ile Glu Asn Ile Glu Lys Asn Asp Phe Ser Glu Ile Glu
1               5                   10                  15

Leu Ala Ala Ile Pro Phe Asn Thr Leu Ala Asp His Tyr Gly Ser Ala
                20                  25                  30

Leu Ala Arg Glu Gln Leu Ala Leu Glu His Glu Ser Tyr Glu Leu Gly
            35                  40                  45

Glu Arg Arg Phe Leu Lys Met Leu Glu Arg Gln Ala Lys Ala Gly Glu
        50                  55                  60

Ile Ala Asp Asn Ala Ala Ala Lys Pro Leu Leu Ala Thr Leu Leu Pro
65                  70                  75                  80

Lys Leu Thr Ala Arg Ile Val Glu Trp Leu Glu Glu Tyr Ala Ser Lys
                85                  90                  95

Lys Gly Arg Lys Pro Val Ala Tyr Ala Pro Leu Gln Leu Leu Lys Pro
            100                 105                 110

Glu Ala Ser Ala Phe Ile Thr Leu Lys Val Ile Leu Ala Ser Leu Thr
        115                 120                 125

Ser Thr Asn Met Thr Thr Ile Gln Ala Ala Ala Gly Met Leu Gly Lys
130                 135                 140

Ala Ile Glu Asp Glu Ala Arg Phe Gly Arg Ile Arg Asp Leu Glu Ala
145                 150                 155                 160

Lys His Phe Lys Lys His Val Glu Glu Gln Leu Asn Lys Arg His Gly
                165                 170                 175

Gln Val Tyr Lys Lys Ala Phe Met Gln Val Glu Ala Asp Met Ile
            180                 185                 190

Gly Arg Gly Leu Leu Gly Gly Glu Ala Trp Ser Ser Trp Asp Lys Glu
        195                 200                 205

Thr Thr Met His Val Gly Ile Arg Leu Ile Glu Met Leu Ile Glu Ser
210                 215                 220

Thr Gly Leu Val Glu Leu Gln Arg His Asn Ala Gly Asn Ala Gly Ser
225                 230                 235                 240

Asp His Glu Ala Leu Gln Leu Ala Gln Glu Tyr Val Asp Val Leu Ala
```

```
            245                 250                 255
Lys Arg Ala Gly Ala Leu Ala Gly Ile Ser Pro Met Phe Gln Pro Cys
            260                 265                 270

Val Val Pro Pro Lys Pro Trp Val Ala Ile Thr Gly Gly Tyr Trp
            275                 280             285

Ala Asn Gly Arg Arg Pro Leu Ala Leu Val Arg Thr His Ser Lys Lys
            290                 295                 300

Gly Leu Met Arg Tyr Glu Asp Val Tyr Met Pro Glu Val Tyr Lys Ala
305                 310                 315                 320

Val Asn Ile Ala Gln Asn Thr Ala Trp Lys Ile Asn Lys Lys Val Leu
                325                 330                 335

Ala Val Val Asn Glu Ile Val Asn Trp Lys Asn Cys Pro Val Ala Asp
                340                 345                 350

Ile Pro Ser Leu Glu Arg Gln Glu Leu Pro Pro Lys Pro Asp Asp Ile
                355                 360                 365

Asp Thr Asn Glu Ala Ala Leu Lys Glu Trp Lys Lys Ala Ala Ala Gly
        370                 375                 380

Val Tyr Arg Leu Asp Lys Ala Arg Val Ser Arg Arg Ile Ser Leu Glu
385                 390                 395                 400

Phe Met Leu Glu Gln Ala Asn Lys Phe Ala Ser Lys Lys Ala Ile Trp
                405                 410                 415

Phe Pro Tyr Asn Met Asp Trp Arg Gly Arg Val Tyr Ala Val Pro Met
                420                 425                 430

Phe Asn Pro Gln Gly Asn Asp Met Thr Lys Gly Leu Leu Thr Leu Ala
                435                 440                 445

Lys Gly Lys Pro Ile Gly Glu Glu Gly Phe Tyr Trp Leu Lys Ile His
            450                 455                 460

Gly Ala Asn Cys Ala Gly Val Asp Lys Val Pro Phe Pro Glu Arg Ile
465                 470                 475                 480

Ala Phe Ile Glu Lys His Val Asp Asp Ile Leu Ala Cys Ala Lys Asp
                485                 490                 495

Pro Ile Asn Asn Thr Trp Trp Ala Glu Gln Asp Ser Pro Phe Cys Phe
                500                 505                 510

Leu Ala Phe Cys Phe Glu Tyr Ala Gly Val Ala His His Gly Leu Ser
            515                 520                 525

Tyr Asn Cys Ser Leu Pro Leu Ala Phe Asp Gly Ser Cys Ser Gly Ile
            530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
                565                 570                 575

Gln Lys Val Asn Glu Ile Leu Lys Gln Asp Ala Ile Asn Gly Thr Pro
            580                 585                 590

Asn Glu Met Ile Thr Val Thr Asp Lys Asp Thr Gly Glu Ile Ser Glu
            595                 600                 605

Lys Leu Lys Leu Gly Thr Ser Thr Leu Ala Gln Gln Trp Leu Ala Tyr
            610                 615                 620

Gly Val Thr Arg Ser Val Thr Lys Arg Ser Val Met Thr Leu Ala Tyr
625                 630                 635                 640

Gly Ser Lys Glu Phe Gly Phe Arg Gln Gln Val Leu Asp Asp Thr Ile
                645                 650                 655

Gln Pro Ala Ile Asp Ser Gly Lys Gly Leu Met Phe Thr Gln Pro Asn
            660                 665                 670
```

```
Gln Ala Ala Gly Tyr Met Ala Lys Leu Ile Trp Asp Ala Val Ser Val
            675                 680                 685

Thr Val Val Ala Ala Val Glu Ala Met Asn Trp Leu Lys Ser Ala Ala
690                 695                 700

Lys Leu Leu Ala Ala Glu Val Lys Asp Lys Thr Lys Glu Ile Leu
705                 710                 715                 720

Arg His Arg Cys Ala Val His Trp Thr Thr Pro Asp Gly Phe Pro Val
                725                 730                 735

Trp Gln Glu Tyr Arg Lys Pro Leu Gln Lys Arg Leu Asp Met Ile Phe
            740                 745                 750

Leu Gly Gln Phe Arg Leu Gln Pro Thr Ile Asn Thr Leu Lys Asp Ser
            755                 760                 765

Gly Ile Asp Ala His Lys Gln Glu Ser Gly Ile Ala Pro Asn Phe Val
770                 775                 780

His Ser Gln Asp Gly Ser His Leu Arg Met Thr Val Val Tyr Ala His
785                 790                 795                 800

Glu Lys Tyr Gly Ile Glu Ser Phe Ala Leu Ile His Asp Ser Phe Gly
                805                 810                 815

Thr Ile Pro Ala Asp Ala Gly Lys Leu Phe Lys Ala Val Arg Glu Thr
            820                 825                 830

Met Val Leu Thr Tyr Glu Asn Asn Asp Val Leu Ala Asp Phe Tyr Asp
            835                 840                 845

Gln Phe Ala Asp Gln Leu His Glu Thr Gln Leu Asp Lys Met Pro Pro
850                 855                 860

Leu Pro Lys Lys Gly Lys Leu Asn Leu Gln Asp Ile Leu Lys Ser Asp
865                 870                 875                 880

Phe Ala Phe Ala

<210> SEQ ID NO 66
<211> LENGTH: 884
<212> TYPE: PRT
<213> ORGANISM: Yersinia bacteriophage phiYeO3-12

<400> SEQUENCE: 66

Met Asn Ile Ile Glu Asn Ile Glu Lys Asn Asp Phe Ser Glu Ile Glu
1               5                   10                  15

Leu Ala Ala Ile Pro Phe Asn Thr Leu Ala Asp His Tyr Gly Ser Ala
                20                  25                  30

Leu Ala Arg Glu Gln Leu Ala Leu Glu His Glu Ser Tyr Glu Leu Gly
            35                  40                  45

Glu Arg Arg Phe Leu Lys Met Leu Glu Arg Gln Ala Lys Ala Gly Glu
50                  55                  60

Ile Ala Asp Asn Ala Ala Ala Lys Pro Leu Leu Ala Thr Leu Leu Pro
65                  70                  75                  80

Lys Leu Thr Thr Arg Ile Val Glu Trp Leu Glu Glu Tyr Ala Thr Lys
                85                  90                  95

Lys Gly Arg Lys Pro Val Ala Tyr Ala Pro Leu Gln Ser Leu Lys Pro
                100                 105                 110

Glu Ala Ser Ala Phe Ile Thr Leu Lys Val Ile Leu Ala Ser Leu Thr
            115                 120                 125

Ser Thr Asn Met Thr Thr Ile Gln Ala Ala Gly Met Leu Gly Lys
130                 135                 140

Ala Ile Glu Asp Glu Ala Arg Phe Gly Arg Ile Arg Asp Leu Glu Ala
145                 150                 155                 160
```

```
Lys His Phe Lys Lys His Val Glu Glu Gln Leu Asn Lys Arg His Gly
                165                 170                 175

Gln Val Tyr Lys Lys Ala Phe Met Gln Val Val Glu Ala Asp Met Ile
            180                 185                 190

Gly Arg Gly Leu Leu Gly Gly Glu Ala Trp Ser Ser Trp Asp Lys Glu
            195                 200                 205

Thr Thr Met His Val Gly Ile Arg Leu Ile Glu Met Leu Ile Glu Ser
    210                 215                 220

Thr Gly Leu Val Glu Leu Gln Arg His Asn Ala Gly Asn Ala Gly Ser
225                 230                 235                 240

Asp His Glu Ala Leu Gln Leu Ala Gln Glu Tyr Val Asp Val Leu Ala
                245                 250                 255

Lys Arg Ala Gly Ala Leu Ala Gly Ile Ser Pro Met Phe Gln Pro Cys
                260                 265                 270

Val Val Pro Pro Lys Pro Trp Val Ala Ile Thr Gly Gly Tyr Trp
            275                 280                 285

Ala Asn Gly Arg Arg Pro Leu Ala Leu Val Arg Thr His Ser Lys Lys
            290                 295                 300

Gly Leu Met Arg Tyr Glu Asp Val Tyr Met Pro Glu Val Tyr Lys Ala
305                 310                 315                 320

Val Asn Ile Ala Gln Asn Thr Ala Trp Lys Ile Asn Lys Lys Val Leu
                325                 330                 335

Ala Val Val Asn Glu Ile Val Asn Trp Lys Asn Cys Pro Val Ala Asp
                340                 345                 350

Ile Pro Ser Leu Glu Arg Gln Glu Leu Pro Pro Lys Pro Asp Asp Ile
            355                 360                 365

Asp Thr Asn Glu Ala Ala Leu Lys Glu Trp Lys Lys Ala Ala Ala Gly
            370                 375                 380

Ile Tyr Arg Leu Asp Lys Ala Arg Val Ser Arg Ile Ser Leu Glu
385                 390                 395                 400

Phe Met Leu Glu Gln Ala Asn Lys Phe Ala Ser Lys Lys Ala Ile Trp
                405                 410                 415

Phe Pro Tyr Asn Met Asp Trp Arg Gly Arg Val Tyr Ala Val Pro Met
            420                 425                 430

Phe Asn Pro Gln Gly Asn Asp Met Thr Lys Gly Leu Leu Thr Leu Ala
            435                 440                 445

Lys Gly Lys Pro Ile Gly Glu Glu Gly Phe Tyr Trp Leu Lys Ile His
            450                 455                 460

Gly Ala Asn Cys Ala Gly Val Asp Lys Val Pro Phe Pro Glu Arg Ile
465                 470                 475                 480

Ala Phe Ile Glu Lys His Val Asp Asp Ile Leu Ala Cys Ala Lys Asp
                485                 490                 495

Pro Ile Asn Asn Thr Trp Trp Ala Glu Gln Asp Ser Pro Phe Cys Phe
            500                 505                 510

Leu Ala Phe Cys Phe Glu Tyr Ala Gly Val Ala His His Gly Leu Ser
            515                 520                 525

Tyr Asn Cys Ser Leu Pro Leu Ala Phe Asp Gly Ser Cys Ser Gly Ile
            530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
                565                 570                 575
```

-continued

```
Gln Lys Val Asn Glu Ile Leu Lys Gln Asp Ala Ile Asn Gly Thr Pro
            580                 585                 590

Asn Glu Met Ile Thr Val Thr Asp Lys Asp Thr Gly Glu Ile Ser Glu
        595                 600                 605

Lys Leu Lys Leu Gly Thr Ser Thr Leu Ala Gln Gln Trp Leu Ala Tyr
    610                 615                 620

Gly Val Thr Arg Ser Val Thr Lys Arg Ser Val Met Thr Leu Ala Tyr
625                 630                 635                 640

Gly Ser Lys Glu Phe Gly Phe Arg Gln Gln Val Leu Asp Asp Thr Ile
                645                 650                 655

Gln Pro Ala Ile Asp Ser Gly Lys Gly Leu Met Phe Thr Gln Pro Asn
            660                 665                 670

Gln Ala Ala Gly Tyr Met Ala Lys Leu Ile Trp Asp Ala Val Ser Val
        675                 680                 685

Thr Val Val Ala Ala Val Glu Ala Met Asn Trp Leu Lys Ser Ala Ala
    690                 695                 700

Lys Leu Leu Ala Ala Glu Val Lys Asp Lys Thr Lys Glu Ile Leu
705                 710                 715                 720

Arg His Arg Cys Ala Val His Trp Thr Thr Pro Asp Gly Phe Pro Val
                725                 730                 735

Trp Gln Glu Tyr Arg Lys Pro Leu Gln Lys Arg Leu Asp Met Ile Phe
            740                 745                 750

Leu Gly Gln Phe Arg Leu Gln Pro Thr Ile Asn Thr Leu Lys Asp Ser
        755                 760                 765

Gly Ile Asp Ala His Lys Gln Glu Ser Gly Ile Ala Pro Asn Phe Val
    770                 775                 780

His Ser Gln Asp Gly Ser His Leu Arg Met Thr Val Val Tyr Ala His
785                 790                 795                 800

Glu Asn Tyr Gly Ile Glu Ser Phe Ala Leu Ile His Asp Ser Phe Gly
                805                 810                 815

Thr Ile Pro Ala Asp Ala Gly Lys Leu Phe Lys Ala Val Arg Glu Thr
            820                 825                 830

Met Val Ile Thr Tyr Glu Asn Asn Asp Val Leu Ala Asp Phe Tyr Asp
        835                 840                 845

Gln Phe Ala Asp Gln Leu His Glu Thr Gln Leu Asp Lys Met Pro Pro
    850                 855                 860

Leu Pro Lys Lys Gly Asn Leu Asn Leu Gln Asp Ile Leu Lys Ser Asp
865                 870                 875                 880

Phe Ala Phe Ala

<210> SEQ ID NO 67
<211> LENGTH: 884
<212> TYPE: PRT
<213> ORGANISM: Enterobacteria bacteriophage T7M

<400> SEQUENCE: 67

Met Asn Ile Ile Glu Asn Ile Glu Lys Asn Asp Phe Ser Glu Ile Glu
1               5                   10                  15

Leu Ala Ala Ile Pro Phe Asn Thr Leu Ala Asp His Tyr Gly Ser Ala
            20                  25                  30

Leu Ala Lys Glu Gln Leu Ala Leu Glu His Glu Ser Tyr Glu Leu Gly
        35                  40                  45

Glu Arg Arg Phe Leu Lys Met Leu Glu Arg Gln Ala Lys Ala Gly Glu
    50                  55                  60
```

```
Ile Ala Asp Asn Ala Ala Lys Pro Leu Leu Ala Thr Leu Leu Pro
 65                  70                  75                  80

Lys Leu Thr Thr Arg Ile Val Glu Trp Leu Glu Glu Tyr Ala Ser Lys
                 85                  90                  95

Lys Gly Arg Lys Pro Ser Ala Tyr Ala Pro Leu Gln Leu Leu Lys Pro
            100                 105                 110

Glu Ala Ser Ala Phe Ile Thr Leu Lys Val Ile Leu Ala Ser Leu Thr
        115                 120                 125

Ser Thr Asn Met Thr Thr Ile Gln Ala Ala Gly Met Leu Gly Lys
    130                 135                 140

Ala Ile Glu Asp Glu Ala Arg Phe Gly Arg Ile Arg Asp Leu Glu Ala
145                 150                 155                 160

Lys His Phe Lys Lys His Val Glu Glu Gln Leu Asn Lys Arg His Gly
                165                 170                 175

Gln Val Tyr Lys Lys Ala Phe Met Gln Val Val Glu Ala Asp Met Ile
            180                 185                 190

Gly Arg Gly Leu Leu Gly Gly Glu Ala Trp Ser Ser Trp Asp Lys Glu
        195                 200                 205

Thr Thr Met His Val Gly Ile Arg Leu Ile Glu Met Leu Ile Glu Ser
    210                 215                 220

Thr Gly Leu Val Glu Leu Gln Arg His Asn Ala Gly Asn Ala Gly Ser
225                 230                 235                 240

Asp His Glu Ala Leu Gln Leu Ala Gln Glu Tyr Val Asp Val Leu Ala
                245                 250                 255

Lys Arg Ala Gly Ala Leu Ala Gly Ile Ser Pro Met Phe Gln Pro Cys
            260                 265                 270

Val Val Pro Pro Lys Pro Trp Val Ala Ile Thr Gly Gly Gly Tyr Trp
        275                 280                 285

Ala Asn Gly Arg Arg Pro Leu Ala Leu Val Arg Thr His Ser Lys Lys
    290                 295                 300

Gly Leu Met Arg Tyr Glu Asp Val Tyr Met Pro Glu Val Tyr Lys Ala
305                 310                 315                 320

Val Asn Leu Ala Gln Asn Thr Ala Trp Lys Ile Asn Lys Lys Val Leu
                325                 330                 335

Ala Val Val Asn Glu Ile Val Asn Trp Lys Asn Cys Pro Val Ala Asp
            340                 345                 350

Ile Pro Ser Leu Glu Arg Gln Glu Leu Pro Pro Lys Pro Asp Asp Ile
        355                 360                 365

Asp Thr Asn Glu Ala Ala Leu Lys Glu Trp Lys Lys Ala Ala Ala Gly
    370                 375                 380

Ile Tyr Arg Leu Asp Lys Ala Arg Val Ser Arg Arg Ile Ser Leu Glu
385                 390                 395                 400

Phe Met Leu Glu Gln Ala Asn Lys Phe Ala Ser Lys Lys Ala Ile Trp
                405                 410                 415

Phe Pro Tyr Asn Met Asp Trp Arg Gly Arg Val Tyr Ala Val Pro Met
            420                 425                 430

Phe Asn Pro Gln Gly Asn Asp Met Thr Lys Gly Leu Leu Thr Leu Ala
        435                 440                 445

Lys Gly Lys Pro Ile Gly Glu Glu Gly Phe Tyr Trp Leu Lys Ile His
    450                 455                 460

Gly Ala Asn Cys Ala Gly Val Asp Lys Val Pro Phe Pro Glu Arg Ile
465                 470                 475                 480

Ala Phe Ile Glu Lys His Val Asp Asp Ile Leu Ala Cys Ala Lys Asp
```

```
                485                 490                 495
Pro Ile Asn Asn Thr Trp Trp Ala Glu Gln Asp Ser Pro Phe Cys Phe
                500                 505                 510

Leu Ala Phe Cys Phe Glu Tyr Ala Gly Val Thr His His Gly Leu Ser
                515                 520                 525

Tyr Asn Cys Ser Leu Pro Leu Ala Phe Asp Gly Ser Cys Ser Gly Ile
                530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
                565                 570                 575

Gln Lys Val Asn Glu Ile Leu Lys Gln Asp Ala Ile Asn Gly Thr Pro
                580                 585                 590

Asn Glu Met Ile Thr Val Thr Asp Lys Asp Thr Gly Glu Ile Ser Glu
                595                 600                 605

Lys Leu Lys Leu Gly Thr Ser Thr Leu Ala Gln Gln Trp Leu Ala Tyr
                610                 615                 620

Gly Val Thr Arg Ser Val Thr Lys Arg Ser Val Met Thr Leu Ala Tyr
625                 630                 635                 640

Gly Ser Lys Glu Phe Gly Phe Arg Gln Gln Val Leu Asp Asp Thr Ile
                645                 650                 655

Gln Pro Ala Ile Asp Ser Gly Lys Gly Leu Met Phe Thr Gln Pro Asn
                660                 665                 670

Gln Ala Ala Gly Tyr Met Ala Lys Leu Ile Trp Asp Ala Val Ser Val
                675                 680                 685

Thr Val Val Ala Ala Val Glu Ala Met Asn Trp Leu Lys Ser Ala Ala
690                 695                 700

Lys Leu Leu Ala Ala Glu Val Lys Asp Lys Thr Lys Glu Ile Leu
705                 710                 715                 720

Arg His Arg Cys Ala Val His Trp Thr Thr Pro Asp Gly Phe Pro Val
                725                 730                 735

Trp Gln Glu Tyr Arg Lys Pro Leu Gln Lys Arg Leu Asp Met Ile Phe
                740                 745                 750

Leu Gly Gln Phe Arg Leu Gln Pro Thr Ile Asn Thr Leu Lys Asp Ser
                755                 760                 765

Gly Ile Asp Ala His Lys Gln Glu Ser Gly Ile Ala Pro Asn Phe Val
                770                 775                 780

His Ser Gln Asp Gly Ser His Leu Arg Met Thr Val Val Tyr Ala His
785                 790                 795                 800

Glu Lys Tyr Gly Ile Glu Ser Phe Ala Leu Ile His Asp Ser Phe Gly
                805                 810                 815

Thr Ile Pro Ala Asp Ala Gly Lys Leu Phe Lys Ala Val Arg Glu Thr
                820                 825                 830

Met Val Ile Thr Tyr Glu Asn Asn Asp Val Leu Ala Asp Phe Tyr Ser
                835                 840                 845

Gln Phe Ala Asp Gln Leu His Glu Thr Gln Leu Asp Lys Met Pro Pro
                850                 855                 860

Leu Pro Lys Lys Gly Asn Leu Asn Leu Gln Asp Ile Leu Lys Ser Asp
865                 870                 875                 880

Phe Ala Phe Ala
```

<210> SEQ ID NO 68
<211> LENGTH: 884

<212> TYPE: PRT
<213> ORGANISM: Enterobacteria bacteriophage T3

<400> SEQUENCE: 68

```
Met Asn Ile Ile Glu Asn Ile Glu Lys Asn Asp Phe Ser Glu Ile Glu
1               5                   10                  15

Leu Ala Ala Ile Pro Phe Asn Thr Leu Ala Asp His Tyr Gly Ser Ala
            20                  25                  30

Leu Ala Lys Glu Gln Leu Ala Leu Glu His Glu Ser Tyr Glu Leu Gly
        35                  40                  45

Glu Arg Arg Phe Leu Lys Met Leu Glu Arg Gln Ala Lys Ala Gly Glu
    50                  55                  60

Ile Ala Asp Asn Ala Ala Ala Lys Pro Leu Leu Ala Thr Leu Leu Pro
65                  70                  75                  80

Lys Leu Thr Thr Arg Ile Val Glu Trp Leu Glu Tyr Ala Ser Lys
                85                  90                  95

Lys Gly Arg Lys Pro Ser Ala Tyr Ala Pro Leu Gln Leu Leu Lys Pro
            100                 105                 110

Glu Ala Ser Ala Phe Ile Thr Leu Lys Val Ile Leu Ala Ser Leu Thr
        115                 120                 125

Ser Thr Asn Met Thr Thr Ile Gln Ala Ala Ala Gly Met Leu Gly Lys
130                 135                 140

Ala Ile Glu Asp Glu Ala Arg Phe Gly Arg Ile Arg Asp Leu Glu Ala
145                 150                 155                 160

Lys His Phe Lys Lys His Val Glu Glu Gln Leu Asn Lys Arg His Gly
                165                 170                 175

Gln Val Tyr Lys Lys Ala Phe Met Gln Val Val Glu Ala Asp Met Ile
            180                 185                 190

Gly Arg Gly Leu Leu Gly Gly Glu Ala Trp Ser Ser Trp Asp Lys Glu
        195                 200                 205

Thr Thr Met His Val Gly Ile Arg Leu Ile Glu Met Leu Ile Glu Ser
210                 215                 220

Thr Gly Leu Val Glu Leu Gln Arg His Asn Ala Gly Asn Ala Gly Ser
225                 230                 235                 240

Asp His Glu Ala Leu Gln Leu Ala Gln Glu Tyr Val Asp Val Leu Ala
                245                 250                 255

Lys Arg Ala Gly Ala Leu Ala Gly Ile Ser Pro Met Phe Gln Pro Cys
            260                 265                 270

Val Val Pro Pro Lys Pro Trp Val Ala Ile Thr Gly Gly Gly Tyr Trp
        275                 280                 285

Ala Asn Gly Arg Arg Pro Leu Ala Leu Val Arg Thr His Ser Lys Lys
290                 295                 300

Gly Leu Met Arg Tyr Glu Asp Val Tyr Met Pro Glu Val Tyr Lys Ala
305                 310                 315                 320

Val Asn Leu Ala Gln Asn Thr Ala Trp Lys Ile Asn Lys Lys Val Leu
                325                 330                 335

Ala Val Val Asn Glu Ile Val Asn Trp Lys Asn Cys Pro Val Ala Asp
            340                 345                 350

Ile Pro Ser Leu Glu Arg Gln Glu Leu Pro Pro Lys Pro Asp Asp Ile
        355                 360                 365

Asp Thr Asn Glu Ala Ala Leu Lys Glu Trp Lys Lys Ala Ala Ala Gly
370                 375                 380

Ile Tyr Arg Leu Asp Lys Ala Arg Val Ser Arg Arg Ile Ser Leu Glu
385                 390                 395                 400
```

```
Phe Met Leu Glu Gln Ala Asn Lys Phe Ala Ser Lys Ala Ile Trp
                405                 410                 415

Phe Pro Tyr Asn Met Asp Trp Arg Gly Arg Val Tyr Ala Val Pro Met
            420                 425                 430

Phe Asn Pro Gln Gly Asn Asp Met Thr Lys Gly Leu Leu Thr Leu Ala
            435                 440                 445

Lys Gly Lys Pro Ile Gly Glu Glu Gly Phe Tyr Trp Leu Lys Ile His
        450                 455                 460

Gly Ala Asn Cys Ala Gly Val Asp Lys Val Pro Phe Pro Glu Arg Ile
465                 470                 475                 480

Ala Phe Ile Glu Lys His Val Asp Asp Ile Leu Ala Cys Ala Lys Asp
                485                 490                 495

Pro Ile Asn Asn Thr Trp Trp Ala Glu Gln Asp Ser Pro Phe Cys Phe
            500                 505                 510

Leu Ala Phe Cys Phe Glu Tyr Ala Gly Val Thr His His Gly Leu Ser
            515                 520                 525

Tyr Asn Cys Ser Leu Pro Leu Ala Phe Asp Gly Ser Cys Ser Gly Ile
        530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
            565                 570                 575

Gln Lys Val Asn Glu Ile Leu Lys Gln Asp Ala Ile Asn Gly Thr Pro
        580                 585                 590

Asn Glu Met Ile Thr Val Thr Asp Lys Asp Thr Gly Glu Ile Ser Glu
            595                 600                 605

Lys Leu Lys Leu Gly Thr Ser Thr Leu Ala Gln Gln Trp Leu Ala Tyr
        610                 615                 620

Gly Val Thr Arg Ser Val Thr Lys Arg Ser Val Met Thr Leu Ala Tyr
625                 630                 635                 640

Gly Ser Lys Glu Phe Gly Phe Arg Gln Gln Val Leu Asp Asp Thr Ile
            645                 650                 655

Gln Pro Ala Ile Asp Ser Gly Lys Gly Leu Met Phe Thr Gln Pro Asn
            660                 665                 670

Gln Ala Ala Gly Tyr Met Ala Lys Leu Ile Trp Asp Ala Val Ser Val
        675                 680                 685

Thr Val Val Ala Ala Val Glu Ala Met Asn Trp Leu Lys Ser Ala Ala
        690                 695                 700

Lys Leu Leu Ala Ala Glu Val Lys Asp Lys Lys Thr Lys Glu Ile Leu
705                 710                 715                 720

Arg His Arg Cys Ala Val His Trp Thr Thr Pro Asp Gly Phe Pro Val
                725                 730                 735

Trp Gln Glu Tyr Arg Lys Pro Leu Gln Lys Arg Leu Asp Met Ile Phe
            740                 745                 750

Leu Gly Gln Phe Arg Leu Gln Pro Thr Ile Asn Thr Leu Lys Asp Ser
        755                 760                 765

Gly Ile Asp Ala His Lys Gln Glu Ser Gly Ile Ala Pro Asn Phe Val
        770                 775                 780

His Ser Gln Asp Gly Ser His Leu Arg Met Thr Val Val Tyr Ala His
785                 790                 795                 800

Glu Lys Tyr Gly Ile Glu Ser Phe Ala Leu Ile His Asp Ser Phe Gly
            805                 810                 815
```

Thr Ile Pro Ala Asp Ala Gly Lys Leu Phe Lys Ala Val Arg Glu Thr
            820                 825                 830

Met Val Ile Thr Tyr Glu Asn Asn Asp Val Leu Ala Asp Phe Tyr Ser
            835                 840                 845

Gln Phe Ala Asp Gln Leu His Glu Thr Gln Leu Asp Lys Met Pro Pro
850                 855                 860

Leu Pro Lys Lys Gly Asn Leu Asn Leu Gln Asp Ile Leu Lys Ser Asp
865                 870                 875                 880

Phe Ala Phe Ala

<210> SEQ ID NO 69
<211> LENGTH: 883
<212> TYPE: PRT
<213> ORGANISM: Artificial Sequence
<220> FEATURE:
<223> OTHER INFORMATION: Synthetic construct

<400> SEQUENCE: 69

Met Asn Ile Ile Asn Ile Ala Lys Asn Asp Phe Ser Asp Ile Glu Leu
1               5                   10                  15

Ala Ala Ile Pro Phe Asn Ile Leu Ala Asp His Tyr Gly Ala Gln Leu
            20                  25                  30

Ala Arg Glu Gln Leu Ala Leu Glu His Glu Ala Tyr Glu Glu Gly Glu
        35                  40                  45

Lys Arg Phe Leu Lys Met Leu Glu Arg Gln Ile Lys Ala Gly Glu Phe
    50                  55                  60

Ala Asp Asn Ala Ala Ala Lys Pro Leu Leu Ser Thr Leu Leu Pro Lys
65                  70                  75                  80

Leu Ile Ala Arg Ile Asn Asp Trp Phe Glu Glu Val Ala Ala Lys Arg
                85                  90                  95

Gly Lys Lys Pro Val Ala Tyr Asn Pro Leu Gln His Val Lys Pro Glu
            100                 105                 110

Ala Ala Ala Phe Ile Thr Leu Lys Val Thr Leu Ala Cys Leu Thr Lys
        115                 120                 125

Ala Glu Phe Thr Thr Ile Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys His Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp Thr Lys Glu Glu
        195                 200                 205

Ser Ile His Val Gly Val Arg Met Leu Glu Leu Leu Ile Glu Ser Thr
    210                 215                 220

Gly Leu Val Glu Leu His Arg Pro Asn Ala Gly Asn Val Gly Lys Asp
225                 230                 235                 240

Val Glu Met Ile Gln Leu Ala Pro Glu Tyr Val Asp Leu Leu Ala Lys
                245                 250                 255

Arg Ala Gly Ala Leu Ala Gly Ile Ser Pro Met Tyr Gln Pro Cys Val
            260                 265                 270

Val Pro Pro Lys Pro Trp Thr Ser Ile Val Gly Gly Gly Tyr Trp Ala
        275                 280                 285

Asn Gly Arg Arg Pro Leu Ala Leu Val Arg Thr His Ser Lys Lys Ala

```
            290                 295                 300
Leu Met Arg Tyr Glu Asp Val Tyr Met Pro Glu Val Tyr Lys Ala Val
305                 310                 315                 320

Asn Ile Ala Gln Asn Thr Pro Trp Lys Ile Asn Lys Lys Val Leu Ala
                325                 330                 335

Val Val Asn Glu Ile Val Asn Trp Lys His Cys Pro Val Ala Asp Val
            340                 345                 350

Pro Ala Ile Glu Arg Glu Leu Pro Pro Lys Pro Glu Asp Ile Asp
        355                 360                 365

Thr Asn Glu Ala Ala Leu Lys Ala Trp Lys Lys Ala Ala Ala Ile
    370                 375                 380

Tyr Arg Lys Asp Lys Ala Arg Val Ser Arg Arg Leu Ser Met Glu Phe
385                 390                 395                 400

Met Leu Glu Gln Ala Asn Lys Phe Ala Asn Phe Lys Ala Ile Trp Phe
                405                 410                 415

Pro Tyr Asn Met Asp Trp Arg Gly Arg Val Tyr Ala Val Pro Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Asp Gly Phe Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Asp Asn His Glu Asn Ile Met Ala Cys Ala Lys Asp Pro
                485                 490                 495

Leu Asn Asn Glu Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Ile Gly Gly Arg Ala Val Asn
545                 550                 555                 560

Leu Leu Pro Ser Glu Thr Val Gln Asp Ile Tyr Gly Ile Val Ala Asp
                565                 570                 575

Lys Val Asn Glu Ile Leu Lys Gln Asp Ala Ile Asn Gly Thr Asp Asn
            580                 585                 590

Glu Val Glu Thr Val Thr Asp Lys Asp Thr Gly Glu Ile Thr Glu Lys
        595                 600                 605

Leu Lys Leu Gly Thr Lys Glu Leu Ala Gly Gln Trp Leu Ala Tyr Gly
    610                 615                 620

Val Thr Arg Lys Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ala Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Lys Glu Val Leu Arg
705                 710                 715                 720
```

```
Lys Arg Cys Ala Val His Trp Val Thr Pro Asp Gly Phe Pro Val Trp
                725                 730                 735

Gln Glu Tyr Arg Lys Pro Val Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Met Thr Val Val His Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Gly Asn Leu Phe Lys Ala Val Arg Glu Thr Met
            820                 825                 830

Val Asn Thr Tyr Glu Asp Asn Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Gln Asp Ile Leu Lys Ser Asp Phe
865                 870                 875                 880

Ala Phe Ala

<210> SEQ ID NO 70
<211> LENGTH: 883
<212> TYPE: PRT
<213> ORGANISM: Artificial Sequence
<220> FEATURE:
<223> OTHER INFORMATION: Synthetic construct

<400> SEQUENCE: 70

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Lys Arg Phe Leu Lys Met Leu Glu Arg Gln Val Lys Ala Gly Glu Ile
    50                  55                  60

Ala Asp Asn Ala Ala Lys Pro Leu Ile Thr Thr Leu Leu Pro Lys Leu
65                  70                  75                  80

Leu Thr Ala Arg Ile Asn Asp Trp Phe Glu Glu Val Ala Ala Lys Arg
                85                  90                  95

Gly Lys Arg Pro Val Ala Tyr Gln Pro Leu Gln Gly Ile Lys Pro Glu
            100                 105                 110

Ala Val Ala Phe Ile Thr Ile Lys Val Val Leu Ala Ser Leu Thr Ser
        115                 120                 125

Ala Asp Asn Thr Thr Ile Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys His Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190
```

```
Lys Gly Leu Leu Gly Gly Glu Ala Trp Ser Ser Trp Asn Lys Glu Glu
        195                 200                 205

Ser Met His Val Gly Ile Arg Met Ile Glu Met Leu Ile Glu Ser Thr
210                 215                 220

Gly Leu Val Glu Leu His Arg His Asn Ala Gly Val Val Gly Gln Asp
225                 230                 235                 240

Ser Glu Thr Ile Gln Leu Ala Pro Glu Tyr Val Glu Ala Leu Ala Lys
                245                 250                 255

Arg Ala Gly Ala Leu Ala Gly Ile Ser Pro Met Phe Gln Pro Cys Val
                260                 265                 270

Val Pro Pro Lys Pro Trp Val Ser Ile Thr Gly Gly Gly Tyr Trp Ala
        275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Val
305                 310                 315                 320

Asn Ile Ala Gln Asn Thr Ala Trp Lys Ile Asn Lys Lys Val Leu Ala
                325                 330                 335

Val Val Asn Glu Ile Val Asn Trp Lys His Cys Pro Val Glu Asp Ile
            340                 345                 350

Pro Ala Ile Glu Arg Glu Leu Pro Pro Lys Pro Asp Asp Ile Asp
        355                 360                 365

Thr Asn Glu Glu Ala Leu Lys Ala Trp Lys Lys Ala Ala Ala Val
    370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Pro Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Phe Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Asp Asn His Asp Asn Ile Met Ala Cys Ala Lys Asp Pro
                485                 490                 495

Leu Asp Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Asp
                565                 570                 575

Lys Val Asn Glu Ile Leu Lys Gln Asp Val Ile Asn Gly Thr Asp Asn
            580                 585                 590

Glu Val Val Thr Val Thr Asp Lys Asp Thr Gly Glu Ile Ser Glu Lys
        595                 600                 605

Leu Lys Leu Gly Thr Lys Glu Leu Ala Gln Gln Trp Leu Ala Tyr Gly
```

```
            610                 615                 620
Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Asp Ala Val Ser Val Thr
            675                 680                 685

Val Val Ala Ala Val Glu Ala Met Asn Trp Leu Lys Ser Ala Ala Lys
690                 695                 700

Leu Leu Ala Ala Glu Val Lys Asp Lys Lys Thr Lys Glu Ile Leu Arg
705                 710                 715                 720

Lys Arg Cys Ala Val His Trp Val Thr Pro Asp Gly Phe Pro Val Trp
                725                 730                 735

Gln Glu Tyr Arg Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
770                 775                 780

Ser Gln Asp Gly Ser His Leu Arg Met Thr Val Val Tyr Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Gly Asn Leu Phe Lys Ala Val Arg Glu Thr Met
            820                 825                 830

Val Asn Thr Tyr Glu Asn Asp Val Leu Ala Asp Phe Tyr Asp Gln
835                 840                 845

Phe Ala Asp Gln Leu His Glu Ser Gln Leu Asp Lys Met Pro Ala Leu
850                 855                 860

Pro Ala Lys Gly Asn Leu Asn Leu Gln Asp Ile Leu Lys Ser Asp Phe
865                 870                 875                 880

Ala Phe Ala

<210> SEQ ID NO 71
<211> LENGTH: 49
<212> TYPE: DNA
<213> ORGANISM: Artificial Sequence
<220> FEATURE:
<223> OTHER INFORMATION: Synthetic construct

<400> SEQUENCE: 71
aattctaata cgactcacta tagggagagg cccggcatgt ggtgcataa              49

<210> SEQ ID NO 72
<211> LENGTH: 23
<212> TYPE: DNA
<213> ORGANISM: Artificial Sequence
<220> FEATURE:
<223> OTHER INFORMATION: Synthetic construct

<400> SEQUENCE: 72
cagtatgcca agaccgactc aga                                          23

<210> SEQ ID NO 73
<211> LENGTH: 34
```

```
<212> TYPE: DNA
<213> ORGANISM: Artificial Sequence
<220> FEATURE:
<223> OTHER INFORMATION: Synthetic construct

<400> SEQUENCE: 73
cgtacgagaa gaggaagccc aagagccacg tacg                              34

<210> SEQ ID NO 74
<211> LENGTH: 18
<212> TYPE: DNA
<213> ORGANISM: Artificial Sequence
<220> FEATURE:
<223> OTHER INFORMATION: Synthetic construct

<400> SEQUENCE: 74
taatacgact cactatag                                                18

<210> SEQ ID NO 75
<211> LENGTH: 18
<212> TYPE: DNA
<213> ORGANISM: Artificial Sequence
<220> FEATURE:
<223> OTHER INFORMATION: Synthetic construct

<400> SEQUENCE: 75
aattaaccct cactaaag                                                18

<210> SEQ ID NO 76
<211> LENGTH: 18
<212> TYPE: DNA
<213> ORGANISM: Artificial Sequence
<220> FEATURE:
<223> OTHER INFORMATION: Synthetic construct

<400> SEQUENCE: 76
tatttaccct cactaaag                                                18

<210> SEQ ID NO 77
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(22)
<223> OTHER INFORMATION: n is a, c, g, or t

<400> SEQUENCE: 77
atttaggtga cactatagaa gng                                          23
```